(12) United States Patent
Appleman et al.

(10) Patent No.: US 10,576,098 B2
(45) Date of Patent: Mar. 3, 2020

(54) COMPOSITIONS AND METHODS FOR TREATING FIBROTIC DISEASE

(71) Applicant: eFFECTOR Therapeutics, Inc., San Diego, CA (US)

(72) Inventors: James Appleman, San Diego, CA (US); Peggy A. Thompson, San Diego, CA (US)

(73) Assignee: eFFECTOR Therapeutics Inc., San Diego, CA (US)

( * ) Notice: Subject to any disclaimer, the term of this patent is extended or adjusted under 35 U.S.C. 154(b) by 0 days.

(21) Appl. No.: 15/973,281

(22) Filed: May 7, 2018

(65) Prior Publication Data

US 2019/0038657 A1 Feb. 7, 2019

Related U.S. Application Data

(62) Division of application No. 14/616,690, filed on Feb. 7, 2015, now Pat. No. 9,993,494.

(60) Provisional application No. 62/037,497, filed on Aug. 14, 2014, provisional application No. 62/010,004, filed on Jun. 10, 2014, provisional application No. 61/937,272, filed on Feb. 7, 2014.

(51) Int. Cl.

| | |
|---|---|
| *A61K 31/713* | (2006.01) |
| *A61K 31/155* | (2006.01) |
| *A61K 31/16* | (2006.01) |
| *A61K 31/357* | (2006.01) |
| *A61K 31/4245* | (2006.01) |
| *A61K 31/436* | (2006.01) |
| *A61K 31/4418* | (2006.01) |
| *A61K 31/496* | (2006.01) |
| *A61K 31/519* | (2006.01) |
| *A61K 31/706* | (2006.01) |
| *A61K 45/06* | (2006.01) |

(52) U.S. Cl.
CPC .......... *A61K 31/713* (2013.01); *A61K 31/155* (2013.01); *A61K 31/16* (2013.01); *A61K 31/357* (2013.01); *A61K 31/4245* (2013.01); *A61K 31/436* (2013.01); *A61K 31/4418* (2013.01); *A61K 31/496* (2013.01); *A61K 31/519* (2013.01); *A61K 31/706* (2013.01); *A61K 45/06* (2013.01)

(58) Field of Classification Search
CPC ... A61K 31/713; A61K 45/06; A61K 2300/00
USPC .................... 435/6.1, 91.1, 91.31, 455, 458; 514/44 R, 44 A; 536/23.1, 24.5
See application file for complete search history.

(56) References Cited

U.S. PATENT DOCUMENTS

| | | | |
|---|---|---|---|
| 2010/0152531 A1* | 6/2010 | Goodman | A61F 2/2481 600/37 |
| 2013/0178472 A1* | 7/2013 | Bellevergue | C07D 471/04 514/234.5 |

OTHER PUBLICATIONS

Rosenbloom et al. (Physiology in Medicine: A series of articles linking medicine with science, vol. 152, pp. 159-166 (2010)).*
Wynn et al (Nat. Med., vol. 18, No. 7, pp. 1028-1040 (2012)).*
Schuppan et al (J. Hepatology (Supp), S66-S74 (2012)).*
Schwanhausser et al (Nature, vol. 473, pp. 337-342 (2011)).*
Hinz et al (Am. J. Pathol., vol. 170, No. 6, pp. 1807-1816 (2007)) (Year: 2007).*
Noble et al (Clip. Chest Med., vol. 25, pp. 749-758 (2004)) (Year: 2004).*
Low et al (Molecular Cell, vol. 20, pp. 709-722 (2005)) (Year: 2005).*
Goc et al. (Nov. 2011) "TGFβ- and Bleomycin-Induced Extracellular Matrix Synthesis is Mediated Through Akt nd Mammalian Target of Rapamycin (mTOR)", Journal of Cellular Physiology, 226(11):3004-3013.

* cited by examiner

*Primary Examiner* — Jane J Zara
(74) *Attorney, Agent, or Firm* — Mintz, Levin, Cohn, Ferris, Glovsky and Popeo, P.C.

(57) ABSTRACT

The present disclosure relates to compositions and methods for treating or preventing a fibrotic disorder or disease.

9 Claims, 28 Drawing Sheets

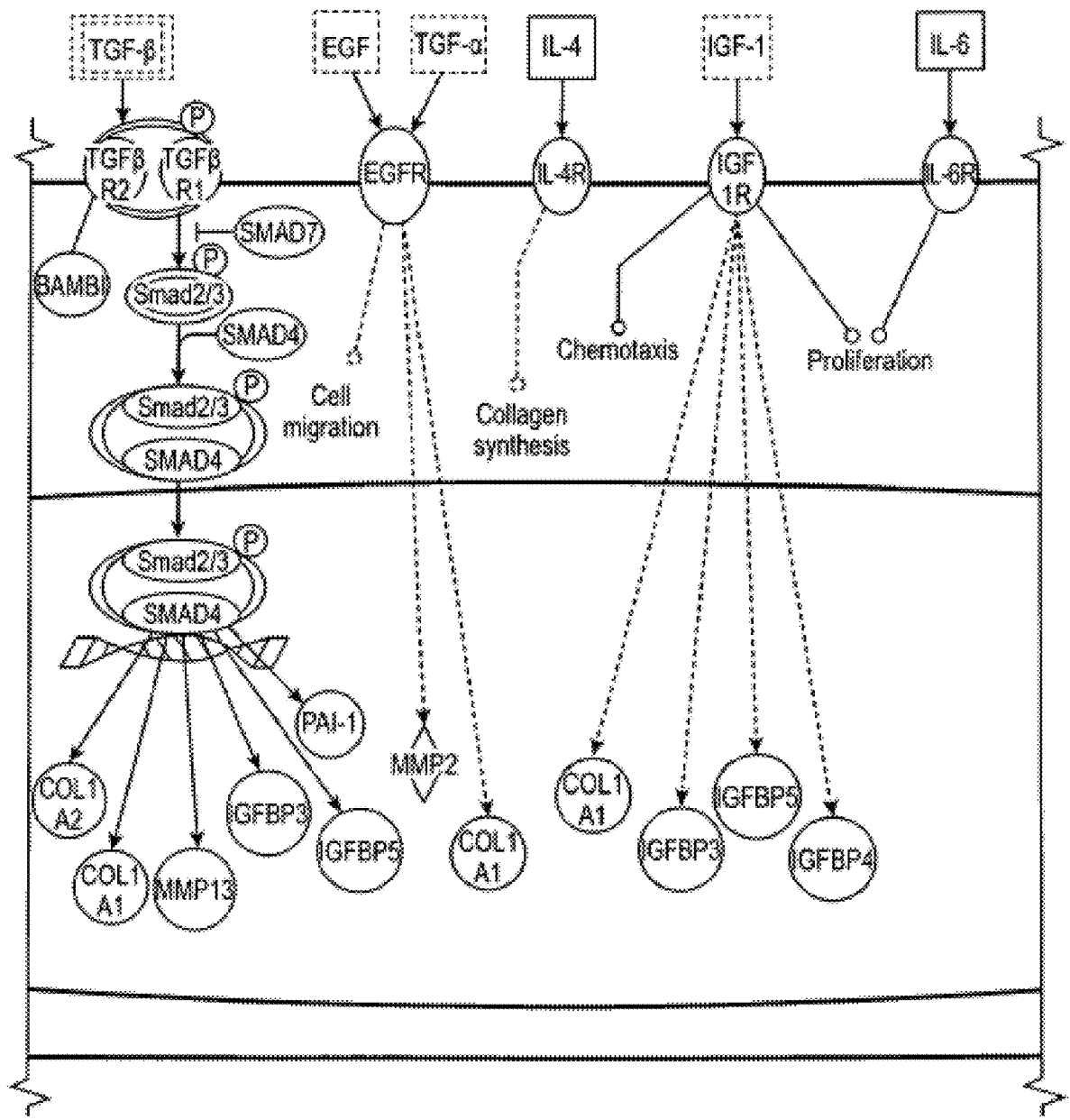
Fig. 4A (Cont. 1)

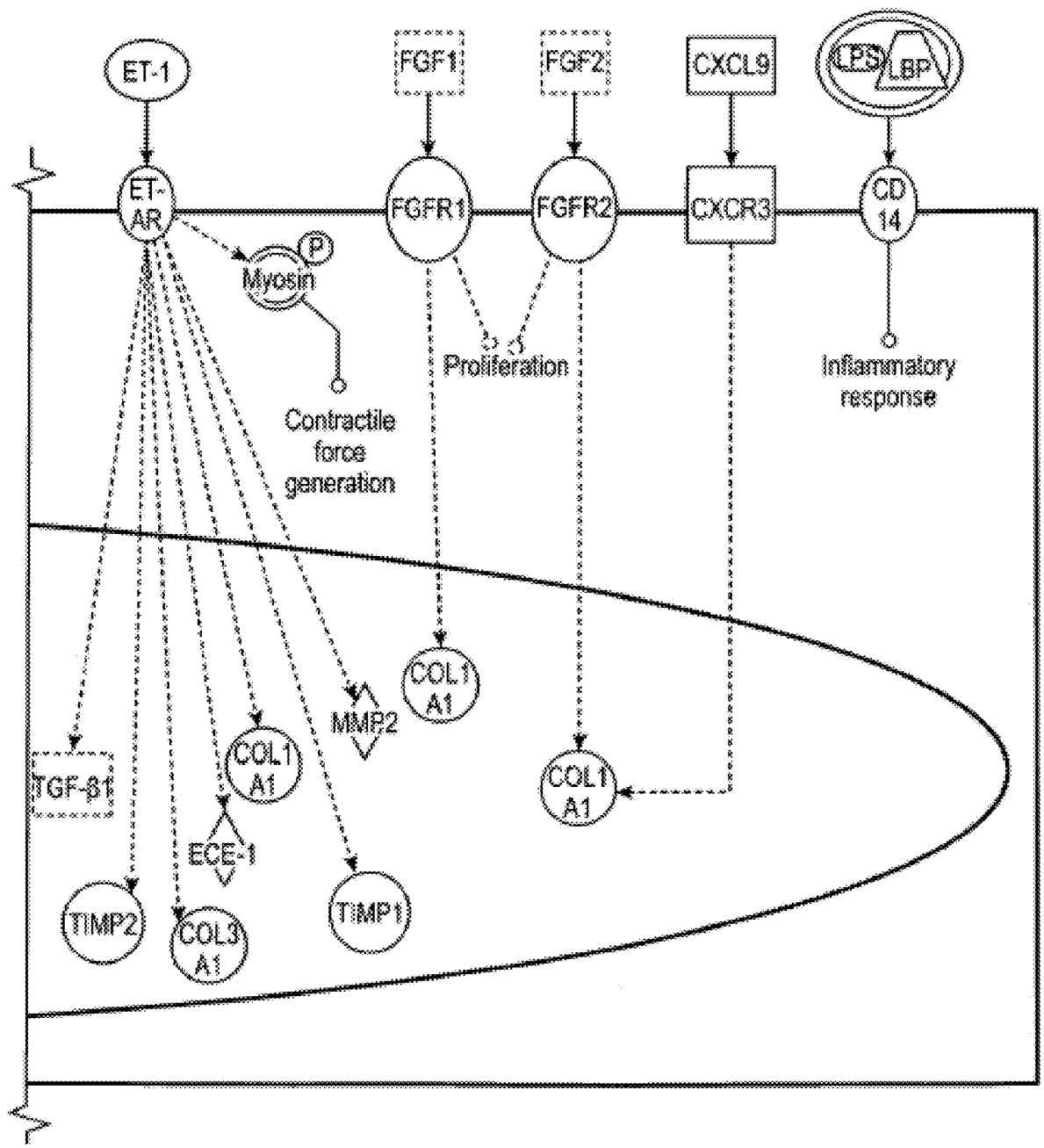
Fig. 4A (Cont. 2)

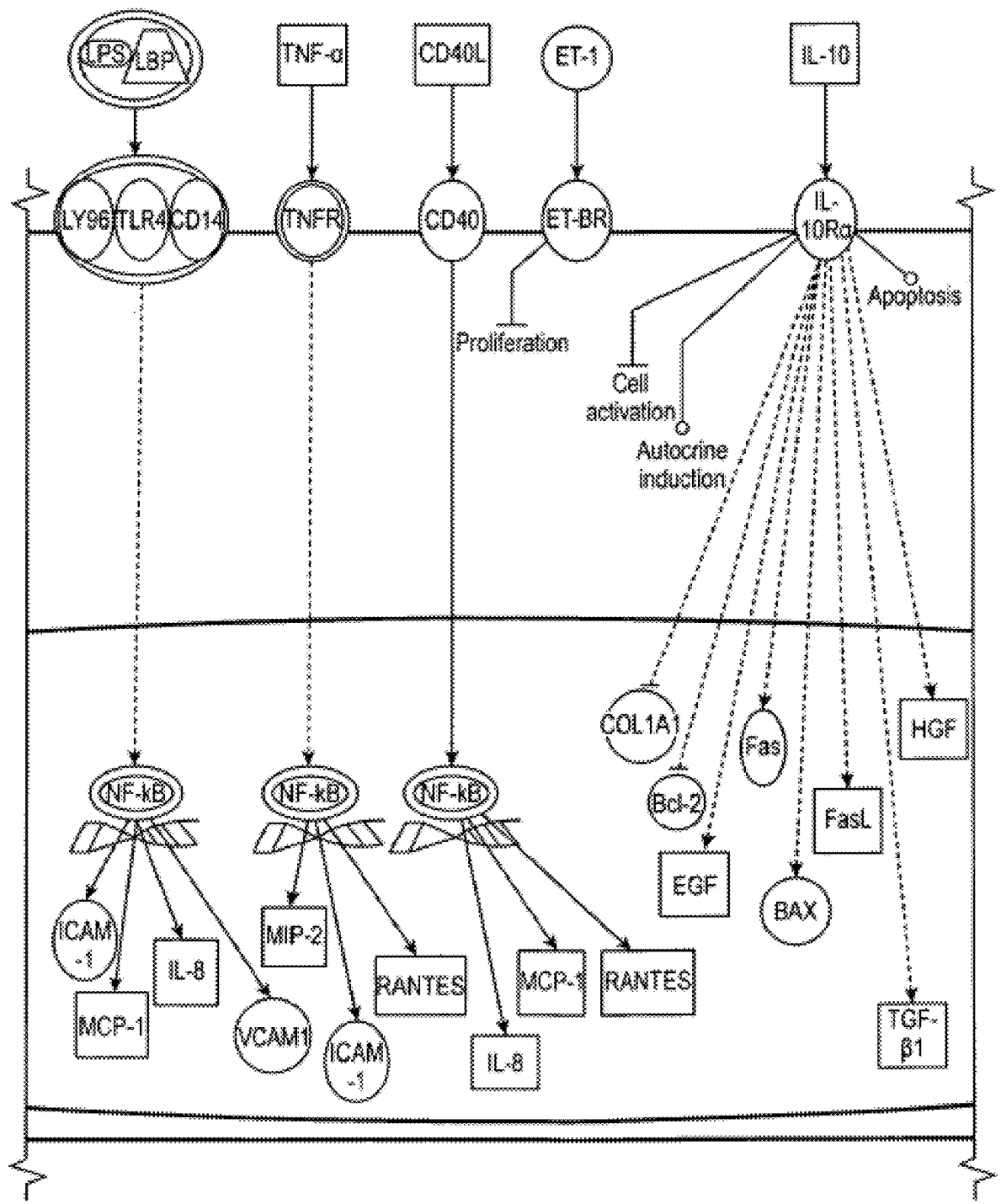
*Fig. 4B (Cont. 1)*

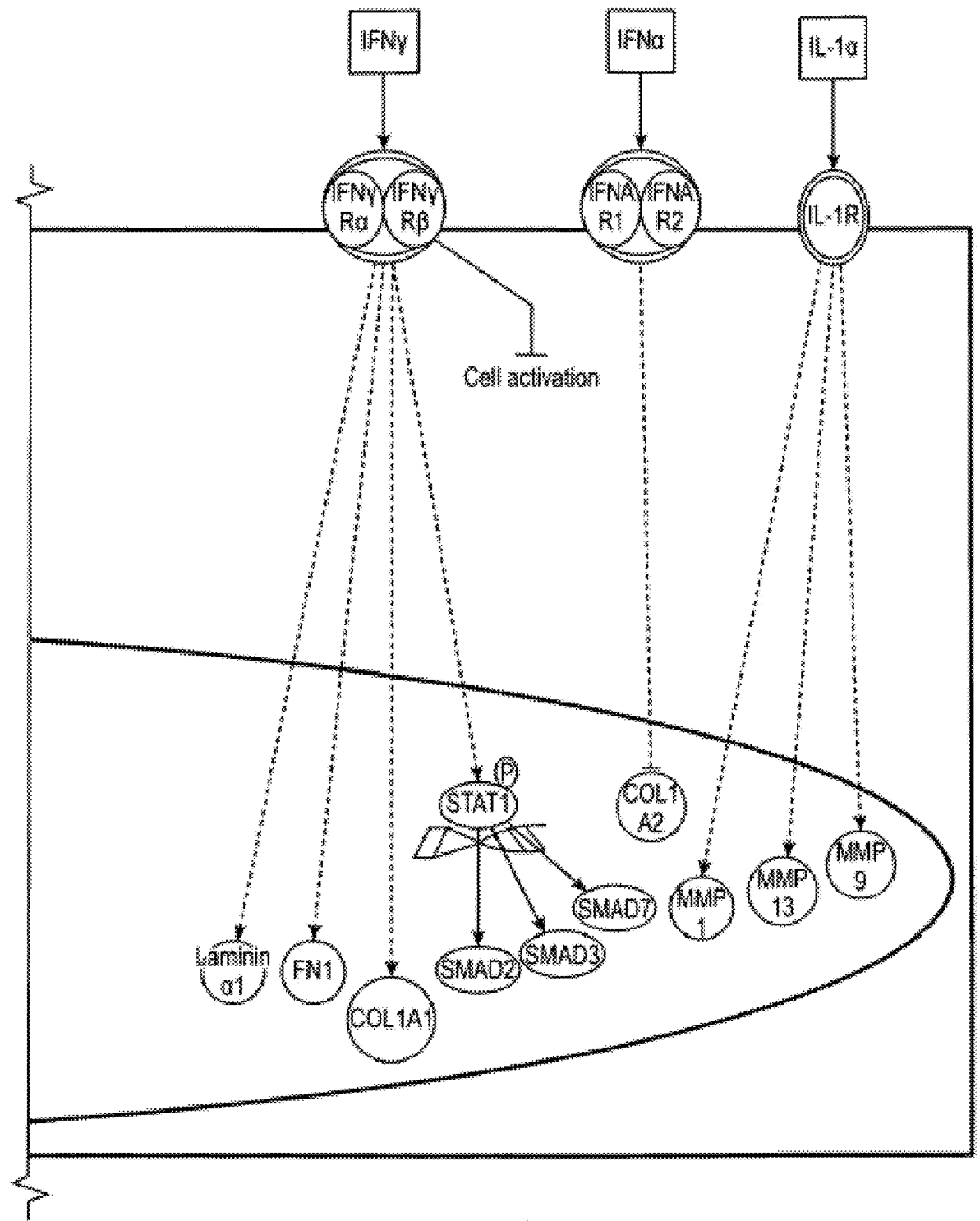
Fig. 4B (Cont. 2)

| Target | Log Ratio | p-value | Target | Log Ratio | p-value |
|---|---|---|---|---|---|
| A2M | -2.075 | 9.99E-15 | IGFBP3 | 5.015 | 1.45E-81 |
| ACTA2 | 6.372 | 1.20E-119 | IGFBP4 | -1.687 | 1.08E-09 |
| CCL2 | -4.057 | 1.99E-19 | IL1R1 | -1.642 | 6.72E-11 |
| COL11A1 | 2.713 | 7.58E-08 | IL6R | -3.584 | 1.36E-12 |
| COL16A1 | 1.720 | 5.95E-09 | MYH11 | 5.684 | 1.68E-15 |
| COL1A1 | 2.043 | 3.42E-15 | MYL6 | 1.884 | 3.00E-11 |
| COL4A1 | 3.940 | 9.03E-53 | MYL9 | 2.533 | 3.22E-21 |
| COL4A2 | 2.283 | 8.14E-22 | NGFR | 7.698 | 9.57E-77 |
| COL4A5 | -2.099 | 2.65E-11 | PDGFA | 3.938 | 2.26E-48 |
| COL4A6 | -1.813 | 3.76E-07 | PDGFD | -1.776 | 5.14E-08 |
| COL5A1 | 2.380 | 5.70E-23 | PDGFRA | -2.279 | 8.12E-21 |
| COL7A1 | 2.913 | 6.35E-20 | SERPINE1 | 5.579 | 5.79E-36 |
| COL8A1 | 2.167 | 1.22E-18 | SMAD3 | -3.521 | 5.50E-37 |
| COL8A2 | 4.032 | 3.35E-50 | SMAD7 | 2.034 | 2.33E-16 |
| CTGF | 2.866 | 7.18E-11 | TGFB1 | 2.028 | 2.67E-14 |
| EDN1 | 6.424 | 4.38E-14 | TGFBR1 | 2.337 | 1.12E-11 |
| FGF1 | 3.101 | 4.50E-14 | TNFRSF11B | -2.172 | 8.44E-15 |
| HGF | -3.538 | 4.77E-33 | TNFRSF1B | -5.279 | 1.80E-23 |
| ICAM1 | -3.106 | 3.97E-13 | VCAM1 | -4.070 | 4.41E-27 |
| IGF1 | 5.316 | 7.89E-14 | | | |

*Fig. 4C*

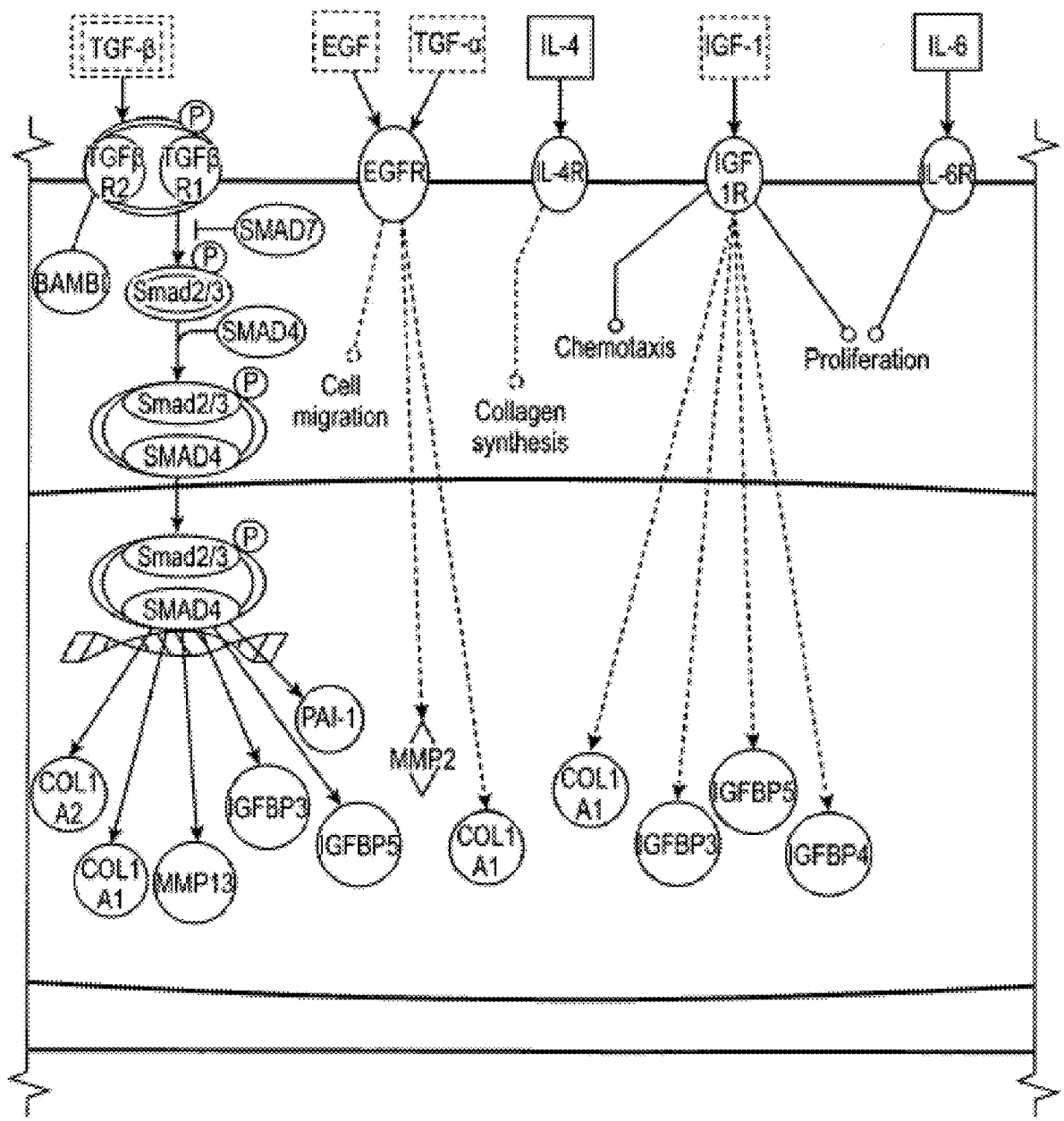
Fig. 5A (Cont. 1)

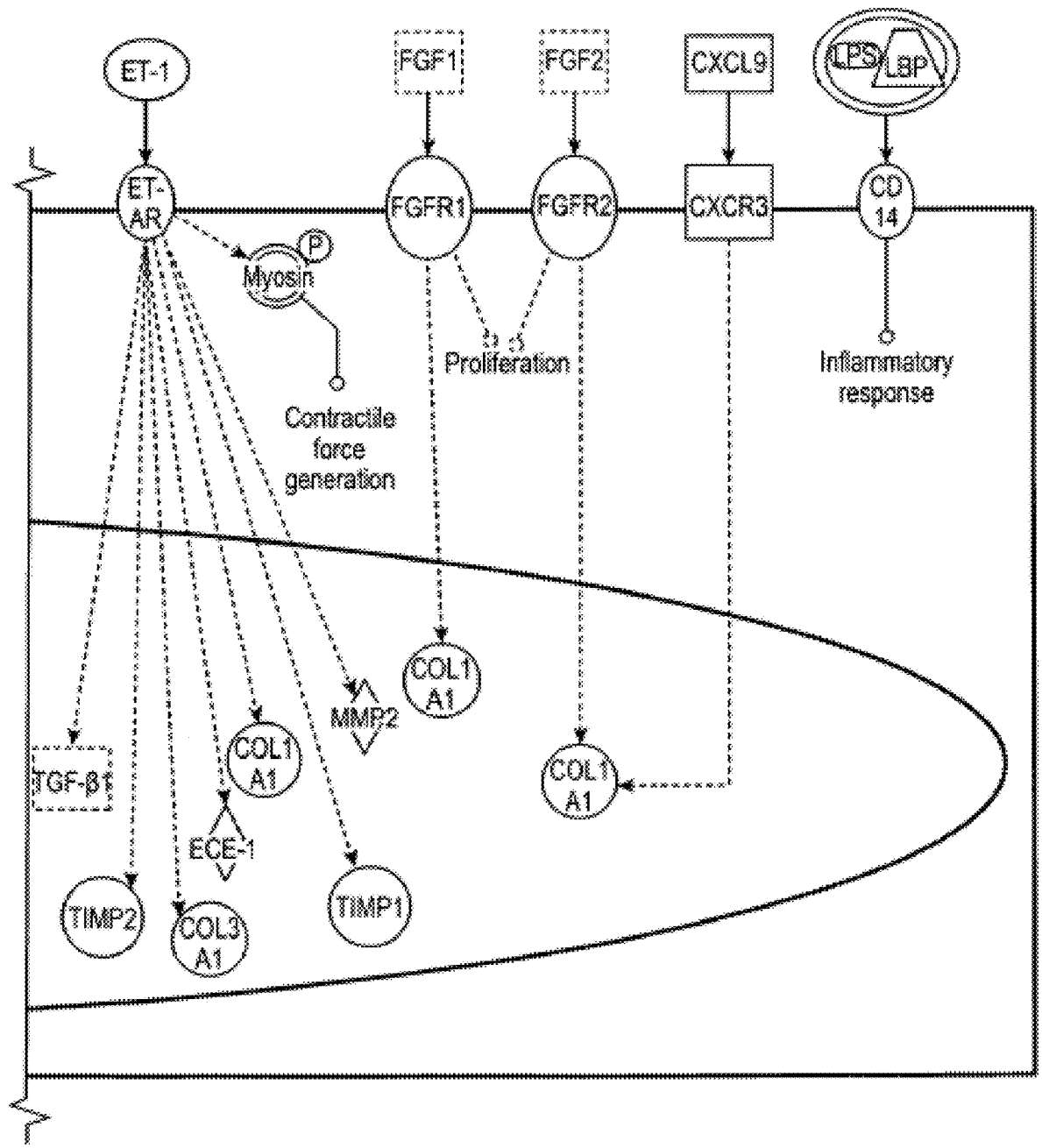
Fig. 5A (Cont. 2)

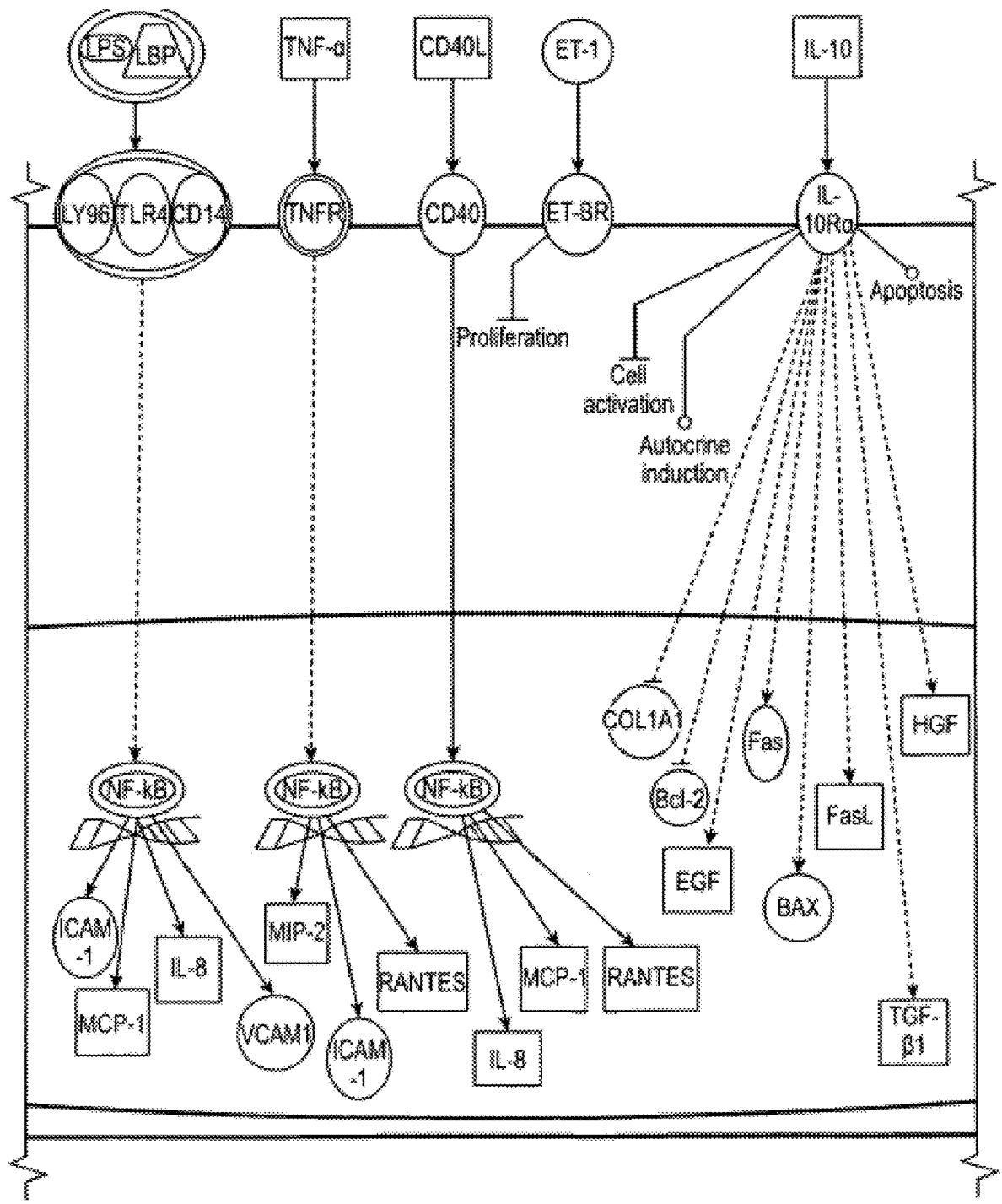
*Fig. 5B (Cont. 1)*

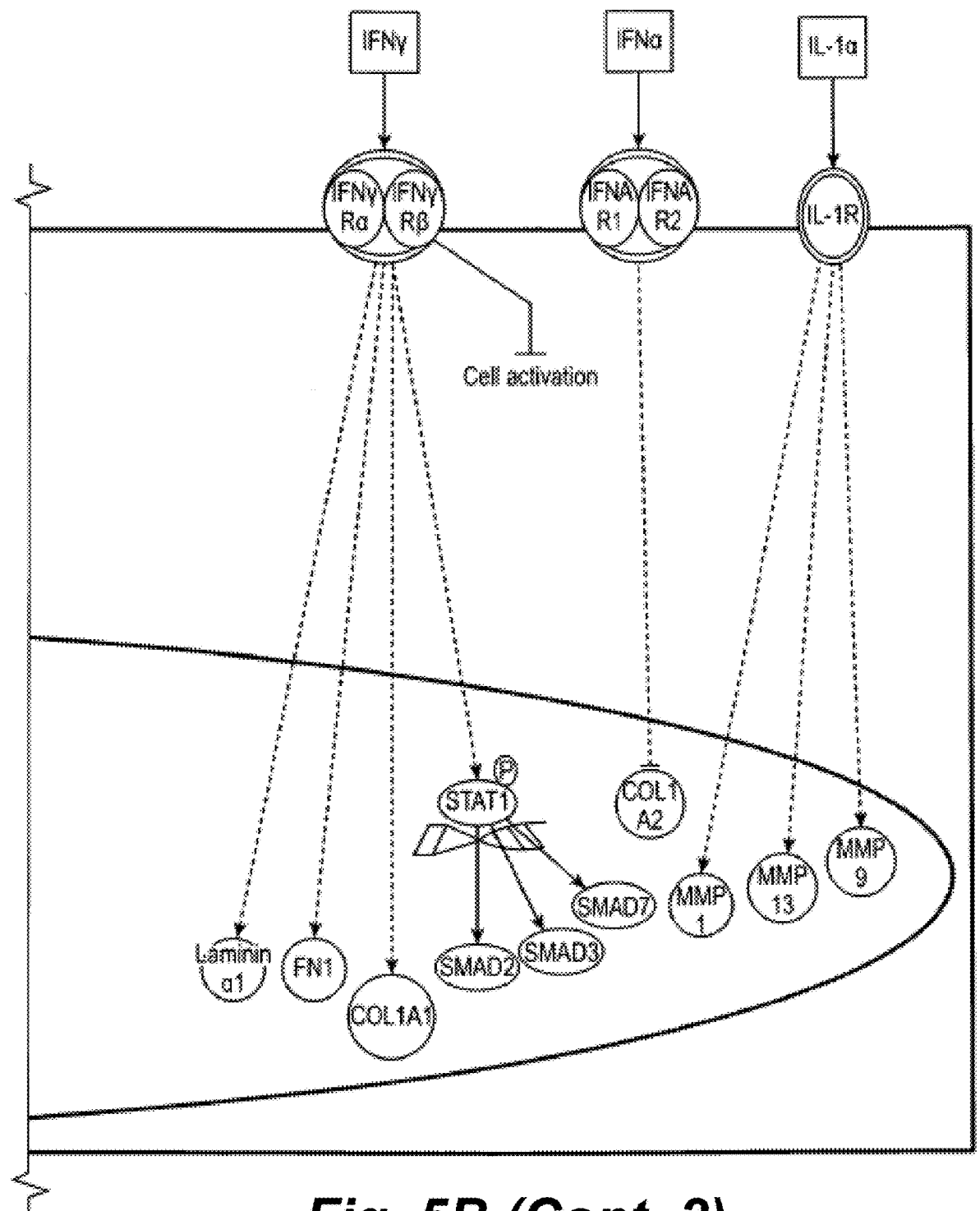
Fig. 5B (Cont. 2)

| Target | Log Ratio | p-value | Target | Log Ratio | p-value |
|---|---|---|---|---|---|
| A2M | -2.116 | 4.00E-19 | IGFBP3 | 5.216 | 1.76E-189 |
| ACTA2 | 5.893 | 4.36E-112 | IGFBP4 | -1.832 | 1.23E-42 |
| CCL2 | -3.854 | 4.18E-55 | IL1R1 | -2.645 | 1.03E-24 |
| COL10A1 | 3.007 | 2.25E-15 | IL6R | -3.772 | 1.94E-34 |
| COL11A1 | 3.482 | 9.18E-67 | MMP1 | -1.889 | 2.47E-27 |
| COL16A1 | 1.938 | 1.19E-20 | MYH9 | 1.547 | 1.64E-14 |
| COL1A1 | 1.949 | 7.64E-15 | MYH10 | 1.657 | 2.51E-09 |
| COL21A1 | -2.991 | 2.12E-08 | MYH11 | 5.878 | 5.64E-29 |
| COL4A1 | 3.869 | 3.22E-27 | MYL6 | 2.088 | 1.31E-31 |
| COL4A2 | 2.700 | 3.90E-23 | MYL9 | 3.119 | 1.52E-99 |
| COL4A5 | -2.181 | 6.65E-28 | NGFR | 7.071 | 4.55E-151 |
| COL4A6 | -2.073 | 2.51E-29 | PDGFA | 4.505 | 1.93E-31 |
| COL5A1 | 2.585 | 6.00E-21 | PDGFD | -2.805 | 1.14E-14 |
| COL7A1 | 3.575 | 1.25E-26 | PDGFRA | -2.432 | 2.65E-42 |
| COL8A1 | 2.002 | 4.63E-38 | SERPINE1 | 5.366 | 9.74E-49 |
| COL8A2 | 4.162 | 1.08E-44 | SMAD3 | -3.835 | 3.47E-84 |
| COL9A3 | 3.158 | 1.42E-10 | SMAD7 | 2.327 | 2.73E-26 |
| CTGF | 3.338 | 5.65E-48 | TGFB1 | 2.660 | 5.39E-42 |
| EDN1 | 7.236 | 8.49E-28 | TGFBR1 | 2.257 | 2.86E-21 |
| EDNRA | -1.548 | 3.47E-17 | TGFBR2 | -1.579 | 3.68E-34 |
| EDNRB | -2.445 | 9.96E-11 | TNFRSF11B | -2.063 | 3.91E-12 |
| FGF1 | 3.778 | 9.42E-17 | TNFRSF1B | -5.364 | 4.95E-35 |
| FLT1 | -1.628 | 4.94E-08 | TNFSF10 | -3.807 | 6.07E-14 |
| HGF | -4.352 | 2.91E-181 | TNFSF18 | -2.908 | 1.92E-13 |
| ICAM1 | -3.363 | 6.64E-28 | VCAM1 | -4.582 | 6.15E-56 |
| IGF1 | 5.659 | 3.06E-23 | VEGFA | 1.598 | 9.18E-24 |

*Fig. 5C*

| Target | Log Ratio | p-value | Target | Log Ratio | p-value | Target | Log Ratio | p-value |
|---|---|---|---|---|---|---|---|---|
| EIF1 | 0.784 | 5.21E-04 | RPL28 | 1.869 | 1.81E-10 | RPLP2 | 1.694 | 5.38E-04 |
| EIF2S3 | 1.067 | 7.04E-03 | RPL29 | 1.589 | 3.21E-03 | RPS5 | 1.533 | 5.18E-03 |
| EIF3E | 1.469 | 2.87E-04 | RPL30 | 1.622 | 2.85E-03 | RPS6 | 1.598 | 5.99E-03 |
| EIF3F | 1.290 | 3.50E-03 | RPL31 | 1.600 | 7.78E-03 | RPS7 | 1.549 | 2.77E-03 |
| EIF3H | 1.329 | 2.47E-04 | RPL32 | 1.916 | 4.84E-04 | RPS8 | 1.611 | 4.90E-03 |
| EIF3L | 1.429 | 3.34E-03 | RPL34 | 1.608 | 2.48E-03 | RPS9 | 1.614 | 2.08E-03 |
| PABPC1 | 1.207 | 3.97E-04 | RPL36 | 1.411 | 3.67E-03 | RPS13 | 1.539 | 1.15E-03 |
| RPL3 | 1.780 | 7.43E-04 | RPL37 | 1.808 | 3.00E-03 | RPS14 | 1.684 | 3.99E-03 |
| RPL4 | 1.688 | 3.28E-03 | RPL38 | 1.353 | 6.96E-03 | RPS15 | 1.300 | 2.24E-04 |
| RPL5 | 1.593 | 3.92E-04 | RPL39 | 1.536 | 5.22E-03 | RPS16 | 1.989 | 8.68E-06 |
| RPL8 | 1.353 | 4.15E-03 | RPL41 | 1.474 | 7.12E-04 | RPS18 | 2.003 | 2.93E-03 |
| RPL9 | 1.613 | 5.38E-03 | RPL10A | 1.510 | 7.60E-03 | RPS19 | 1.550 | 5.37E-03 |
| RPL10 | 1.691 | 9.23E-04 | RPL13A | 1.797 | 4.22E-03 | RPS21 | 1.846 | 4.80E-04 |
| RPL11 | 1.396 | 5.38E-03 | RPL18A | 1.669 | 3.01E-03 | RPS24 | 1.444 | 3.41E-03 |
| RPL12 | 1.878 | 1.27E-03 | RPL22L1 | 1.012 | 4.48E-03 | RPS25 | 1.697 | 1.41E-03 |
| RPL14 | 1.745 | 1.25E-04 | RPL23A | 1.395 | 9.73E-03 | RPS26 | 1.090 | 8.58E-03 |
| RPL15 | 1.254 | 2.26E-03 | RPL27A | 2.090 | 2.38E-04 | RPS28 | 1.937 | 5.50E-05 |
| RPL18 | 1.612 | 2.08E-03 | RPL35A | 1.627 | 4.84E-04 | RPS29 | 1.571 | 7.82E-03 |
| RPL23 | 1.604 | 7.28E-03 | RPL36AL | 0.794 | 8.34E-03 | RPS15A | 2.195 | 1.84E-04 |
| RPL24 | 1.304 | 7.67E-03 | RPL37A | 2.029 | 1.12E-03 | RPS27A | 1.275 | 6.09E-03 |
| RPL26 | 1.655 | 7.91E-03 | RPL7A | 1.650 | 1.93E-03 | RPS4X | 1.534 | 8.76E-03 |
| RPL27 | 1.519 | 3.25E-03 | RPLP1 | 1.461 | 8.30E-03 | RPLP2 | 1.694 | 5.38E-04 |

*Fig. 6B*

COMPOSITIONS AND METHODS FOR TREATING FIBROTIC DISEASE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 300078_403WO_SEQUENCE_LISTING.txt. The text file is 2.3 KB, was created on Feb. 6, 2015, and is being submitted electronically via EFS-Web.

BACKGROUND

Progressive scarring (fibrosis) is a pathological feature of many chronic inflammatory diseases, and is an important cause of morbidity and mortality worldwide. Fibrosis is characterized by the accumulation of excess extracellular matrix components (e.g., collagen, fibronectin) that forms fibrous connective tissue in and around an inflamed or damaged tissue. Fibrosis may cause overgrowth, hardening, and/or scarring that disrupts the architecture of the underlying organ or tissue. While controlled tissue remodeling and scarring is part of the normal wound healing process promoted by transdifferentiation of fibroblasts into myofibroblasts, excessive and persistent scarring due to severe or repetitive injury or dysregulated wound healing (e.g., persistence of myofibroblasts) can eventually result in permanent scarring, organ dysfunction and failure, and even death.

Fibrotic changes can occur in vascular disorders (e.g., peripheral vascular disease, cardiac disease, cerebral disease) and in all main tissue and organ systems (e.g., lung, liver, kidney, heart, skin). Fibrotic disorders include a wide range of clinical presentations, including multisystemic disorders, such as systemic sclerosis, multifocal fibrosclerosis, and organ-specific disorders, such as pulmonary, liver, and kidney fibrosis (Rosenbloom et al., *Ann. Intern. Med.* 152: 159, 2010; Wynn, *Nat. Rev. Immunol.* 4:583, 2004). While the etiology and causative mechanisms of individual fibrotic disorders may vary (e.g., ischemic event, exposure to a chemical, radiation, or infectious agent) and are poorly understood, they all share the common feature of abnormal and excessive deposition of extracellular matrix in affected tissues (Wynn and Ramalingam, *Nat. Med.* 18:1028, 2012).

There are no effective therapies on the market today in the U.S. for treating or preventing fibrotic disorders. Current treatments generally target the inflammatory cascade that contribute to the progression of fibrosis and may temporarily improve symptoms, but are not effective in the long run (Wynn, 2004). Furthermore, the lack of biomarkers for assessing fibrosis progression or regression and therapeutic response has impeded rapid clinical screening of potential therapeutics (Schuppan and Pinzani, *J. Hepatol.* 56: S66, 2012; Castro and Jimenez, *Biomark Med.* 4:133, 2010).

There is clearly a need in the art for new, effective methods of treating or preventing fibrotic disorders and for identifying biomarkers for use in developing therapeutic agents and assessing therapeutic response. The present disclosure meets such needs, and further provides other related advantages.

BRIEF SUMMARY

In one aspect, the present disclosure provides a method for preventing, treating or ameliorating a fibrotic disease, comprising administering to a subject having a fibrotic disorder a therapeutically effective amount of a modulator specific for any one of the genes or encoded products listed in FIG. 7, Table 1, Table 3A, Table 3B, Table 5, Table 6, Table 7, an eIF2 component or regulator, an eIF4F complex or regulator, an eIF4F complex component or regulator, an eIF5A or regulator, or any combination thereof.

In other aspects, the present disclosure provides a method for reducing the risk of developing a fibrotic disease, comprising administering to a subject at risk of developing a fibrotic disorder a therapeutically effective amount of a modulator specific for any one of the genes or encoded products listed in FIG. 7, Table 1, Table 3A, Table 3B, Table 5, Table 6, Table 7, an eIF2 component or regulator, an eIF4F complex or regulator, an eIF4F complex component or regulator, an eIF5A or regulator, or any combination thereof.

In further aspects, the present disclosure provides a method for reducing myofibroblasts, comprising administering to a subject at risk of developing or having a fibrotic disorder a therapeutically effective amount of a modulator specific for any one of the genes or encoded products listed in FIG. 7, Table 1, Table 3A, Table 3B, Table 5, Table 6, Table 7, an eIF2 component or regulator, an eIF4F complex or regulator, an eIF4F complex component or regulator, an eIF5A or regulator, or any combination thereof.

In still further aspects, the present disclosure provides a method for inhibiting or reversing transdifferentiation of a fibroblast to a myofibroblast, comprising administering to a subject at risk of developing or having a fibrotic disorder a therapeutically effective amount of a modulator specific for any one of the genes or encoded products listed in FIG. 7, Table 1, Table 3A, Table 3B, Table 5, Table 6, Table 7, an eIF2 component or regulator, an eIF4F complex or regulator, an eIF4F complex component or regulator, an eIF5A or regulator, or any combination thereof.

BRIEF DESCRIPTION OF THE DRAWINGS

FIGS. 4A to 4C show schematics from Ingenuity Pathway Analysis (IPA) depicting the genes differentially regulated at the mRNA level in the hepatic fibrosis/hepatic stellate cell activation pathway. (A) Early signaling events in hepatic stellate cells. (B) Signaling events in activated hepatic stellate cells. Gene list used and gene signature identified in analysis is based on p-value from differential concentrations of protein-coding mRNAs from control and TGFβ treated fibroblasts. (C) Provides the list of differentially regulated genes from (A) and (B) and shows the magnitude of change (log ratio) and p-value for each gene in their respective pathway (results from 5 biological replicates).

FIGS. 5A to 5C show schematics from IPA depicting the translational rate differential regulation of genes in the hepatic fibrosis/hepatic stellate cell activation pathway. (A) Early signaling events in hepatic stellate cells. (B) Signaling events in activated hepatic stellate cells. Gene list used and gene signature identified in analysis is based on p-value from differential translation rates from control and TGFβ treated fibroblasts. (C) Provides the list of differentially regulated genes from (A) and (B) and shows the magnitude of change (log ratio) and p-value for each gene in their respective pathway. (results from 5 biological replicates).

FIGS. 6A and 6B show (A) a schematic from IPA depicting the genes regulated in the eIF2 signaling pathway. The gene list used in this analysis is based upon a p-value from differential translation efficiencies from control versus TGFβ-treated fibroblasts. (B) Provides the list of differentially regulated genes from (A) and shows the magnitude of change (log ratio) and p-value for each gene in their respective pathway (results from 5 biological replicates).

DETAILED DESCRIPTION

Figure 1:
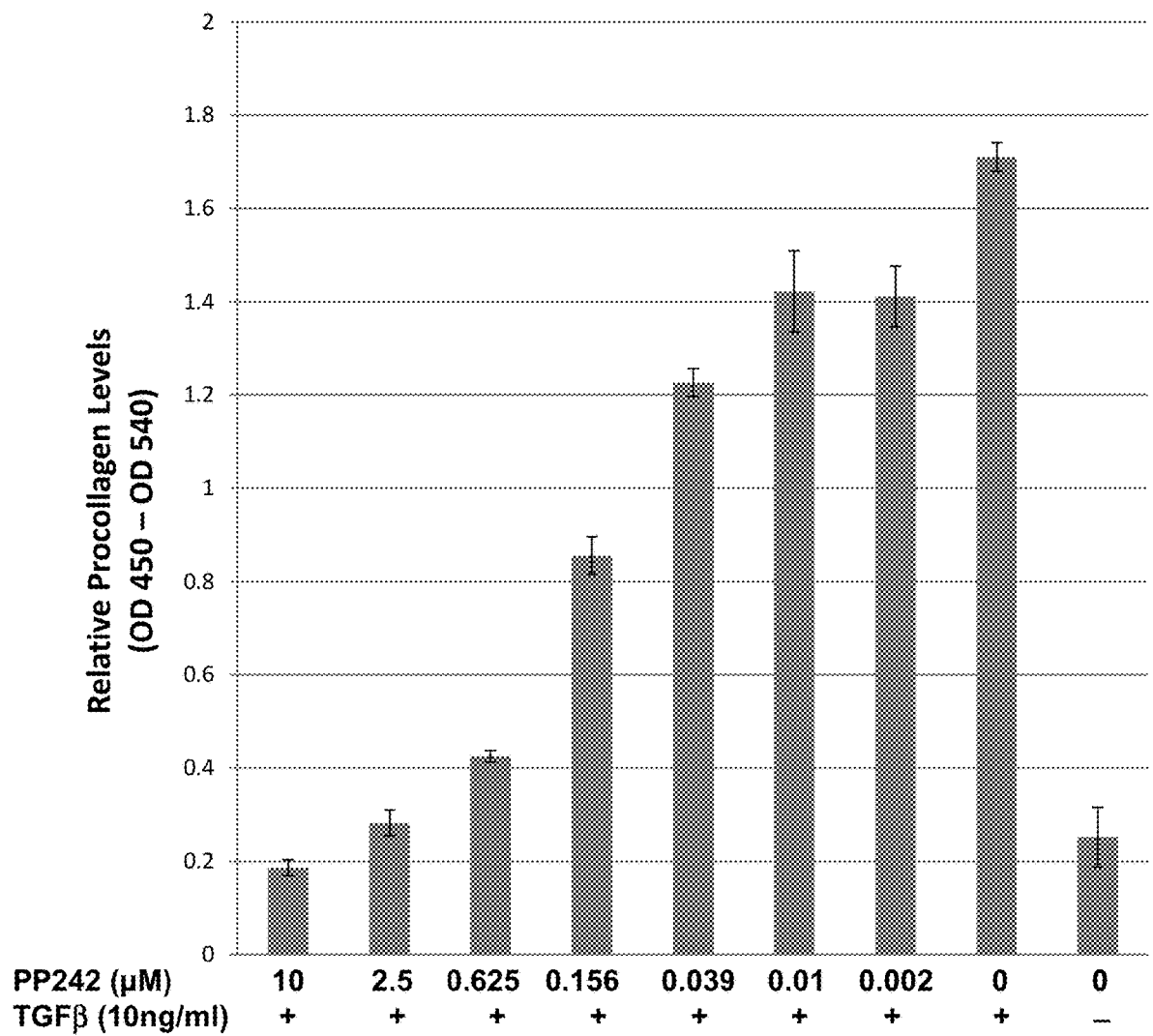
FIG. 1 shows the induction of procollagen secreted from fibroblasts by TGFβ. Procollagen type 1 levels (Procollagen Type 1C-Peptide, "PIPC") were measured after 24 hours of treating fibroblasts with various concentrations of mTOR inhibitor PP242 and 10 ng/mL TGFβ. The difference in absorbance at 450 and 540 nm (y-axis) is proportional to the procollagen concentration.

The instant disclosure provides compositions and methods for identifying agents and validating targets for preventing, ameliorating or treating a fibrotic disorder or disease. For example, translational profiles may be used to (a) identify a candidate therapeutic against an eIF2 pathway protein or regulator (e.g., eIF2 kinase, such as eIF2AK1), an eIF4F complex or component (e.g., eIF4A, eIF4E), an eIF5A protein or hypusination-related protein (e.g., deoxyhypusine synthase, DHPS; deoxyhypusine hydroxylase DOHH), or any combination thereof, for normalizing a translational profile associated with a fibrotic disease, (b) validate a target in or regulator of the eIF2 pathway, an eIF4F complex or component (e.g., eIF4A), or any combination thereof for normalizing a translational profile associated with a fibrotic disease, or (c) identify a subject having or at risk of developing a fibrotic disease as a candidate subject for treating or preventing the fibrotic disease with a therapeutic agent against an eIF2 pathway protein or regulator, an eIF4F complex or component (e.g., eIF4A), or any combination thereof.

By way of background, an injury is an event that damages tissue and initiates the wound healing process. After injury, both mechanical (i.e., extracellular stress caused by disruption of the extracellular matrix, ECM) and chemical signals (e.g., inflammatory mediators like TGFβ) activate fibroblastic cells to increase production of extra cellular matrix (ECM) components, which begins the process of fibroblast differentiation into myofibroblasts (Tomasek et al., *Nat. Rev. Mol. Cell Biol.* 3:349, 2002; Werner et al., *Physiol. Rev.* 83:835, 2003). Depending on the type of tissue being remodeled, the fibroblasts that differentiate may come from different sources, including locally present fibroblasts, pericytes, smooth muscle cells, fibrocytes from bone marrow, and from epithelial-mesenchymal transition (EMT) (Hinz et al., *Am. J. Pathol.* 170:1807, 2007). In early stages of differentiation, fibroblasts also increase production of focal adhesion proteins and form stress fibers (made up primarily of actin), which is considered a proto-myofibroblast phenotype (Tomasek et al., 2002). Further differentiation to the myofibroblast phenotype occurs when TGFβ accumulates, specialized ECM components are present (such as the ED-A variant of fibronectin), and extracellular stress from ECM and cell remodeling (Tomasek et al., 2002). A hallmark of myofibroblasts is the production of α-smooth muscle actin (α-SMA) (Hinz, *J. Invest. Dermatol.* 127:526, 2007). Wound healing is complete when the newly formed, cross-linked ECM takes over the mechanical load, which is a signal to myofibroblasts to undergo apoptosis (Tomasek et al., 2002; Carlson et al., *J. Surg. Res.* 110:304, 2003).

If the injury is severe or repetitive, or if the wound-healing process is dysregulated, fibrosis becomes pathogenic, resulting in permanent scarring or hardening of the tissue, organ malfunction or failure, and ultimately death. For example, idiopathic pulmonary fibrosis (IPF) is a poorly understood progressive and fatal lung disease that has no effective treatment other than lung transplantation (Mason et al., *Ann. Thorac. Surg.* 84:1121-8, 2007). Median survival of five years after diagnosis is less than 20%. Most forms of interstitial lung diseases and other forms of pulmonary fibrosis are characterized by fibrotic lesions, progressive distortion of alveolar architecture occurs and replacement with fibrotic or scar tissues with excess ECM deposition (American Thoracic Society, *Am. J. Respir. Crit. Care Med.* 161:646, 2000; Noble et al., *Clin. Chest Med.* 25:749, 2004; Selman et al., *Ann. Intern. Med.* 134:136, 2001). This results in progressive dyspnea and loss of lung function. A hallmark morphological lesion is spatial and temporal heterogeneity incorporating areas of normal lung being directly adjacent to areas of fully established fibrosis, microscopic honeycombing, and areas of evolving fibrosis containing collagen-producing fibroblasts/myofibroblasts, often referred to as "fibrotic foci." Myofibroblasts are present in abundance within fibrotic lesions and, therefore, contribute to the excessive scarring found in such lesions of fibrotic disease (Gabbiani, *J. Pathol.* 200:500, 2003).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, the term "translational profile" refers to the amount of protein that is translated (i.e., translational level) for each gene in a given set of genes in a biological sample, collectively representing a set of individual translational rate values, translational efficiency values, or both translational rate and translational efficiency values for each of one or more genes in a given set of genes. In some embodiments, a translational profile comprises translational levels for a plurality of genes in a biological sample (e.g., cells), e.g., for at least about 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000 genes or more, or for at least about 1%, 2%, 3%, 4%, 5%, 6%, 7%, 8%, 9%, 10%, 15%, 20%, 25%, 50% or more of all genes in the sample. In some embodiments, a translational profile comprises a genome-wide measurement of translational rate, translational efficiency or both in a biological sample. In certain embodiments, a translational profile refers to a quantitative measure of the amount of mRNA associated with one or more ribosomes for each gene (i.e., translational rate, efficiency or both) in a given set of genes in a biological sample, wherein the amount of ribosome-associated mRNA correlates to the amount of protein that is translated (i.e., translational level).

As used herein, "translation rate" or "rate of translation" or "translational rate" refers to the total count of ribosome engagement, association or occupancy of mRNA for a particular gene as compared to the total count of ribosome engagement, association or occupancy of mRNA for at least one other gene or set of genes, wherein the count of total ribosomal occupancy correlates to the level of protein synthesis. Examination of translation rate across individual genes may be quantitative or qualitative, which will reveal differences in translation. In certain embodiments, translational rate provides a measure of protein synthesis for one or more genes, a plurality of genes, or across an entire genome. In particular embodiments, a translation rate is the amount of mRNA fragments protected by ribosomes for a particular gene relative to the amount of mRNA fragments protected by ribosomes for one or more other genes or groups of genes. For example, the mRNA fragments protected by ribosomes may correspond to a portion of the 5'-untranslated region, a portion of the coding region, a portion of a splice variant coding region, or combinations thereof. In further embodiments, the translation rate is a measure of one, a plurality or all mRNA variants of a particular gene. Translation rates can be established for one or more selected genes or groups of genes within a single composition (e.g., biological sample), between different compositions, or between a composition that has been split into at least two portions and each portion exposed to different conditions.

As used herein, "mRNA level" refers to the amount, abundance, or concentration of mRNA or portions thereof for a particular gene in a composition (e.g., biological sample). In certain embodiments, mRNA level refers to a count of one mRNA, a plurality of mRNA or all mRNA forms or fragments for a particular gene, including pre-mRNA, mature mRNA, or splice variants thereof. In particular embodiments, an mRNA level for one or more genes or groups of genes corresponds to counts of unique mRNA sequences or portions thereof for a particular gene that map to a 5'-untranslated region, a coding region, a splice variant coding region, or any combination thereof.

As used herein, "translation efficiency" or "translational efficiency" refers to the ratio of the translation rate for a particular gene to the mRNA level for a particular gene in a given set of genes. For example, gene X may produce an equal abundance of mRNA (i.e., same or similar mRNA level) in normal and diseased tissue, but the amount of protein X produced may be greater in diseased tissue as compared to normal tissue. In this situation, the message for gene X is more efficiently translated in diseased tissue than in normal tissue (i.e., an increased translation rate without an increase in mRNA level). In another example, gene Y may produce half the mRNA level in normal tissue as compared to diseased tissue, and the amount of protein Y produced in normal tissue is half the amount of protein Y produced in diseased tissue. In this second situation, the message for gene Y is translated equally efficiently in normal and diseased tissue (i.e., a change in translation rate in diseased tissue that is proportional to the increase in mRNA level and, therefore, the translational efficiency is unchanged). In other words, the expression of gene X is altered at the translational level, while gene Y is altered at the transcriptional level. In certain situations, both the amount of mRNA and protein may change such that mRNA abundance (transcription), translation rate, translation efficiency, or a combination thereof is altered relative to a particular reference or standard.

In certain embodiments, translational efficiency may be standardized by measuring a ratio of ribosome-associated mRNA read density (i.e., translation level) to mRNA abundance read density (i.e., transcription level) for a particular gene (see, e.g., Example 3). As used herein, "read density" is a measure of mRNA abundance and protein synthesis (e.g., ribosome profiling reads) for a particular gene, wherein at least 5, 10, 15, 20, 25, 50, 100, 150, 175, 200, 225, 250, 300 reads or more per unique mRNA or portion thereof is performed in relevant samples to obtain single-gene quantification for one or more treatment conditions. In certain embodiments, translational efficiency is scaled to standardize or normalize the translational efficiency of a median gene to 1.0 after excluding regulated genes (e.g., $\log_2$ fold-change $\pm 1.5$ after normalizing for the all-gene median), which corrects for differences in the absolute number of sequencing reads obtained for different libraries. In further embodiments, changes in protein synthesis, mRNA abundance and translational efficiency are similarly computed as the ratio of read densities between different samples and normalized to give a median gene a ratio of 1.0, normalized to the mean, normalized to the mean or median of log values, or the like.

Figure 6A:
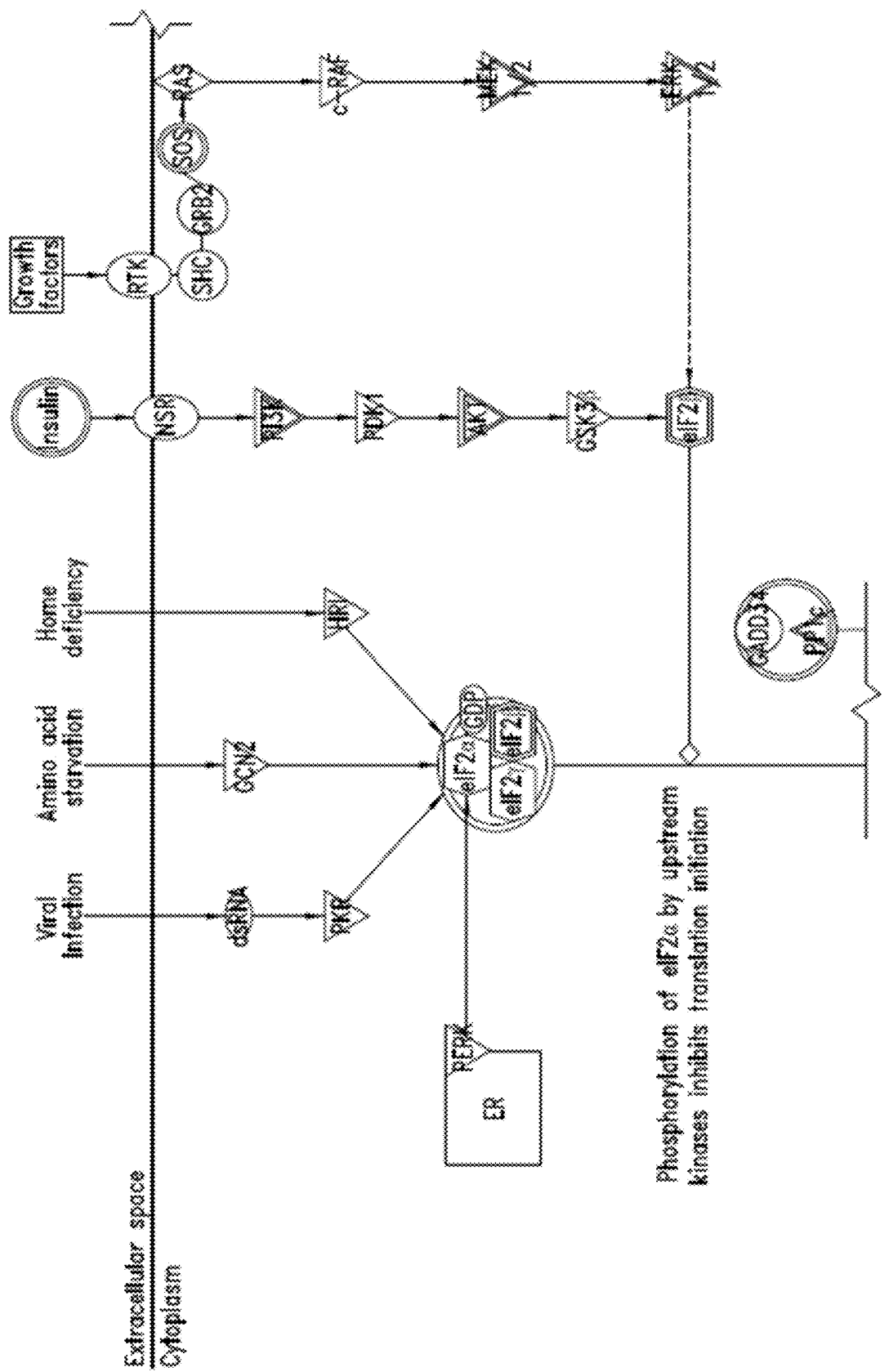
Figure 6A:
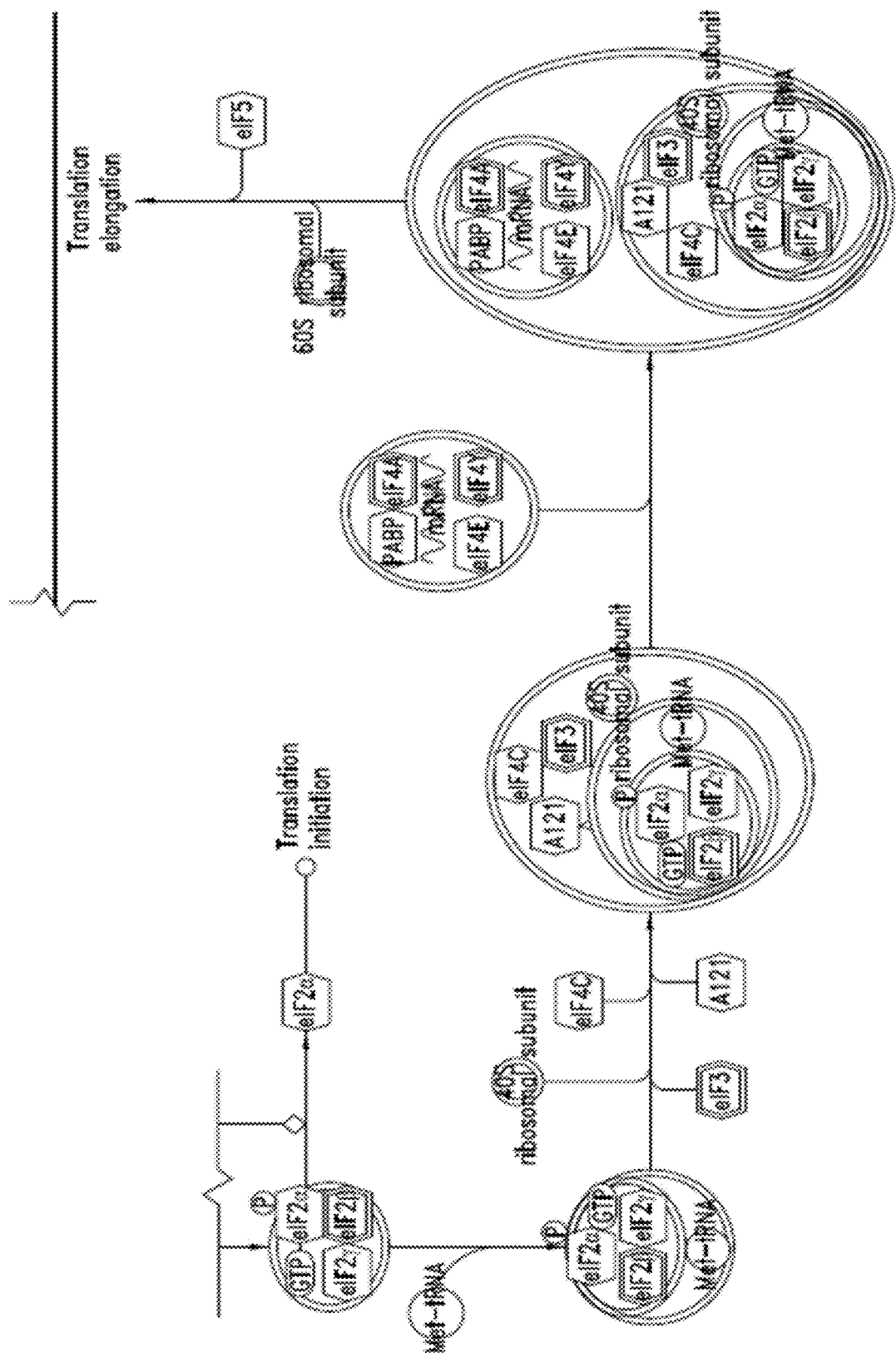
Figure 7:
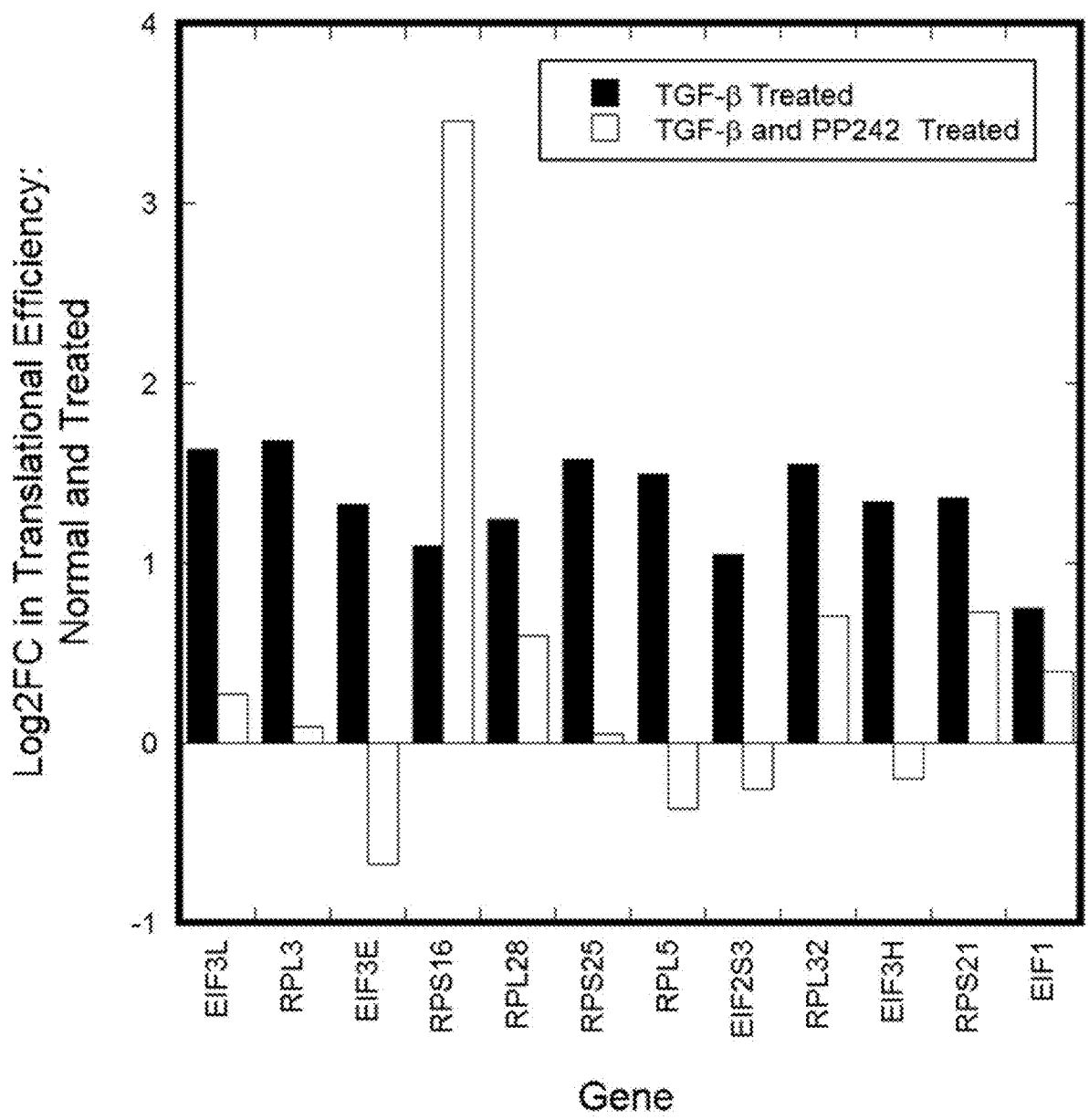
FIG. 7 shows the normalization of translational efficiencies of fibrotic disorder-associated gene signature in the eIF2 signaling pathway. The bar graph shows the translational efficiencies of fibrotic disorder-associated gene signature in fibroblasts treated with TGFβ and fibroblasts treated with TGFβ and PP242. The normal fibroblast translational efficiency is set at zero, and each of the 12 genes shown had an altered translational efficiency in TGFβ-treated fibroblasts (p-value ≤0.05), which is a representative result from a single experimental replicate.

As used herein, "gene signature" refers to a plurality of genes that exhibit a generally coherent, systematic, coordinated, unified, collective, congruent, or signature expression pattern or translation efficiency. In certain embodiments, a gene signature is (a) a plurality of genes that together comprise at least a detectable or identifiable portion of a biological pathway (e.g., 2, 3, 4, 5, or more genes; a fibrotic disease gene signature comprising 11 or 12 genes from the eIF2 translation pathway as illustrated in FIGS. 6 and 7, or a plurality of genes regulated by the eIF4F complex or component thereof, such as eIF4A), (b) a complete set of genes associated with a biological pathway, or (c) a cluster or grouping of independent genes having a recognized pattern of expression (e.g., response to a known drug or active compound; related to a disease state such as a fibrotic disorder). One or more genes from a particular gene signature may be part of a different gene signature (e.g., a cell migration pathway may share a gene with a cell adhesion pathway)—that is, gene signatures may intersect or overlap but each signature can still be independently defined by its unique translation profile.

The term "modulate" or "modulator," as used with reference to altering an activity of a target gene or signaling pathway, refers to increasing (e.g., activating, facilitating, enhancing, agonizing, sensitizing, potentiating, or up regulating) or decreasing (e.g., preventing, blocking, inactivating, delaying activation, desensitizing, antagonizing, attenuating, or down regulating) the activity of the target gene or signaling pathway. In certain embodiments, a modulator alters a translational profile at the translational level (i.e., increases or decreases translation rate, translation efficiency or both, as described herein), at the transcriptional level, or both.

As used herein, a modulator or agent that "specifically binds" or is "specific for" a target refers to an association or union of a modulator or agent (e.g., siRNA, chemical compound) to a target molecule (e.g., a nucleic acid molecule encoding a target, a target product encoded by a nucleic acid molecule, or a target activity), which may be a covalent or non-covalent association, while not significantly associating or uniting with any other molecules or components in a cell, tissue, biological sample, or subject. A modulator or agent specific for a target (e.g., translation machinery component, such as eIF2, eIF4A, eIF4E, eIF5A; translation machinery regulator, such as eIF2AK1, eIF2AK2, eIF2AK3, eIF2AK4, DHPS, DOHH) includes analogs and derivatives thereof. In certain embodiments, a modulator specific for a translation machinery component (e.g., eIF4A, eIF5A) or translation machinery regulator (e.g., eIF2AK1, DOHH) is a siRNA molecule.

As used herein, the term "derivative" refers to a modification of a compound by chemical or biological means, with or without an enzyme, which modified compound is structurally similar to a parent compound and (actually or theoretically) derivable from that parent compound. Generally, a "derivative" differs from an "analog" in that a parent compound may be the starting material to generate a "derivative," whereas the parent compound may not necessarily be used as the starting material to generate an "analog." An analog or derivative may have different chemical, biological or physical properties from the parent compound, such as being more hydrophilic or having altered reactivity. Derivatization (i.e., modification) may involve substitution of one or more moieties of a molecule (e.g., a change in functional group). For example, a hydrogen may be substituted with a halogen, such as fluorine or chlorine, or a hydroxyl group (—OH) may be replaced with a carboxylic acid moiety (—COOH). Other exemplary derivatizations include glycosylation, alkylation, acylation, acetylation, ubiquitination, esterification, and amidation.

The term "derivative" also refers to all solvates, for example, hydrates or adducts (e.g., adducts with alcohols), active metabolites, and salts of a parent compound. The type of salt depends on the nature of the moieties within the compound. For example, acidic groups, such as carboxylic acid groups, can form alkali metal salts or alkaline earth metal salts (e.g., sodium salts, potassium salts, magnesium salts, calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts with, for example, inorganic acids such as hydrochloric acid, sulfuric acid or phosphoric acid, or with organic carboxylic acids or sulfonic acids such as acetic acid, citric acid, lactic acid, benzoic acid, maleic acid, fumaric acid, tartaric acid, methanesulfonic acid or p-toluenesulfonic acid. Compounds that simultaneously contain a basic group and an acidic group, for example, a carboxyl group in addition to basic nitrogen atoms, can be present as zwitterions. Salts can be obtained by customary methods known to those skilled in the art, for example, by combining a compound with an inorganic or organic acid or base in a solvent or diluent, or from other salts by cation exchange or anion exchange.

In some embodiments, an agent that modulates translation in a fibrotic disease is identified as suitable for use when one or more genes of one or more biological pathways, gene signatures or combinations thereof are differentially translated by at least 1.5-fold (e.g., at least 1.5-fold, at least 2-fold, at least 2.5-fold, at least 3-fold, at least 3.5-fold, at least 4-fold, at least 4.5-fold, at least 5-fold, at least 6-fold, at least 7-fold, at least 8-fold, at least 9-fold, at least 10-fold or more) in a first translational profile (e.g., treated fibrotic disease sample or normal sample) as compared to a second translational profile (e.g., untreated fibrotic disease sample). In some embodiments, an agent that modulates translation in a fibrotic disease is identified as suitable for use when the translational rate, translational efficiency or both for one or more genes of one or more biological pathways, gene signatures or combinations thereof are increased or decreased by at least 1.5-fold (e.g., at least 1.5-fold, at least 2-fold, at least 2.5-fold, at least 3-fold, at least 3.5-fold, at least 4-fold, at least 4.5-fold, at least 5-fold, at least 6-fold, at least 7-fold, at least 8-fold, at least 9-fold, at least 10-fold or more) in a first translational profile as compared to a second translational profile.

A "biological sample" includes blood and blood fractions or products (e.g., serum, plasma, platelets, red blood cells, or the like); sputum or saliva; kidney, lung, liver, heart, brain, nervous tissue, thyroid, eye, skeletal muscle, cartilage, or bone tissue; cultured cells, e.g., primary cultures, explants, and transformed cells, stem cells, stool, urine, etc. Such biological samples (e.g., disease samples or normal samples) also include sections of tissues, such as a biopsy or autopsy sample, frozen sections taken for histologic purposes, or cells or other biological material used to model disease or to be representative of a pathogenic state (e.g., TGFβ treated fibroblasts as a model system for fibrosis). In certain embodiments, a biological sample is obtained from a "subject," e.g., a eukaryotic organism, most preferably a mammal such as a primate, e.g., chimpanzee or human; cow; dog; cat; rodent, e.g., guinea pig, rat, or mouse; rabbit; bird; reptile; or fish.

As used herein, the term "normalize" or "normalizing" or "normalization" refers to adjusting the translational rate, translational efficiency, or both of one or more genes in a biological sample from a subject (e.g., a disease sample from one or more subjects, tissues or organs) to a level that is more similar, closer to, or comparable to the translational rate, translational efficiency, or both of those same one or more genes in a control sample (e.g., a non-diseased or normal sample from the same or different subject, tissue or organ). In certain embodiments, normalization refers to modulation of one or more translational regulators or translational system components to adjust or shift the translational rate, efficiency or both of one or more genes in a biological sample (e.g., diseased, abnormal or other biologically altered condition) to a translational efficiency that is more similar, closer to or comparable to the translational efficiency of those one or more genes in a non-diseased or normal control sample. In some embodiments, normalization is evaluated by determining a translational rate, translational efficiency or both of one or more genes in a biological sample (e.g., disease sample) from a subject before and after an agent (e.g., therapeutic or known active agent) is administered to the subject and comparing the translational rate, translational efficiency or both before and after administration to the translational rate, translational efficiency or both from a control sample in the absence or presence of the agent. Exemplary methods of evaluating normalization of a translational profile associated with a disease or disorder includes observing a shift in a gene signature or evaluating a translational profile shift due to a therapeutic intervention in a fibrotic or fibrotic-associated condition, disease or disorder.

As used herein, the phrase "differentially translated" refers to a change or difference (e.g., increase, decrease or a combination thereof) in translation rate, translation efficiency, or both of one gene, a plurality of genes, a set of genes of interest, one or more gene clusters, or one or more gene signatures under a particular condition as compared to the translation rate, translation efficiency, or both of the same gene, plurality of genes, set of genes of interest, gene clusters, or gene signatures under a different condition, which is observed as a difference in expression pattern. For example, a translational profile of a diseased cell may reveal that one or more genes have higher translation rates, higher translation efficiencies, or both (e.g., higher ribosome engagement of mRNA or higher protein abundance) than observed in a control or normal cell. Another exemplary translational profile of a diseased cell may reveal that one or more genes have lower translation rates, lower translation efficiencies, or both (e.g., lower ribosome engagement of mRNA or lower protein abundance) than observed in a control or normal cell. In still another example, a translational profile of a diseased cell may reveal that one or more genes have higher translation rates, one or more genes have higher translation efficiencies, one or more genes have lower translation rates, one or more genes have lower translation efficiencies, or any combination thereof than observed in a control or normal cell. In some embodiments, one or more gene signatures, gene clusters or sets of genes of interest are differentially translated in a first translational profile as compared to one or more other translational profiles. In further embodiments, one or more genes, gene signatures, gene clusters or sets of genes of interest in a first translational profile show at least a 1.5-fold translation differential or at least a 1.0 $\log_2$ change (i.e., increase or decrease) as compared to the same one or more genes in at least one other different (e.g., second, third, etc.) translational profile.

In some embodiments, two or more translational profiles are generated and compared to each other to determine the differences (i.e., increases and/or decreases in translational rate, translational efficiency, or both) for each gene in a given set of genes between the two or more translational profiles. The comparison between the two or more translational profiles is referred to as the "differential translational profile." In certain embodiments, a differential translational profile comprises one or more genes, gene clusters, or gene signatures (e.g., a fibrotic disease-associated pathway), or combinations thereof.

In certain embodiments, differential translation between genes or translational profiles may involve or result in a biological (e.g., phenotypic, physiological, clinical, therapeutic, prophylactic) benefit. For example, when identifying a therapeutic, validating a target, or treating a subject having a fibrotic disorder or disease, a "biological benefit" means that the effect on translation rate, translation efficiency or both, or the effect on the translation rate, translation efficiency or both of one or more genes of a translational profile allows for intervention or management of the fibrotic disorder or disease of a subject (e.g., a human or non-human mammal, such as a primate, horse, dog, mouse, rat). In general, one or more differential translations or differential translation profiles indicate that a "biological benefit" will be in the form, for example, of an improved clinical outcome; lessening or alleviation of symptoms associated with fibrotic disease; decreased occurrence of symptoms; improved quality of life; longer disease-free status; diminishment of extent of fibrotic disease; stabilization of a fibrotic disease; delay of fibrotic disease progression; remission; survival; or prolonging survival. In certain embodiments, a biological benefit comprises normalization of a differential translation profile, or comprises a shift in translational profile to one closer to or comparable to a translational profile induced by a known active compound or therapeutic, or comprises inducing, stimulating or promoting a desired phenotype or outcome (e.g., reversal of transformation, induction of a quiescent state, apoptosis, necrosis, cytotoxicity), or reducing, inhibiting or preventing an undesired phenotype or outcome (e.g., activation, transformation, proliferation, migration).

In some embodiments, a biological benefit comprises reducing the amount of myofibroblast cells associated with a fibrotic disorder or disease by reducing, blocking or reversing transdifferentiation of fibroblast cells into myofibroblast cells, or by promoting apoptosis, senescence or quiescence of myofibroblast cells. In further embodiments, a biological benefit comprises inhibiting or blocking the production, secretion or both of organ damaging (i.e., toxic in a fibrotic disorder) proteins produced by myofibroblasts (e.g., ECM related proteins) in a subject having a fibrotic disorder or disease. As used herein, the phrase "organ damaging proteins" refers to one or more proteins associated with myofibroblasts in the context of a fibrotic disorder under these circumstances can be toxic, whereas such proteins under normal conditions would not be organ damaging.

In some embodiments, less than about 20% of the genes in the genome are differentially translated by at least 1.5-fold in a first translational profile as compared to a second translational profile. In some embodiments, less than about 5% of the genes in the genome are differentially translated by at least 2-fold or at least 3-fold in a first translational profile as compared to a second translational profile. In some embodiments, less than about 1% of the genes in the genome are differentially translated by at least 4-fold or at least 5-fold in a first translational profile as compared to a second translational profile.

As described herein, differentially translated genes between first and second translational profiles under a first condition may exhibit translational profiles "closer to" each other (i.e., identified through a series of pair-wise comparisons to confirm a similarity of pattern) under one or more different conditions (e.g., differentially translated genes between a normal sample and a fibrotic disease sample may have a more similar translational profile when the normal sample is compared to a fibrotic disease sample contacted with a candidate agent; differentially translated genes between a fibrotic disease sample and a fibrotic disease sample treated with a known active agent may have a more similar translational profile when the disease sample treated with a known active agent is compared to the disease sample contacted with a candidate agent). In certain embodiments, a test translational profile is "closer to" a reference translational profile when at least 99%, 95%, 90%, 80%, 70%, 60%, 50%, 25%, or 10% of a selected portion of differentially translated genes, a majority of differentially translated genes, or all differentially translated genes show a translational profile within 75%, 70%, 65%, 60%, 55%, 50%, 45%, 40%, 35%, 30%, or 25%, respectively, of their corresponding genes in the reference translational profile. In further embodiments, a selected portion of differentially translated genes, a majority of differentially translated genes, or all differentially translated genes from an experimental translational profile have a translational profile "closer to" the translational profile of the same genes in a reference translational profile when the amount of protein translated in the experimental and reference translational profiles are within about 3.0 $\log_2$, 2.5 $\log_2$, 2.0 $\log_2$, 1.5 $\log_2$, 1.1 $\log_2$, 0.5 $\log_2$, 0.2 $\log_2$ or closer. In still further embodiments, a selected portion of differentially translated genes, a majority of differentially translated genes, or all differentially translated genes from an experimental translational profile have a translational profile "closer to" the translational profile of the same genes in a reference translational profile when the amount of protein translated in the experimental and reference translational profiles differs by no more than about 50%, 45%, 40%, 35%, 30%, 25%, 20%, 15%, 10%, 5%, 1% or less.

In some embodiments, an experimental differential profile as compared to a reference differential translational profile of interest has at least a 1.0 $\log_2$ change in translational rate, translational efficiency, or both for at least 0.05%, at least 0.1%, at least 0.25%, at least 0.5%, at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, at least 60%, at least 70%, at least 80%, or at least 90% or more of a set of selected differentially translated genes or for the entire set of selected differentially translated genes. In some embodiments, an experimental differential profile as compared to a reference differential translational profile of interest has at least a 2 $\log_2$ change in translational rate, translational efficiency, or both for at least 0.05%, at least 0.1%, at least 0.25%, at least 0.5%, at least 1%, at least 5%, at least 10%, at least 15%, at least 20%, at least 30%, at least 40%, at least 50%, at least 60%, at least 70%, at least 80%, or at least 90% or more of a set of selected differentially translated genes or for the entire set of differentially translated genes. In some embodiments, an experimental differential profile as compared to a reference differential translational profile of interest has at least a 3 $\log_2$ change in translational rate, translational efficiency, or both for at least 0.05%, at least 0.1%, at least 0.25%, at least 0.5%, at least 1%, at least 5%, at least 10%, at least 15%, at least 20%, at least 30%, at least 40%, at least 50%, at least 60%, at least 70%, at least 80%, or at least 90% or more of a set of selected differentially translated genes or for the entire set of selected differentially translated genes. In some embodiments, an experimental differential profile as compared to a reference differential translational profile of interest has at least a 4 $\log_2$ change in translational levels for at least 0.05%, at least 0.1%, at least 0.25%, at least 0.5%, at least 1%, at least 5%, at least 10%, at least 15%, at least 20%, at least 30%, at least 40%, at least 50%, at least 60%, at least 70%, at least 80%, or at least 90% or more of a set of selected differentially translated genes or for the entire set of selected differentially translated genes.

As described herein, a differential translational profile between a first sample and a control may be "comparable" to a differential translational profile between a second sample and the control (e.g., the differential profile between a fibrotic disease sample and the fibrotic disease sample treated with a known active compound may be comparable to the differential profile between the fibrotic disease sample and the fibrotic disease sample contacted with a candidate agent; the differential profile between a fibrotic disease sample and a non-diseased (normal) sample may be comparable to the differential profile between the fibrotic disease sample and the fibrotic disease sample contacted with a candidate agent). In certain embodiments, a test differential translational profile is "comparable to" a reference differential translational profile when at least 99%, 95%, 90%, 80%, 70%, 60%, 50%, 25%, or 10% of a selected portion of differentially translated genes, a majority of differentially translated genes, or all differentially translated genes show a translational profile within 75%, 70%, 65%, 60%, 55%, 50%, 45%, 40%, 35%, 30%, or 25%, respectively, of their corresponding genes in the reference translational profile. In further embodiments, a differential translational profile comprising a selected portion of the differentially translated genes or all the differentially translated genes has a differential translational profile "comparable to" the differential translational profile of the same genes in a reference differential translational profile when the amount of protein translated in the experimental and reference differential translational profiles are within about 3.0 $\log_2$, 2.5 $\log_2$, 2.0 $\log_2$, 1.5 $\log_2$, 1.0 $\log_2$, 0.5 $\log_2$, 0.2 $\log_2$ or closer. In still further embodiments, a differential translational profile comprising a selected portion of the differentially translated genes or all the differentially translated genes has a differential translational profile "comparable to" the differential translational profile of the same genes in a reference differential translational profile when the amount of protein translated in the experimental and reference differential translational profiles differs by no more than about 50%, 45%, 40%, 35%, 30%, 25%, 20%, 15%, 10%, 5%, 1% or less.

As used herein, "fibroblast" refers to a mesenchymal-derived connective tissue cell that secretes extracellular matrix components, such as collagen, and other macromolecules. Fibroblasts have a spindle-shaped morphology and can play a role in organismal development and wound healing. For example, fibroblasts may be identified by global DNase I hypersensitive site mapping which establishes a lineage association (Stamatoyannopoulos et al., Nat. Genet. 43:264, 2011), or by the production of certain biomarkers (e.g., Discoidin Domain Receptor 2, DDR2 and vimentin). Fibroblasts are different from endothelial cells and hematopoietic cells.

The term "fibrotic disorder" or "fibrotic disease" refers to a medical condition featuring progressive and/or irreversible fibrosis, wherein excessive deposition of extracellular matrix occurs in and around inflamed or damaged tissue. In certain embodiments, a fibrotic disorder or disease is associated with the persistent presence of myofibroblasts in and around fibrotic foci or lesions. Excessive and persistent fibrosis can progressively remodel and destroy normal tissue, which may lead to dysfunction and failure of affected organs, and ultimately death. A fibrotic disorder may affect any tissue in the body and is generally initiated by an injury and the transdifferentiation of fibroblasts into myofibroblasts. As used herein, "transdifferentiation" refers to the direct conversion of one cell type into another. It is to be understood that fibrosis alone triggered by normal wound healing processes that has not progressed to a pathogenic state is not considered a fibrotic disorder or disease of this disclosure. A "fibrotic lesion" or "fibrotic plaque" refers to a focal area of fibrosis.

As used herein, "injury" refers to an event that damages tissue and initiates fibrosis. An injury may be caused by an external factor, such as mechanical insult (e.g., cut, surgery), exposure to radiation, chemicals (e.g., chemotherapy, toxins, irritants, smoke), or infectious agent (e.g., bacteria, virus, or parasite). An injury may be caused by, for example, chronic autoimmune inflammation, allergic response, HLA mismatching (e.g., transplant recipients), or ischemia (i.e., an "ischemic event" or "ischemia" refers to an injury that restricts in blood supply to a tissue, resulting in damage to or dysfunction of tissue, which may be caused by problems with blood vessels, atherosclerosis, thrombosis or embolism, and may affect a variety of tissues and organs; an ischemic event may include, for example, a myocardial infarction, stroke, organ or tissue transplant, or renal artery stenosis). In certain embodiments, an injury leading to a fibrotic disorder may be of unknown etiology (i.e., idiopathic).

Non-limiting examples of fibrotic disorders or fibrotic diseases include pulmonary fibrosis, idiopathic pulmonary fibrosis, cystic fibrosis, liver fibrosis (e.g., cirrhosis), cardiac fibrosis, endomyocardial fibrosis, vascular fibrosis (e.g., atherosclerosis, stenosis, restenosis), atrial fibrosis, mediastinal fibrosis, myelofibrosis, retroperitoneal fibrosis, progressive massive fibrosis (e.g., lungs), chronic kidney disease, nephrogenic systemic fibrosis, Crohn's disease, hypertrophic scarring, keloid, scleroderma, systemic sclerosis (e.g., skin, lungs), athrofibrosis (e.g., knee, shoulder, other joints), Peyronie's disease, Dupuytren's contracture, adhesive capsulitis, organ transplant associated fibrosis, ischemia associated fibrosis, or the like.

Reference to "pulmonary fibrotic disorder" means diseases or disorders characterized by fibrotic hypertrophy or fibrosis of lung tissue. Exemplary pulmonary fibrotic disorders include pulmonary fibrosis, idiopathic pulmonary fibrosis, interstitial lung disease, interstitial pulmonary fibrosis, chronic interstitial pneumonitis, Hamman-Rich Syndrome, usual interstitial pneumonitis (UIP), fibrosing alveolitis, pulmonary sarcoidosis, progressive massive fibrosis (e.g., lungs), systemic sclerosis (e.g., lungs), lung transplant associated fibrosis, or the like.

"Treatment," "treating" or "ameliorating" refers to medical management of a disease, disorder, or condition of a subject (i.e., patient), which may be therapeutic, prophylactic/preventative, or a combination treatment thereof. A treatment may improve or decrease the severity at least one symptom of fibrotic disease, delay worsening or progression of a disease, delay or prevent onset of additional associated diseases, or improve remodeling of fibrotic lesions into functional (partially or fully) tissue. "Reducing the risk of developing a fibrotic disorder" refers to preventing or delaying onset of a fibrotic disorder or reoccurrence of one or more symptoms of the fibrotic disorder.

A "therapeutically effective amount (or dose)" or "effective amount (or dose)" of a compound refers to that amount sufficient to result in amelioration of one or more symptoms of the disease being treated in a statistically significant manner. When referring to an individual active ingredient administered alone, a therapeutically effective dose refers to that ingredient alone. When referring to a combination, a therapeutically effective dose refers to combined amounts of the active ingredients that result in the therapeutic effect, whether administered serially or simultaneously.

The term "pharmaceutically acceptable" refers to molecular entities and compositions that do not produce allergic or other serious adverse reactions when administered to a subject using routes well-known in the art.

A "subject in need" refers to a subject at risk of, or suffering from, a disease, disorder or condition (e.g., fibrosis) that is amenable to treatment or amelioration with a compound or a composition thereof provided herein. In certain embodiments, a subject in need is a human.

The "percent identity" between two or more nucleic acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, p. 10; Lehninger, Biochemistry, $2^{nd}$ Edition; Worth Publishers, Inc. NY:N.Y. (1975), pp. 71- 77; Lewin, Genes IV, Oxford University Press, NY and Cell Press, Cambridge, Mass. (1990), p. 8).

Fibrotic Disorder or Disease

In one aspect, the present disclosure provides a method for preventing, treating or ameliorating a fibrotic disorder, comprising administering to a subject having a fibrotic disorder a therapeutically effective amount of a modulator specific for any one or more of the genes (including any alleles, homologs, or orthologs) or any encoded products (including any active fragments or splice variants thereof) listed in FIG. 7, Table 1, Table 3A, Table 3B, Table 5, Table 6, Table 7, an eIF2 component or regulator, an eIF4F complex, an eIF4F complex component (such as eIF4A or eIF4E) or regulator, or an eIF5A or regulator (such as DHPS or DOHH). In certain embodiments, the present disclosure provides a method for reducing the risk of developing a fibrotic disorder, comprising: administering to a subject at risk of developing a fibrotic disorder a therapeutically effective amount of a modulator specific for any one or more of the genes (including any alleles, homologs, or orthologs) or any encoded products (including any active fragments or splice variants thereof) listed in FIG. 7, Table 1, Table 3A, Table 3B, Table 5, Table 6, Table 7, an eIF2 component or regulator (such as eIF2AK1, eIF2AK2, eIFAK3 or eIFAK4), an eIF4F complex, an eIF4F complex component (such as eIF4A or eIF4E) or regulator, an eIF5A or regulator (such as DHPS or DOHH).

In other aspects, the present disclosure provides a method for reducing myofibroblasts, comprising administering to a subject at risk of developing or having a fibrotic disorder a therapeutically effective amount of a modulator specific for any one of the genes (including any alleles, homologs, or orthologs) or any encoded products (including any active fragments or splice variants thereof) listed in FIG. 7, Table 1, Table 3A, Table 3B, Table 5, Table 6, Table 7, an eIF2 component or regulator, an eIF4F complex or regulator, an eIF4F complex component or regulator, an eIF5A or regulator, or any combination thereof.

In still other aspects, the present disclosure provides a method for inhibiting or reversing fibroblast transdifferentiation into a myofibroblast, comprising administering to a subject at risk of developing or having a fibrotic disorder a therapeutically effective amount of a modulator specific for any one of the genes (including any alleles, homologs, or orthologs) or any encoded products (including any active fragments or splice variants thereof) listed in FIG. 7, Table 1, Table 3A, Table 3B, Table 5, Table 6, Table 7, an eIF2 component or regulator, an eIF4F complex or regulator, an eIF4F complex component or regulator, an eIF5A or regulator, or any combination thereof.

In another aspect, the instant disclosure provides a method for identifying a candidate therapeutic for normalizing a translational profile associated with a fibrotic disease, comprising (a) determining three independent translational profiles, each for a plurality of genes, wherein (i) a first translational profile is from a fibrotic disease sample, (ii) a second translational profile is from (1) a control non-diseased sample or (2) a control non-diseased sample contacted with a candidate agent, and (iii) a third translational profile is from the fibrotic disease sample contacted with a candidate agent; (b) determining a first differential translational profile comprising one or more genes differentially translated in the first translational profile as compared to the second translational profile, and determining a second differential translational profile comprising one or more genes differentially translated in the first translational profile as compared to the third translational profile, wherein the one or more differentially translated genes are selected from EIF2AK1, EIF2AK2, EIF2AK3, EIF2AK4, EIF5A, mTOR, DOHH, DHPS, HDAC6, SIRT2, RSK, AHCY, or the genes listed in FIG. 7, Table 1, Table 3A, Table 3B, Table 5, Table 6 or Table 7; and (c) identifying the agent as a candidate therapeutic for normalizing a translational profile associated with the fibrotic disorder when the first differential translational profile is comparable to the second differential translational profile.

In still another aspect, the instant disclosure provides a method for validating a target for normalizing a translational profile associated with a fibrotic disease, the method comprising (a) determining three independent translational profiles, each for a plurality of genes, wherein (i) a first translational profile is from a fibrotic disease sample, (ii) a second translational profile is from (1) a control non-diseased sample or (2) a control non-diseased sample contacted with an agent that modulates a target (e.g., an eIF2 component; an eIF2 regulator such as EIF2AK1, EIF2AK2, EIF2AK3 or EIF2AK4; an eIF4F complex component such as eIF4A or eIF4E; eIF5A or a regulator of eIF5A such as DHPS or DOHH), and (iii) a third translational profile is from the fibrotic disease sample contacted with the agent that modulates the target; (b) determining a first differential translational profile comprising one or more genes differentially translated in the first translational profile as compared to the second translational profile, and determining a second differential translational profile comprising one or more genes differentially translated in the first translational profile as compared to the third translational profile, wherein the one or more differentially translated genes are selected from, for example, EIF2AK1, EIF2AK2, EIF2AK3, EIF2AK4, EIF5A, mTOR, DOHH, DHPS, HDAC6, SIRT2, RSK, AHCY, or the genes listed in FIG. 7, Table 1, Table 3A, Table 3B, Table 5 or Table 7; and (c) validating the target as a target for normalizing a translational profile associated with the fibrotic disease when the first differential translational profile is comparable to the second differential translational profile.

In certain aspects, a target comprises a translation machinery element, a regulator of a translation machinery component, or combinations thereof. In certain embodiments, a target comprises an eIF2 component (e.g., eIF2α, eIF2β, eIF2γ), an eIF4F complex, an eIF4F complex component (e.g., eIF4E, eIF4A, eIF4G), or any combination thereof. In particular embodiments, a target comprises eIF2α, eIF2β, eIF2γ, eIF4A, eIF4E, eIF5A, rpS6, or any combination thereof. In further embodiments, a target comprises an eIF2α kinase (e.g., EIF2AK1 or heme-regulated inhibitor kinase (Hill), EIF2AK2 or double-stranded RNA-dependent kinase (protein kinase R, PKR), EIF2AK3 or PKR-like endoplasmic reticulum kinase (PERK), EIF2AK4 or general control nonderepressible 2 (GCN2)), mTOR, deoxyhypusine hydroxylase (DOHH), deoxyhypusine synthase (DHPS), histone deacetylase 6 (HDAC6), NAD-dependent deacetylase sirtuin-2 (SIRT2), p90 Ribosomal S6 kinase (RSK), adenosylhomocysteinase (AHCY), or any combination thereof.

In certain embodiments, a therapeutically effective amount of a modulator specifically targeting eIF2AK1 activity, eIF2AK2 activity, eIF2AK3 activity, eIF2AK4 activity, eIF4A activity, eIF5A activity, or DOHH activity is administered to a subject at risk of developing or having a fibrotic disorder in order to reduce the amount of myofibroblasts contributing to the fibrotic disorder. The reduction may be due to promoting apoptosis of the existing myofibroblasts, reducing or inhibiting transdifferentiation of fibroblasts into myofibroblasts, promoting transdifferentiation of myofibroblasts into another cell type, inducing senescence or quiescence of myofibroblasts, or any combination thereof. In other embodiments, a therapeutically effective amount of a modulator specifically targeting eIF2AK1 activity, eIF2AK2 activity, eIF2AK3 activity, eIF2AK4 activity, eIF4A activity, eIF5A activity, or DOHH activity is administered to a subject having a fibrotic disorder in order to inhibit or block the production, secretion or both of organ damaging proteins from myofibroblasts (e.g., ECM related proteins). In further embodiments, a modulator specifically targets a nucleic acid encoding the eIF2AK1 activity, eIF2AK2 activity, eIF2AK3 activity, eIF2AK4 activity, eIF4A activity, eIF5A activity, or DOHH activity. For example, a specific modulator may be an siRNA or a derivative thereof (e.g., nuclease resistant modifications, such as phosphorothioate, locked nucleic acids (LNA), 2'-O-methyl modifications, morpholino linkages, or the like).

In particular embodiments, a modulator specifically targeting DOHH activity does not modulate or minimally modulates other protein hydroxylases, such as lysyl-hydroxylase, prolyl-hydroxylase and aspartyl/asparaginyl hydroxylase. By way of background, during the formation and maintenance of fibrocellular scar tissue, certain proteins like collagen and the chaperone LTBP are hydroxylated (e.g., prolyl-4-hydroxylase modifies proline to 4-hydroxyproline (Hyp) on collagen and the presence of Hyp is required for collagen structural stability). A surprising result of this disclosure is that specific inhibition of DOHH alone (without affecting other hydroxylases) will inhibit or reverse transdifferentiation of fibroblasts into myofibroblasts, inhibit the production and/or secretion of organ damaging proteins produced by myofibroblasts—therefore, specific inhibition of DOHH can be used to treat or prevent fibrotic disorders.

In further particular embodiments, a modulator specifically targeting eIF2AK1 activity will inhibit or reverse transdifferentiation of fibroblasts into myofibroblasts and, therefore, treat or prevent fibrotic disorders. In certain embodiments, a modulator specifically targeting eIF2AK1 activity is used to treat or ameliorate fibrotic disorders by inhibiting or blocking the production, secretion or both of organ damaging proteins from myofibroblasts.

In further particular embodiments, a modulator specifically targeting eIF2AK2 activity will inhibit or reverse transdifferentiation of fibroblasts into myofibroblasts and, therefore, treat or prevent fibrotic disorders. In certain embodiments, a modulator specifically targeting eIF2AK2 activity is used to treat or ameliorate fibrotic disorders by inhibiting or blocking the production, secretion or both of organ damaging proteins from myofibroblasts.

In further particular embodiments, a modulator specifically targeting eIF2AK3 activity will inhibit or reverse transdifferentiation of fibroblasts into myofibroblasts and, therefore, treat or prevent fibrotic disorders. In certain embodiments, a modulator specifically targeting eIF2AK3 activity is used to treat or ameliorate fibrotic disorders by inhibiting or blocking the production, secretion or both of organ damaging proteins from myofibroblasts.

In further particular embodiments, a modulator specifically targeting eIF2AK4 activity will inhibit or reverse transdifferentiation of fibroblasts into myofibroblasts and, therefore, treat or prevent fibrotic disorders. In certain embodiments, a modulator specifically targeting eIF2AK4 activity is used to treat or ameliorate fibrotic disorders by inhibiting or blocking the production, secretion or both of organ damaging proteins from myofibroblasts.

In still further particular embodiments, a modulator specifically targeting eIF4A activity will inhibit or reverse transdifferentiation of fibroblasts into myofibroblasts and, therefore, treat or prevent fibrotic disorders. In certain embodiments, a modulator specifically targeting eIF4A activity is used to treat or ameliorate fibrotic disorders by inhibiting or blocking the production, secretion or both of organ damaging proteins from myofibroblasts.

In yet further particular embodiments, a modulator specifically targeting eIF5A activity will inhibit or reverse transdifferentiation of fibroblasts into myofibroblasts and, therefore, treat or prevent fibrotic disorders. In certain embodiments, a modulator specifically targeting eIF5A activity is used to treat or ameliorate fibrotic disorders by inhibiting or blocking the production, secretion or both of organ damaging proteins from myofibroblasts.

In certain embodiments, a target comprises CREB5, DIAPH3, LGALS1, NACA, RPL12, RPL13A, RPL17, RPL21, RPL22L1, RPL23, RPL26, RPL27A, RPL28, RPL3, RPL30, RPL34, RPL36, RPL37, RPL37A, RPL4, RPL7A, RPS9, RPLP1, RPLP2, RPS10, RPS16, RPS19, RPS27, RPS5, RPS8, RPS9, SLC25A6, SOX6, STS, TKT or any combination thereof. In further embodiments, a target comprises ABCA6, ANKH, CARD16, CEP192, DDX60, DNASE1L1, DYNC2H1, EDN1, HBEGF, HOMER1, INHBA, KDM6B, LENG9, MATN3, MYO19, NRG1, PABPC4, PLD1, PLEKHA5, RASD1, SGIP1, SLC2A12, SNRPA, TEN1, TOP2A, TRERF1 or any combination thereof. In still further embodiments, a target comprises C9orf85, EIF3E, GAPDH, HNRNPA1, MRPL45 or any combination thereof. In yet further embodiments, a target comprises CES1, LAMP5, PAQR5 PLEKHG1, ROBO2, TOMM7 or any combination thereof. In more embodiments, a target comprises AOX1, ARPC1A, AURKA, C12orf57, GPSM2, KITLG, MAP3K5, MURC, NOV, RPL14, SLC15A3, SOX5, ZNF608 or any combination thereof.

In certain embodiments, a target comprises ANKDD1A, ATP5G2, CHCHD10, DNAJC22, FGF5, FMO2, GNB2L1, GLTSCR2, HIGD2A, IFIH, MTUS1, RPS18, RPL18A, RPL31, RPL35A, RPL5, RPS18, RPS29, SPATA6 or any combination thereof. In further embodiments, a target comprises RPS6KA5, BIVM, ACTA1, KRT7, AMIGO3, CCDC102B, RPL10, TAF1D, ADAMTS5, LAMB3, CLCF1, EPB41L1, GAS2L3, IRAK3, LPAR3, PCBP2, PDE7B, TMTC1, FRMD4A, GDF10, OBSCN, PLEKHA6, SHC3 or any combination thereof. In still further embodiments, a target comprises THBS3, RPS28, EEF1A1, EEF2, EIF4B, FMO2, RAB3D, CIT, PDE4B, PPARG, SLC40A1, ASPM, CA5B, GLCCI1, GLTSCR2, P2RX7, STAMBPL1 or any combination thereof.

In some aspects, the instant disclosure provides a method of identifying a subject as a candidate for preventing, treating or ameliorating a fibrotic disease with a therapeutic agent, the method comprising (a) determining a first translational profile for a plurality of genes in a sample from a subject having or suspected of having a fibrotic disease; (b) determining a second translational profile for a plurality of genes in a control sample, wherein the control sample is from a subject known to respond to the therapeutic agent and wherein the sample has not been contacted with the therapeutic agent; and (c) identifying the subject as a candidate for treating fibrotic disease with the therapeutic agent when the translational profile for one or more genes selected from, for example, EIF2AK1, EIF2AK2, EIF2AK3, EIF2AK4, EIF5A, mTOR, DOHH, DHPS, HDAC6, SIRT2, RSK, AHCY, or FIG. 7, Table 1, Table 3A, Table 3B, Table 5 or Table 7 of the first translational profile are comparable to the translational profile of the corresponding genes in the second translational profile. In a related aspect, the instant disclosure provides a method for preventing, treating or ameliorating a fibrotic disease, comprising administering a therapeutic agent to a subject identified according to the method of identifying a subject as a candidate for preventing, treating or ameliorating a fibrotic disease, thereby treating the subject. In certain embodiments, a method of identifying a subject as a candidate for preventing, treating or ameliorating a fibrotic disease with a therapeutic agent comprises using any one or more of the combinations of modulators described herein.

In any of the aforementioned embodiments, the fibrotic disease or disorder may be due to injury or may be idiopathic. In some embodiments, the injury is an ischemic event or due to exposure to radiation, a chemical, or an infectious agent. In any of these embodiments, a specific modulator for an eIF2 pathway protein or regulator (such as EIF2AK1, EIF2AK2, EIF2AK3 or EIF2AK4), a specific modulator of an eIF4F complex or component thereof (such as eIF4A or eIF4E), a specific modulator of an eIF5A or a regulator of eIF5A (such as DHPS or DOHH), or any combination thereof is administered before or after a fibrotic lesion has developed in the subject. In further embodiments, a modulator specific for a target of interest is formulated with a pharmaceutically acceptable diluent, carrier or excipient.

In certain embodiments, the present disclosure provides methods for treating fibrotic disorders or for inhibiting transdifferentiation of fibroblasts into myofibroblasts by administering a modulator of a first target combined with one or more modulators of one or more different targets (e.g., two, three, four, five, or six targets). In some embodiments, the first target is a first translation machinery element and the second target is a second a translation machinery element; or the first target is a translation machinery element and the second target is a regulator of a translation machinery element; or the first target is a regulator of a first translation machinery element and the second target is a regulator of a second translation machinery element; or the first target is a first regulator of a first translation machinery element and the second target is a second regulator of the first translation machinery element, or any combination thereof. Any of the combination embodiments described herein may include one or more modulators that are specific for the named target.

Exemplary methods for treating fibrotic disorders or for inhibiting transdifferentiation of fibroblasts into myofibroblasts or for reducing the presence of myofibroblasts or for inhibiting or blocking the production and/or secretion of organ damaging proteins from myofibroblasts, or any combination thereof, comprise administering combinations of two or more modulators (for the same or different targets) of this disclosure. In any of these embodiments, a modulator may be specific for its target.

Representative combinations of modulators for use in the methods described herein include (1) a modulator of eIF4A and a modulator of eIF2A, (2) a modulator of eIF4A and a modulator of eIF2AK1, (3) a modulator of eIF4A and a modulator of eIF5A, (4) a modulator of eIF4A and a modulator of DHPS, (5) a modulator of eIF4A and a modulator of DOHH, (6) a modulator of eIF4A and a modulator of eEF1A1, (7) a modulator of eIF4A and a modulator of eEF2, (8) a modulator of eIF4A and a modulator of eEF2K, (9) a modulator of eIF4A and a modulator of eIF4B, (10) a modulator of eIF4A and a modulator of eIF4G, or (11) any combination thereof.

In further embodiments, combinations of modulators for use in the methods described herein comprise (1) a modulator of eIF4E and a modulator of eIF2A, (2) a modulator of eIF4E and a modulator of eIF2AK1, (3) a modulator of eIF4E and a modulator of eIF5A, (4) a modulator of eIF4E and a modulator of DHPS, (5) a modulator of eIF4E and a modulator of DOHH, (6) a modulator of eIF4E and a modulator of eEF1A1, (7) a modulator of eIF4E and a modulator of eEF2, (8) a modulator of eIF4E and a modulator of eEF2K, (9) a modulator of eIF4E and a modulator of eIF4B, (10) a modulator of eIF4E and a modulator of eIF4G, or (11) any combination thereof.

In other embodiments, combinations of modulators for use in the methods described herein comprise (1) a modulator of eIF4G and a modulator of eIF2A, (2) a modulator of eIF4G and a modulator of eIF2AK1, (3) a modulator of eIF4G and a modulator of eIF5A, (4) a modulator of eIF4G and a modulator of DHPS, (5) a modulator of eIF4G and a modulator of DOHH, (6) a modulator of eIF4G and a modulator of eEF1A1, (7) a modulator of eIF4G and a modulator of eEF2, (8) a modulator of eIF4G and a modulator of eEF2K, (9) a modulator of eIF4G and a modulator of eIF4B, or (10) any combination thereof.

In still further embodiments, combinations of modulators for use in the methods described herein comprise (1) a modulator of eIF4B and a modulator of eIF2A, (2) a modulator of eIF4B and a modulator of eIF2AK1, (3) a modulator of eIF4B and a modulator of eIF5A, (4) a modulator of eIF4B and a modulator of DHPS, (5) a modulator of eIF4B and a modulator of DOHH, (6) a modulator of eIF4B and a modulator of eEF1A1, (7) a modulator of eIF4B and a modulator of eEF2, (8) a modulator of eIF4B and a modulator of eEF2K, or (9) any combination thereof.

In further embodiments, combinations of modulators for use in the methods described herein comprise (1) a modulator of eIF2A and a modulator of eIF2AK, (2) a modulator of eIF2A and a modulator of eIF5A, (3) a modulator of eIF2A and a modulator of DHPS, (4) a modulator of eIF2A and a modulator of DOHH, (5) a modulator of eIF2A and a modulator of eEF1A1, (6) a modulator of eIF2A and a modulator of eEF2, (7) a modulator of eIF2A and a modulator of eEF2K, or (8) any combination thereof.

In yet further embodiments, combinations of modulators for use in the methods described herein comprise (1) a modulator of eIF2AK and a modulator of eIF5A, (2) a modulator of eIF2AK and a modulator of DHPS, (3) a modulator of eIF2AK and a modulator of DOHH, (4) a modulator of eIF2AK and a modulator of eEF1A1, (5) a modulator of eIF2AK and a modulator of eEF2, (6) a modulator of eIF2AK and a modulator of eEF2K, or (7) any combination thereof.

In certain embodiments, combinations of modulators for use in the methods described herein comprise (1) a modulator of DHPS and a modulator of eIF5A, (2) a modulator of DHPS and a modulator of DOHH, (3) a modulator of DHPS and a modulator of eEF1A1, (4) a modulator of DHPS and a modulator of eEF2, (5) a modulator of DHPS and a modulator of eEF2K, or (6) any combination thereof.

In more embodiments, combinations of modulators for use in the methods described herein comprise (1) a modulator of DOHH and a modulator of eIF5A, (2) a modulator of DOHH and a modulator of eEF1A1, (3) a modulator of DOHH and a modulator of eEF2, (4) a modulator of DOHH and a modulator of eEF2K, or (5) any combination thereof.

In still more embodiments, combinations of modulators for use in the methods described herein comprise (1) a modulator of eIF5A and a modulator of eEF1A1, (2) a modulator of eIF5A and a modulator of eEF2, (3) a modulator of eIF5A and a modulator of eEF2K, or (4) any combination thereof.

More exemplary methods for treating fibrotic disorders or for inhibiting transdifferentiation of fibroblasts into myofibroblasts or for reducing the presence of myofibroblasts or for inhibiting or blocking the production and/or secretion of organ damaging proteins from myofibroblasts, or any combination thereof, comprise administering combinations of modulators targeting at least two different regulators of translation machinery elements, such as (1) a modulator of eIF2AK1 and a modulator of a PI3K, (2) a modulator of eIF2AK1 and a modulator of an AKT, (3) a modulator of eIF2AK1 and a modulator of mTOR, (4) a modulator of eIF2AK1 and a modulator of a S6K70, (5) a modulator of eIF2AK1 and a modulator of an MNK, (6) a modulator of eIF2AK1 and a modulator of a MEK1/2, (7) a modulator of eIF2AK1 and a modulator of an ERK, (8) a modulator of eIF2AK1 and a modulator of a RSK90, (9) a modulator of eIF2AK1 and a modulator of eEF2K, or (10) any combination thereof.

In further embodiments, combinations of modulators for use in the methods described herein comprise (1) a modulator of eIF2AK2 and a modulator of a PI3K, (2) a modulator of eIF2AK2 and a modulator of an AKT, (3) a modulator of eIF2AK2 and a modulator of mTOR, (4) a modulator of eIF2AK2 and a modulator of a S6K70, (5) a modulator of eIF2AK2 and a modulator of an MNK, (6) a modulator of eIF2AK2 and a modulator of a MEK1/2, (7) a modulator of eIF2AK2 and a modulator of an ERK, (8) a modulator of eIF2AK2 and a modulator of a RSK90, (9) a modulator of eIF2AK2 and a modulator of eEF2K, or (10) any combination thereof.

In still further embodiments, combinations of modulators for use in the methods described herein comprise (1) a modulator of eIF2AK3 and a modulator of a PI3K, (2) a modulator of eIF2AK3 and a modulator of an AKT, (3) a modulator of eIF2AK3 and a modulator of mTOR, (4) a modulator of eIF2AK3 and a modulator of a S6K70, (5) a modulator of eIF2AK3 and a modulator of an MNK, (6) a modulator of eIF2AK3 and a modulator of a MEK1/2, (7) a modulator of eIF2AK3 and a modulator of an ERK, (8) a modulator of eIF2AK3 and a modulator of a RSK90, (9) a modulator of eIF2AK3 and a modulator of eEF2K, or (10) any combination thereof.

In yet further embodiments, combinations of modulators for use in the methods described herein comprise (1) a modulator of eIF2AK4 and a modulator of a PI3K, (2) a modulator of eIF2AK4 and a modulator of an AKT, (3) a modulator of eIF2AK4 and a modulator of mTOR, (4) a modulator of eIF2AK4 and a modulator of a S6K70, (5) a modulator of eIF2AK4 and a modulator of an MNK, (6) a modulator of eIF2AK4 and a modulator of a MEK1/2, (7) a modulator of eIF2AK4 and a modulator of an ERK, (8) a modulator of eIF2AK4 and a modulator of a RSK90, (9) a modulator of eIF2AK4 and a modulator of eEF2K, or (10) any combination thereof.

In more embodiments, combinations of modulators for use in the methods described herein comprise (1) a modulator of GADD34 and a modulator of a PI3K, (2) a modulator of GADD34 and a modulator of an AKT, (3) a modulator of GADD34 and a modulator of mTOR, (4) a modulator of GADD34 and a modulator of a S6K70, (5) a modulator of GADD34 and a modulator of an MNK, (6) a modulator of GADD34 and a modulator of a MEK1/2, (7) a modulator of GADD34 and a modulator of an ERK, (8) a modulator of GADD34 and a modulator of a RSK90, (9) a modulator of GADD34 and a modulator of eEF2K, or (10) any combination thereof.

In other embodiments, combinations of modulators for use in the methods described herein comprise (1) a modulator of GSK3β and a modulator of a PI3K, (2) a modulator of GSK3β and a modulator of an AKT, (3) a modulator of GSK3β and a modulator of mTOR, (4) a modulator of GSK3β and a modulator of a S6K70, (5) a modulator of GSK3β and a modulator of an MNK, (6) a modulator of GSK3β and a modulator of a MEK1/2, (7) a modulator of GSK3β and a modulator of an ERK, (8) a modulator of GSK3β and a modulator of a RSK90, (9) a modulator of GSK3β and a modulator of eEF2K, or (10) any combination thereof.

In certain embodiments, combinations of modulators for use in the methods described herein comprise (1) a modulator of a PI3K and a modulator of a MNK, (2) a modulator of a PI3K and a modulator of DHPS, (3) a modulator of a PI3K and a modulator of DOHH, (4) a modulator of a PI3K and a modulator of a MEK1/2, (5) a modulator of a PI3K and a modulator of an ERK, (6) a modulator of a PI3K and a modulator of a RSK90, (7) a modulator of a PI3K and a modulator of eEF2K, or (8) any combination thereof.

In other embodiments, combinations of modulators for use in the methods described herein comprise (1) a modulator of an AKT and a modulator of a MNK, (2) a modulator of an AKT and a modulator of DHPS, (3) a modulator of an AKT and a modulator of DOHH, (4) a modulator of an AKT and a modulator of a MEK1/2, (5) a modulator of an AKT and a modulator of an ERK, (6) a modulator of an AKT and a modulator of a RSK90, (7) a modulator of an AKT and a modulator of eEF2K, or (8) any combination thereof.

In still other embodiments, combinations of modulators for use in the methods described herein comprise (1) a modulator of mTOR and a modulator of a MNK, (2) a modulator of mTOR and a modulator of DHPS, (3) a modulator of mTOR and a modulator of DOHH, (4) a modulator of mTOR and a modulator of a MEK1/2, (5) a modulator of mTOR and a modulator of an ERK, (6) a modulator of mTOR and a modulator of a RSK90, (7) a modulator of mTOR and a modulator of eEF2K, or (8) any combination thereof.

In yet other embodiments, combinations of modulators for use in the methods described herein comprise (1) a modulator of S6K70 and a modulator of a MNK, (2) a modulator of S6K70 and a modulator of DHPS, (3) a modulator of S6K70 and a modulator of DOHH, (4) a modulator of S6K70 and a modulator of a MEK1/2, (5) a modulator of S6K70 and a modulator of an ERK, (6) a modulator of S6K70 and a modulator of a RSK90, (7) a modulator of S6K70 and a modulator of eEF2K, or (8) any combination thereof.

In further embodiments, combinations of modulators for use in the methods described herein comprise (1) a modulator of a MNK and a modulator of DHPS, (2) a modulator of a MNK and a modulator of DOHH, (3) a modulator of a MNK and a modulator of a MEK1/2, (4) a modulator of a MNK and a modulator of an ERK, (5) a modulator of a MNK and a modulator of a RSK90, (6) a modulator of a MNK and a modulator of eEF2K, or (7) any combination thereof.

In other embodiments, combinations of modulators for use in the methods described herein comprise (1) a modulator of DHPS and a modulator of a MEK1/2, (2) a modulator of DHPS and a modulator of an ERK, (3) a modulator of DHPS and a modulator of a RSK90, (4) a modulator of DHPS and a modulator of eEF2K, or (5) any combination thereof.

In more embodiments, combinations of modulators for use in the methods described herein comprise administering (1) a modulator of DOHH and a modulator of a MEK1/2, (2) a modulator of DOHH and a modulator of an ERK, (3) a modulator of DOHH and a modulator of a RSK90, (4) a modulator of DOHH and a modulator of eEF2K, or (5) any combination thereof.

In even more embodiments, combinations of modulators for use in the methods described herein comprise administering (1) a modulator of eEF2K and a modulator of a MEK1/2, (2) a modulator of eEF2K and a modulator of an ERK, (3) a modulator of eEF2K and a modulator of a RSK90, or (4) any combination thereof.

Further exemplary methods for treating fibrotic disorders or for inhibiting transdifferentiation of fibroblasts into myofibroblasts or for reducing the presence of myofibroblasts or for inhibiting or blocking the production and/or secretion of organ damaging proteins from myofibroblasts, or any combination thereof, comprise administering combinations of modulators targeting at least two different translation machinery elements, such as (1) a modulator of an eIF4A and a modulator of a eEF1, (2) a modulator of an eIF4A and a modulator of an eEF2, (3) a modulator of an eIF4A and a modulator of eIF5A, or (4) any combination thereof.

In certain embodiments, combinations of modulators for use in the methods described herein comprise (1) a modulator of an eIF4E and a modulator of a eEF1, (2) a modulator of an eIF4E and a modulator of an eEF2, (3) a modulator of an eIF4E and a modulator of eIF5A, or (4) any combination thereof.

In further embodiments, combinations of modulators for use in the methods described herein comprise (1) a modulator of an eIF5A and a modulator of a eEF1, (2) a modulator of an eIF5A and a modulator of an eEF2, or (3) any combination thereof.

Additional exemplary methods for treating fibrotic disorders or for inhibiting transdifferentiation of fibroblasts into myofibroblasts or for reducing the presence of myofibroblasts or for inhibiting or blocking the production and/or secretion of organ damaging proteins from myofibroblasts, or any combination thereof, comprise administering combinations of modulators targeting at least one translation machinery element and at least one regulator of translation machinery elements, such as (1) a modulator of eIF2AK1 and a modulator of an eIF4A, (2) a modulator of eIF2AK1 and a modulator of an eIF4E, (3) a modulator of eIF2AK1 and a modulator of eEF1, (4) a modulator of eIF2AK1 and a modulator of a eEF2, (5) a modulator of eIF2AK1 and a modulator of an eIF5A, or (6) any combination thereof.

In certain embodiments, combinations of modulators for use in the methods described herein comprise (1) a modulator of eIF2AK2 and a modulator of an eIF4A, (2) a modulator of eIF2AK2 and a modulator of an eIF4E, (3) a modulator of eIF2AK2 and a modulator of eEF1, (4) a modulator of eIF2AK2 and a modulator of a eEF2, (5) a modulator of eIF2AK2 and a modulator of an eIF5A, or (6) any combination thereof.

In further embodiments, combinations of modulators for use in the methods described herein comprise (1) a modulator of eIF2AK3 and a modulator of an eIF4A, (2) a modulator of eIF2AK3 and a modulator of an eIF4E, (3) a modulator of eIF2AK3 and a modulator of eEF1, (4) a modulator of eIF2AK3 and a modulator of a eEF2, (5) a modulator of eIF2AK3 and a modulator of an eIF5A, or (6) any combination thereof.

In more embodiments, combinations of modulators for use in the methods described herein comprise (1) a modulator of eIF2AK4 and a modulator of an eIF4A, (2) a modulator of eIF2AK4 and a modulator of an eIF4E, (3) a modulator of eIF2AK4 and a modulator of eEF1, (4) a modulator of eIF2AK4 and a modulator of a eEF2, (5) a modulator of eIF2AK4 and a modulator of an eIF5A, or (6) any combination thereof.

In other embodiments, combinations of modulators for use in the methods described herein comprise (1) a modulator of GADD34 and a modulator of an eIF4A, (2) a modulator of GADD34 and a modulator of an eIF4E, (3) a modulator of GADD34 and a modulator of eEF1, (4) a modulator of GADD34 and a modulator of a eEF2, (5) a modulator of GADD34 and a modulator of an eIF5A, or (6) any combination thereof.

In still more embodiments, combinations of modulators for use in the methods described herein comprise (1) a modulator of GSK3β and a modulator of an eIF4A, (2) a modulator of GSK3β and a modulator of an eIF4E, (3) a modulator of GSK3β and a modulator of eEF1, (4) a modulator of GSK3β and a modulator of a eEF2, (5) a modulator of GSK3β and a modulator of an eIF5A, or (6) any combination thereof.

In certain embodiments, combinations of modulators for use in the methods described herein comprise (1) a modulator of a PI3K and a modulator of an eIF4A, (2) a modulator of a PI3K and a modulator of an eIF4E, (3) a modulator of a PI3K and a modulator of eEF1, (4) a modulator of a PI3K and a modulator of a eEF2, (5) a modulator of a PI3K and a modulator of an eIF5A, or (6) any combination thereof.

In further embodiments, combinations of modulators for use in the methods described herein comprise (1) a modulator of an AKT and a modulator of an eIF4A, (2) a modulator of an AKT and a modulator of an eIF4E, (3) a modulator of an AKT and a modulator of eEF1, (4) a modulator of an AKT and a modulator of a eEF2, (5) a modulator of an AKT and a modulator of an eIF5A, or (6) any combination thereof.

In more embodiments, combinations of modulators for use in the methods described herein comprise (1) a modulator of mTOR and a modulator of an eIF4A, (2) a modulator of mTOR and a modulator of an eIF4E, (3) a modulator of mTOR and a modulator of eEF1, (4) a modulator of mTOR and a modulator of a eEF2, (5) a modulator of mTOR and a modulator of an eIF5A, or (6) any combination thereof.

In more embodiments, combinations of modulators for use in the methods described herein comprise (1) a modulator of S6K70 and a modulator of an eIF4A, (2) a modulator of S6K70 and a modulator of an eIF4E, (3) a modulator of S6K70 and a modulator of eEF1, (4) a modulator of S6K70 and a modulator of a eEF2, (5) a modulator of S6K70 and a modulator of an eIF5A, or (6) any combination thereof.

In certain embodiments, combinations of modulators for use in the methods described herein comprise (1) a modulator of a MNK and a modulator of an eIF4A, (2) a modulator of a MNK and a modulator of an eIF4E, (3) a modulator of a MNK and a modulator of eEF1, (4) a modulator of a MNK and a modulator of a eEF2, (5) a modulator of a MNK and a modulator of an eIF5A, or (6) any combination thereof.

In certain embodiments, combinations of modulators for use in the methods described herein comprise (1) a modulator of a MEK1/2 and a modulator of an eIF4A, (2) a modulator of a MEK1/2 and a modulator of an eIF4E, (3) a modulator of a MEK1/2 and a modulator of eEF1, (4) a modulator of a MEK1/2 and a modulator of a eEF2, (5) a modulator of a MEK1/2 and a modulator of an eIF5A, or (6) any combination thereof.

In further embodiments, combinations of modulators for use in the methods described herein comprise (1) a modulator of an ERK and a modulator of an eIF4A, (2) a modulator of an ERK and a modulator of an eIF4E, (3) a modulator of an ERK and a modulator of eEF1, (4) a modulator of an ERK and a modulator of a eEF2, (5) a modulator of an ERK and a modulator of an eIF5A, or (6) any combination thereof.

In more embodiments, combinations of modulators for use in the methods described herein comprise (1) a modulator of RSK90 and a modulator of an eIF4A, (2) a modulator of RSK90 and a modulator of an eIF4E, (3) a modulator of RSK90 and a modulator of eEF1, (4) a modulator of RSK90 and a modulator of a eEF2, (5) a modulator of RSK90 and a modulator of an eIF5A, or (6) any combination thereof.

In even more embodiments, combinations of modulators for use in the methods described herein comprise (1) a modulator of eEF2K and a modulator of an eIF4A, (2) a modulator of eEF2K and a modulator of an eIF4E, (3) a modulator of eEF2K and a modulator of an eIF5A, or (4) any combination thereof.

In any of the combination therapies described herein, a combination of modulators can be administered serially, simultaneously, or concurrently. When administering serially, a first modulator or pharmaceutical composition thereof is formulated in a separate composition from a second (or third, etc.) modulator or pharmaceutical composition thereof. When administering simultaneously or concurrently, a first and second (or third, etc.) modulator may be formulated in separate compositions or formulated in a single composition. In any of these embodiments, the single or combination modulator therapies can be administered as a single dose unit or administered as a single dose unit a plurality of times (daily, weekly, biweekly, monthly, biannually, annually, etc., or any combination thereof).

In certain embodiments, a combination therapy described herein is used in a method for treating a fibrotic disorder or disease. In further embodiments, a combination therapy described herein is used in a method for inhibiting transdifferentiation of fibroblasts into myofibroblasts. In still further embodiments, a combination therapy described herein is used in a method for reducing the presence of myofibroblasts. In yet further embodiments, a combination therapy described herein is used in a method for inhibiting or blocking the production and/or secretion of organ damaging proteins from myofibroblasts.

In certain embodiments, a combination of modulators described herein is used in a method of identifying a subject as a candidate for preventing, treating or ameliorating a fibrotic disease with a therapeutic agent.

In still further embodiments, a modulator of a target of interest or any of the aforementioned combinations, which may be specific for their target, are administered in combination with one or more adjunctive therapeutic agents, such as angiotensin converting enzyme inhibitor, nintedanib (BIBF-1120), STX-100, QAX576, CNTO-888, SD-208, SB-525334, GC1008, BMS-986202, AM152, lebrikizumab, tralokinumab, SAR156597, PRM-151, simtuzumab (AB0024, GS-6624), GSK2126458, FG-3019, captopril, genistein, EUK-207, silvestrol or derivatives thereof, pateamine A or derivatives thereof, hippuristanol, or pirfenidone, for the treatment of, for example, a fibrotic disorder (such as idiopathic pulmonary fibrosis).

In any of the aforementioned embodiments, the fibrotic disease or disorder is a pulmonary fibrosis, idiopathic pulmonary fibrosis, cystic fibrosis, liver fibrosis, cardiac fibrosis, endomyocardial fibrosis, atrial fibrosis, mediastinal fibrosis, myelofibrosis, retroperitoneal fibrosis, chronic kidney disease, nephrogenic systemic fibrosis, Chron's disease, hypertrophic scarring, keloid, scleroderma, organ transplant-associated fibrosis, ischemia-associated fibrosis, or a combination thereof. In any of the aforementioned embodiments, the subject is a human.

Subjects in need of administration of therapeutic agents as described herein include subjects at high risk for developing a fibrotic disorder as well as subjects presenting with an existing fibrotic disorder. A subject may be at high risk for developing a fibrotic disorder if the subject has experienced an injury, for example: exposure to radiation, environmental or occupational pollutant, chemical, irritant, certain medications, infectious agent; having a certain genetic mutation; chronic autoimmune response; or an ischemic event. Subjects suffering from or suspected of having a fibrotic disorder can be identified using methods as described herein. A subject may be any organism capable of developing a fibrotic disorder, such as humans, pets, livestock, show animals, zoo specimens, or other animals. For example, a subject may be a human, a non-human primate, dog, cat, rabbit, horse, or the like.

The therapeutic agents or pharmaceutical compositions that treat or reduce the risk of developing a fibrotic disorder provided herein are administered to a subject who has or is at risk of developing a fibrotic disorder at a therapeutically effective amount or dose. Such a dose may be determined or adjusted depending on various factors including the specific therapeutic agents or pharmaceutical compositions, the routes of administration, the subject's condition, that is, stage of the disease, severity of symptoms caused by the disease, general health status, as well as age, gender, and weight, and other factors apparent to a person skilled in the medical art. Similarly, the dose of the therapeutic for treating a disease or disorder may be determined according to parameters understood by a person skilled in the medical art. When referring to a combination, a therapeutically effective dose refers to combined amounts of the active ingredients that result in the therapeutic effect, whether administered serially or simultaneously (in the same formulation or concurrently in separate formulations). Optimal doses may generally be determined using experimental models and/or clinical trials. Design and execution of pre-clinical and clinical studies for a therapeutic agent (including when administered for prophylactic benefit) described herein are well within the skill of a person skilled in the relevant art.

Generally, the therapeutic agent is administered at a therapeutically effective amount or dose. A therapeutically effective amount or dose will vary according to several factors, including the chosen route of administration, formulation of the composition, patient response, severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is well within the capability of those skilled in the art.

The route of administration of a therapeutic agent can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art.

In some embodiments, a therapeutic agent is formulated as a pharmaceutical composition. In some embodiments, a pharmaceutical composition incorporates particulate forms, protective coatings, protease inhibitors, or permeation enhancers for various routes of administration, including parenteral, pulmonary, nasal and oral. The pharmaceutical compositions can be administered in a variety of unit dosage forms depending upon the method/mode of administration. Suitable unit dosage forms, including powders, tablets, pills, capsules, lozenges, suppositories, patches, nasal sprays, injectables, implantable sustained-release formulations, etc.

In some embodiments, a pharmaceutical composition comprises an acceptable diluent, carrier or excipient. A pharmaceutically acceptable carrier includes any solvent, dispersion media, or coating that are physiologically compatible and that preferably do not interfere with or otherwise inhibit the activity of the therapeutic agent. Preferably, a carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known and generally described in, for example, *Remington: The Science and Practice of Pharmacy*, 21st Edition, Philadelphia, Pa. Lippincott Williams & Wilkins, 2005. Various pharmaceutically acceptable excipients are well-known in the art and can be found in, for example, Handbook of Pharmaceutical Excipients (5$^{th}$ ed., Ed. Rowe et al., Pharmaceutical Press, Washington, D.C.).

EXAMPLES

Example 1

Effect of mTOR Inhibition on Fibrotic Disease Development

TGFβ-mediated transformation of fibroblasts into fibrotic myofibroblasts is well-established as an essential step in fibroplasia, a key component of many fibrotic disorders (Blobe et al., *N. Engl. J. Med.* 342:1350, 2000; Border and Noble, *N. Engl. J. Med.* 331:1286, 1994). This TGFβ-mediated transformation of fibroblasts was used as a model for examining fibrotic disorders.

Briefly, normal human lung fibroblasts (Lonza #CC-2512; cell passage numbers 2 through 5 were used for all experiments) were seeded (Day 0) and cultured in Dulbecco's modified Eagle medium (DMEM) supplemented with 10% fetal bovine serum (FBS), penicillin, streptomycin and glutamax (Invitrogen) at 37° C. in a humidified incubator with 5% $CO_2$ overnight. On Day 1, cells were harvested, washed with phosphate buffered saline (PBS), and then incubated for 48 hours in fresh serum-free DMEM supplemented with penicillin, streptomycin, and glutamax. On Day 3, cells were harvested, resuspended in fresh serum-free DMEM containing PP242 (10, 2.5, 0.625, 0.156, 0.039, 0.01 or 0.002 μM) and 10 ng/ml TGFβ, and cultured for 24 hours. Controls included untreated cells, cells treated with TGFβ only, and cells treated with PP242 only.

After this 24 hour incubation, procollagen type 1 levels were measured by collecting culture media, centrifuging to pellet cellular debris, and stored at −80° C. Procollagen Type 1 C-Peptide (PIPC) was quantified using the (PIP) EIA kit (Clontech, Cat. No. MK101) according to manufacturer's instructions. The TGFβ-treated fibroblasts of this example were examined by ribosomal profiling (about $6 \times 10^6$ cells/10 cm plate) and western blot analysis (about $1 \times 10^6$ cells/well of a 6-well plate).

Results

Figure 2:
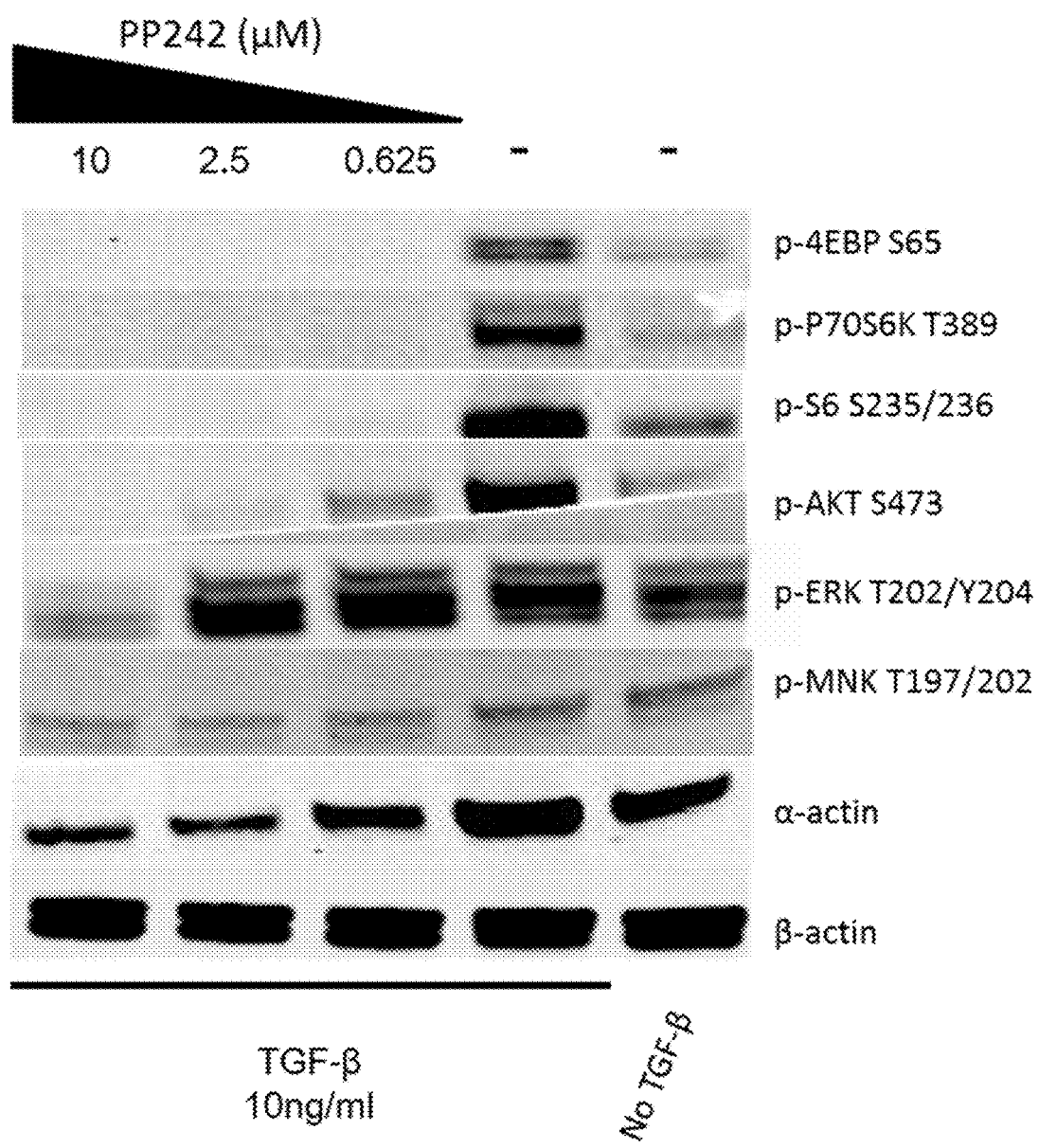
FIG. 2 shows a Western blot of protein phosphorylation levels during fibroblast transformation. Western blot analysis of fibroblast transformation as monitored by measuring α-smooth muscle actin (α-SMA) levels after 24 hrs of treating cells with various concentrations of mTOR inhibitor PP242 and 10 ng/mL TGFβ.

Transformation of fibroblasts into fibrotic myofibroblasts by treatment with TGFβ for 24 hours was accompanied by an approximately 7-fold increase in procollagen production, while treatment with PP242 was able to block this increase ($EC_{50}$ of about 0.2 μM) (FIG. 1). Expression of TGFβ induced myofibroblast differentiation marker, α-smooth muscle actin (α-SMA), was also analyzed by Western blot analysis (see Example 3; FIG. 2). After 24 hours of TGFβ stimulation, increased α-SMA protein levels were detectable, while the level of β-actin did not change. As with procollagen, co-incubation of cells with TGF-β and PP242 caused a reduction of the α-SMA protein level in a dose dependent manner.

Conclusion

Co-administration of TGF-β with mTOR inhibitor PP242 reverses or prevents the changes observed in a fibrotic disorder-related pathway as evidenced by an inhibition of increased production of fibrotic disorder biomarker proteins, type 1 procollagen and α-SMA (which are both hallmarks of TGFβ-mediated fibroblast transformation into myofibroblasts).

Example 2

Phosphorylation of Protein Translation Components: Effect of mTOR Inhibition on Fibrotic Disease Development TGFβ-dependent activation of the PI3K/Akt/mTOR and ERK pathways were also examined by western blot analysis (about $1 \times 10^6$ cells/well from a 6-well plate). Briefly, cells were washed with PBS and lysed in 1× cell lysis buffer (Cell Signaling Technology, Inc., Danvers, Mass.) for 15 minutes at 4° C. Lysates were briefly sonicated, clarified by centrifugation for 15 minutes at 14,000 rpm, and then supernatants were collected. Protein concentration in the soluble fraction was determined by BCA protein assay (Thermo Scientific, Rockford, Ill.). Samples of protein (20 μg) were resolved on 4-20% Bis-Tris gradient gel (Invitrogen, Carlsbad, Calif.) and transferred to nitrocellulose membrane. The resulting blots were blocked for 1 hour at room temperature with Odyssey blocking solution (LI-COR) and then incubated with primary antibodies at 4° C. overnight. The following day, each blot was washed three times for 10 minutes in TB ST, and then incubated with goat anti-rabbit fluorescent conjugated secondary antibody (IRDye 800 CW at 1:20,000; LI-COR) for 1 hour at room temperature. The blots were washed and scanned, and then specific proteins were detected by using the LI-COR Odyssey infrared imager. The following antibodies were used at 1:1000 dilution: anti-α-actin (Sigma #A2547), anti-phospho-4EBP(Ser65), anti-phospho-rpS6(Ser235/236)(#4858), anti-phospho-ERK1/2 (Thr202/Tyr204)(#4370), anti-phospho-p70S6K(Thr421/Ser424)(#9204), anti-phospho-pAKT(Ser473), anti-phospho-MNK(Thr197/202), and anti-β-actin (#4970). Unless otherwise indicated, the antibodies were from Cell Signaling Technology, Inc. (Danvers, Mass.).

Results

FIG. 2 shows that phosphorylation of AKT, 4EBP, S6K, and S6 of the mTOR pathway was strongly stimulated in fibroblasts treated with TGFβ, whereas only a moderate increase in ERK phosphorylation was observed. Co-incubation of cells with mTOR inhibitor PP242 (0.625 µM) was sufficient to abolish TGFβ-dependent increases in phosphorylation of AKT, 4EBP, S6K, and S6, as well as causing a decrease in α-SMA to pretreatment levels (FIG. 2).

Conclusion

Co-administration of TGFβ with mTOR inhibitor PP242 reverses or prevents the changes observed in a fibrotic disorder-related pathway (i.e., normalizes the translational efficiencies of the genes) and inhibits increased production of fibrotic disorder biomarker proteins, type 1 procollagen and α-smooth muscle actin (which are both hallmarks of TGFβ-mediated fibroblast transformation to myofibroblasts).

Example 3

Translational Profiling: Effect of mTOR Inhibition on Fibrotic Disease Development Ribosomal profiling allows for measurement of changes in transcription and translation on a genome-wide basis accompanying TGFβ-dependent transformation of fibroblasts to myofibroblasts. Ribosomal profiles of the TGFβ-treated fibroblasts from Example 1 (about $6 \times 10^6$ cells/10 cm plate) were prepared and analyzed for changes in translational efficiencies with respect to potential disease-associated cellular changes accompanying this TGFβ-induced transformation.

Briefly, cells were washed with cold PBS supplemented with cycloheximide and lysed with 1× mammalian cell lysis buffer for 10 minutes on ice. Lysates were clarified by centrifugation for 10 minutes at 14,000 rpm and supernatants were collected. Cell lysates were processed to generate ribosomal protected fragments and total mRNA according to the instructions included with the ARTseq Ribosome Profiling Kit (Illumina, San Diego, Calif.). Sequencing of total RNA (RNA) and of ribosome-protected fragments of RNA (RPF) was carried out using RNA-Seq methodology according to the manufacturer's instructions (Illumina). To analyze the ribosomal profiles, RNA-Seq reads were processed with tools from the FASTX-Toolkit (fastq_quality_trimmer, fastx_clipper and fastx_trimmer). Unprocessed and processed reads were evaluated for a variety of quality measures using FastQC, and processed reads were mapped to the human genome using TopHat (see, e.g., Trapnell et al., Bioinformatics 25:1105, 2009). Gene-by-gene assessment of the number of fragments strictly and uniquely mapping to the coding region of each gene was conducted using HTSeq-count, a component of the HTSeq package. Differential analyses of the transforming effect of TGFβ on fibroblasts and the effect of PP242 treatment on this transformation were carried out with the software packages DESeq for transcription (RNA counts) and translational rate (RPF counts) and BABEL for translational efficiency based upon ribosomal occupancy as a function of RNA level (RNA and RPF counts). Genes with low counts in either RPF or RNA were excluded from differential analyses. Pathway and network analyses of differential data were conducted using Ingenuity Pathway Analysis (IPA).

Results

Genes identified in TGFβ treated fibroblasts by Differential Expression Analysis (differential mRNA amount (transcription), differential translational rate (RPF counts) and differential translational efficiency (ratio of translational rate to mRNA amount)) are listed in Tables 1-3 (Table 3A shows genes with an altered translational efficiency identified after one profiling experiment and Table 3B has a refined gene list based on five replicate profiling experiments). These three gene signatures were analyzed for pathway and network connections using Ingenuity Pathway Analysis (IPA).

TABLE 1

Gene Signature with Altered Translation Rate

| ENSEMBL ID | HGNC ID | $\log_2$FC RPF (M)/RPF (Ctrl) | RPF p-value |
|---|---|---|---|
| ENSG00000049540 | ELN | 5.36941753 | 1.08E−07 |
| ENSG00000163661 | PTX3 | −5.3307069 | 1.41E−07 |
| ENSG00000107796 | ACTA2 | 5.26064763 | 1.67E−07 |
| ENSG00000146674 | IGFBP3 | 4.82169249 | 1.06E−06 |
| ENSG00000123610 | TNFAIP6 | 4.75270158 | 1.41E−06 |
| ENSG00000106366 | SERPINE1 | 4.33934001 | 6.65E−06 |
| ENSG00000171793 | CTPS | 4.09973744 | 2.08E−05 |
| ENSG00000138735 | PDE5A | −4.0235025 | 2.74E−05 |
| ENSG00000140416 | TPM1 | 3.97312305 | 2.76E−05 |
| ENSG00000148848 | ADAM12 | 3.93485546 | 3.60E−05 |
| ENSG00000076706 | MCAM | 4.03592992 | 3.84E−05 |
| ENSG00000139211 | AMIGO2 | 3.93283643 | 4.20E−05 |
| ENSG00000130707 | ASS1 | 3.94677625 | 5.20E−05 |
| ENSG00000103489 | XYLT1 | 3.66194114 | 0.0001064 |
| ENSG00000149591 | TAGLN | 3.60417531 | 0.00010993 |
| ENSG00000135074 | ADAM19 | 3.65751476 | 0.00011063 |
| ENSG00000177283 | FZD8 | 3.66199763 | 0.00012173 |
| ENSG00000197442 | MAP3K5 | −3.6700003 | 0.00015186 |
| ENSG00000162591 | MEGF6 | 3.52392664 | 0.00018903 |
| ENSG00000170558 | CDH2 | 3.37710278 | 0.00027648 |
| ENSG00000211455 | STK38L | 3.35942032 | 0.00033916 |
| ENSG00000164761 | TNFRSF11B | −3.3013119 | 0.0003522 |
| ENSG00000127863 | TNFRSF19 | −3.3472307 | 0.00036218 |
| ENSG00000006016 | CRLF1 | 3.35876314 | 0.0003716 |
| ENSG00000187498 | COL4A1 | 3.22671553 | 0.00043313 |
| ENSG00000128965 | CHAC1 | 3.32922215 | 0.00043675 |
| ENSG00000172986 | GXYLT2 | 3.34594516 | 0.0004446 |
| ENSG00000113140 | SPARC | 3.18391733 | 0.00050358 |
| ENSG00000189184 | PCDH18 | −3.2023222 | 0.00052431 |
| ENSG00000099860 | GADD45B | 3.15900734 | 0.0007182 |
| ENSG00000197321 | SVIL | −3.1352953 | 0.00074287 |
| ENSG00000176170 | SPHK1 | 3.17785195 | 0.00083387 |
| ENSG00000079308 | TNS1 | 3.0455728 | 0.00083771 |
| ENSG00000115884 | SDC1 | 3.08392695 | 0.00087241 |
| ENSG00000173809 | ITGA11 | 3.01124359 | 0.00103089 |
| ENSG00000135269 | TES | 3.05095571 | 0.00108443 |
| ENSG00000106211 | HSPB1 | 2.94411799 | 0.00117519 |
| ENSG00000122786 | CALD1 | 2.92932598 | 0.00122331 |
| ENSG00000137124 | ALDH1B1 | 2.99287373 | 0.0012512 |
| ENSG00000107957 | SH3PXD2A | 2.9304952 | 0.00130719 |

TABLE 1-continued

Gene Signature with Altered Translation Rate

| ENSEMBL ID | HGNC ID | log₂FC RPF (M)/RPF (Ctrl) | RPF p-value |
|---|---|---|---|
| ENSG00000206190 | ATP10A | 3.00335812 | 0.00131835 |
| ENSG00000163453 | IGFBP7 | 2.8797874 | 0.00145005 |
| ENSG00000137331 | IER3 | 2.83980944 | 0.00184245 |
| ENSG00000120708 | TGFBI | 2.80133447 | 0.00187418 |
| ENSG00000115902 | SLC1A4 | 2.85901341 | 0.00197395 |
| ENSG00000103257 | SLC7A5 | 2.80503703 | 0.00215617 |
| ENSG00000070371 | CLTCL1 | 2.90823707 | 0.00218709 |
| ENSG00000127241 | MASP1 | −2.7577773 | 0.00241631 |
| ENSG00000164292 | RHOBTB3 | −2.7504911 | 0.00246705 |
| ENSG00000171617 | ENC1 | 2.74021006 | 0.00248563 |
| ENSG00000158186 | MRAS | 2.92224323 | 0.00271268 |
| ENSG00000182752 | PAPPA | −2.7035058 | 0.00294361 |
| ENSG00000134853 | PDGFRA | −2.6580228 | 0.00312982 |
| ENSG00000165029 | ABCA1 | −2.6467049 | 0.00326207 |
| ENSG00000118523 | CTGF | 2.62517157 | 0.00334596 |
| ENSG00000198853 | RUSC2 | 2.65438677 | 0.00352266 |
| ENSG00000188641 | DPYD | −2.6916522 | 0.00352337 |
| ENSG00000147872 | PLIN2 | −2.6415827 | 0.00357964 |
| ENSG00000119408 | NEK6 | −2.6438108 | 0.00399688 |
| ENSG00000070669 | ASNS | 2.58331253 | 0.00400905 |
| ENSG00000065911 | MTHFD2 | 2.5641977 | 0.00439044 |
| ENSG00000131435 | PDLIM4 | 2.55921868 | 0.00458365 |
| ENSG00000197594 | ENPP1 | 2.56938165 | 0.00466656 |
| ENSG00000165124 | SVEP1 | −2.5106635 | 0.00496629 |
| ENSG00000104368 | PLAT | −2.5054577 | 0.00517753 |
| ENSG00000162804 | SNED1 | −2.5154081 | 0.00558283 |
| ENSG00000087008 | ACOX3 | 2.49632218 | 0.00613453 |
| ENSG00000156265 | C21orf7 | 2.56814445 | 0.00614218 |
| ENSG00000139329 | LUM | −2.4449067 | 0.00616621 |
| ENSG00000183010 | PYCR1 | 2.46985869 | 0.00638868 |
| ENSG00000214517 | PPME1 | 2.44759383 | 0.0065779 |
| ENSG00000111186 | WNT5B | 2.46335531 | 0.00661341 |
| ENSG00000122694 | GLIPR2 | 2.49429147 | 0.00678059 |
| ENSG00000100234 | TIMP3 | 2.40382243 | 0.00681395 |
| ENSG00000136542 | GALNT5 | −2.4288148 | 0.00695359 |
| ENSG00000198121 | LPAR1 | −2.4357876 | 0.00713053 |
| ENSG00000154553 | PDLIM3 | 2.45374968 | 0.00729327 |
| ENSG00000162520 | SYNC | 2.53882525 | 0.00736301 |
| ENSG00000135919 | SERPINE2 | 2.37546587 | 0.00738884 |
| ENSG00000115963 | RND3 | −2.3750235 | 0.00749913 |
| ENSG00000112096 | SOD2 | −2.4089889 | 0.00750824 |
| ENSG00000168994 | PXDC1 | 2.41631019 | 0.00757789 |
| ENSG00000130635 | COL5A1 | 2.36463839 | 0.00765854 |
| ENSG00000125257 | ABCC4 | −2.3915739 | 0.00767406 |
| ENSG00000175899 | A2M | −2.3564983 | 0.00789503 |
| ENSG00000147224 | PRPS1 | 2.42227839 | 0.00792948 |
| ENSG00000134352 | IL6ST | −2.3544877 | 0.00798272 |
| ENSG00000144655 | CSRNP1 | 2.42466893 | 0.00830203 |
| ENSG00000121068 | TBX2 | −2.3897652 | 0.00831686 |
| ENSG00000183963 | SMTN | 2.35351506 | 0.008544 |
| ENSG00000161638 | ITGA5 | 2.33254716 | 0.00856086 |
| ENSG00000073712 | FERMT2 | 2.3323394 | 0.00864574 |
| ENSG00000128590 | DNAJB9 | 2.35073771 | 0.00877118 |
| ENSG00000133816 | MICAL2 | 2.31968643 | 0.00902167 |
| ENSG00000113083 | LOX | 2.31217587 | 0.00910434 |
| ENSG00000105329 | TGFB1 | 2.31202161 | 0.00921304 |
| ENSG00000134871 | COL4A2 | 2.29661847 | 0.00939314 |
| ENSG00000106772 | PRUNE2 | 2.32751681 | 0.00944999 |
| ENSG00000152952 | PLOD2 | 2.28476269 | 0.00993745 |
| ENSG00000110328 | GALNTL4 | 2.45799148 | 0.00994213 |
| ENSG00000147852 | VLDLR | 2.32508202 | 0.01043418 |
| ENSG00000011422 | PLAUR | 2.29496533 | 0.01050673 |
| ENSG00000186340 | THBS2 | 2.26219171 | 0.01052617 |
| ENSG00000164465 | DCBLD1 | 2.29448412 | 0.01058626 |
| ENSG00000100889 | PCK2 | 2.28919489 | 0.01072773 |
| ENSG00000171223 | JUNB | 2.24626722 | 0.01131056 |
| ENSG00000134285 | FKBP11 | 2.28988985 | 0.01148763 |
| ENSG00000163110 | PDLIM5 | 2.23835271 | 0.01163489 |
| ENSG00000181104 | F2R | −2.2106721 | 0.01226847 |
| ENSG00000106799 | TGFBR1 | 2.21730253 | 0.01229293 |
| ENSG00000136205 | TNS3 | −2.2199359 | 0.01255329 |
| ENSG00000135048 | TMEM2 | 2.22084958 | 0.01287039 |
| ENSG00000099250 | NRP1 | −2.1921383 | 0.01318577 |
| ENSG00000196923 | PDLIM7 | 2.19174283 | 0.01327444 |
| ENSG00000175183 | CSRP2 | 2.23683689 | 0.01398546 |
| ENSG00000128591 | FLNC | 2.16561759 | 0.01399886 |
| ENSG00000165072 | MAMDC2 | 2.19235097 | 0.01402561 |
| ENSG00000135069 | PSAT1 | 2.1684862 | 0.01430236 |
| ENSG00000166888 | STAT6 | −2.2016097 | 0.0143223 |
| ENSG00000134668 | SPOCD1 | 2.30705749 | 0.01433835 |
| ENSG00000142552 | RCN3 | 2.14884922 | 0.01537399 |
| ENSG00000165801 | ARHGEF40 | 2.140188 | 0.0157109 |
| ENSG00000132688 | NES | 2.12201961 | 0.01691507 |
| ENSG00000141753 | IGFBP4 | −2.1015663 | 0.01722583 |
| ENSG00000158966 | CACHD1 | 2.19269046 | 0.01756212 |
| ENSG00000114850 | SSR3 | 2.08950932 | 0.01804143 |
| ENSG00000112902 | SEMA5A | −2.1061326 | 0.01873853 |
| ENSG00000067057 | PFKP | 2.070317 | 0.01875024 |
| ENSG00000072682 | P4HA2 | 2.06604184 | 0.01900324 |
| ENSG00000113361 | CDH6 | 2.07218406 | 0.01905514 |
| ENSG00000129038 | LOXL1 | 2.07073937 | 0.01937849 |
| ENSG00000154122 | ANKH | 2.09170046 | 0.01954498 |
| ENSG00000142871 | CYR61 | 2.0468831 | 0.01960644 |
| ENSG00000136603 | SKIL | 2.07686006 | 0.01962497 |
| ENSG00000135905 | DOCK10 | 2.13008136 | 0.01976733 |
| ENSG00000149256 | ODZ4 | −2.0726023 | 0.01995218 |
| ENSG00000065054 | SLC9A3R2 | 2.06603755 | 0.02075587 |
| ENSG00000107249 | GLIS3 | 2.20934781 | 0.02122407 |
| ENSG00000174099 | MSRB3 | 2.05355244 | 0.02238316 |
| ENSG00000198467 | TPM2 | 1.9923924 | 0.02282632 |
| ENSG00000135931 | ARMC9 | −2.039883 | 0.02397523 |
| ENSG00000100139 | MICALL1 | 2.04996518 | 0.02417362 |
| ENSG00000187840 | EIF4EBP1 | 2.02361386 | 0.02463796 |
| ENSG00000127418 | FGFRL1 | 2.04284709 | 0.02477047 |
| ENSG00000100600 | LGMN | 1.98781976 | 0.02480798 |
| ENSG00000129116 | PALLD | 1.9624052 | 0.02496631 |
| ENSG00000109861 | CTSC | −1.973874 | 0.02538713 |
| ENSG00000152377 | SPOCK1 | 1.95829856 | 0.02546107 |
| ENSG00000164574 | GALNT10 | 1.9899263 | 0.02554389 |
| ENSG00000006327 | TNFRSF12A | 1.95211091 | 0.02613436 |
| ENSG00000117143 | UAP1 | 1.93366364 | 0.02778912 |
| ENSG00000156642 | NPTN | 1.93440065 | 0.02800529 |
| ENSG00000163697 | APBB2 | 1.95832684 | 0.02848863 |
| ENSG00000162616 | DNAJB4 | 1.9411517 | 0.02867804 |
| ENSG00000132329 | RAMP1 | 1.96899533 | 0.02869506 |
| ENSG00000104635 | SLC39A14 | 1.93105847 | 0.02891801 |
| ENSG00000052802 | MSMO1 | 1.97230039 | 0.02897764 |
| ENSG00000117519 | CNN3 | 1.9058952 | 0.02919559 |
| ENSG00000152990 | GPR125 | −2.0967778 | 0.02924709 |
| ENSG00000196352 | CD55 | 1.9238114 | 0.02934175 |
| ENSG00000165323 | FAT3 | 2.00120682 | 0.02982447 |
| ENSG00000106105 | GARS | 1.89960819 | 0.02989086 |
| ENSG00000182492 | BGN | 1.89388618 | 0.03008093 |
| ENSG00000092841 | MYL6 | 1.89193012 | 0.03024906 |
| ENSG00000072110 | ACTN1 | 1.8896353 | 0.03037721 |
| ENSG00000131236 | CAP1 | 1.88826534 | 0.03083029 |
| ENSG00000135424 | ITGA7 | 1.90531417 | 0.03096942 |
| ENSG00000115053 | EFEMP1 | −1.872144 | 0.03198116 |
| ENSG00000136052 | SLC41A2 | 2.03094837 | 0.03254325 |
| ENSG00000104332 | SFRP1 | −1.8639924 | 0.03405278 |
| ENSG00000117152 | RGS4 | 1.9636591 | 0.03413922 |
| ENSG00000065413 | ANKRD44 | 1.93808539 | 0.03475794 |
| ENSG00000115129 | TP53I3 | 1.88563054 | 0.03483187 |
| ENSG00000164949 | GEM | 1.8466341 | 0.03627579 |
| ENSG00000007933 | FMO3 | −1.8668129 | 0.03664315 |
| ENSG00000070495 | JMJD6 | 1.9411517 | 0.03666109 |
| ENSG00000131981 | LGALS3 | −1.8278832 | 0.03684358 |
| ENSG00000173846 | PLK3 | 1.87764875 | 0.03706531 |
| ENSG00000100596 | SPTLC2 | 1.85354905 | 0.03718866 |
| ENSG00000131711 | MAP1B | 1.81244936 | 0.0376664 |
| ENSG00000117114 | LPHN2 | −1.9045313 | 0.03767601 |
| ENSG00000144724 | PTPRG | −1.8259538 | 0.03907041 |
| ENSG00000049323 | LTBP1 | 1.79396749 | 0.03916814 |
| ENSG00000155304 | HSPA13 | 1.80267254 | 0.03950001 |
| ENSG00000135047 | CTSL1 | −1.7963856 | 0.0401029 |
| ENSG00000159363 | ATP13A2 | 1.85868954 | 0.0405056 |
| ENSG00000101871 | MID1 | −1.9027541 | 0.04064161 |
| ENSG00000140682 | TGFB1I1 | 1.79894207 | 0.04076587 |
| ENSG00000181019 | NQO1 | −1.791716 | 0.04097796 |
| ENSG00000165996 | PTPLA | 1.90508244 | 0.04142984 |

TABLE 1-continued

Gene Signature with Altered Translation Rate

| ENSEMBL ID | HGNC ID | log$_2$FC RPF (M)/RPF (Ctrl) | RPF p-value |
|---|---|---|---|
| ENSG00000182054 | IDH2 | 1.84983653 | 0.04158138 |
| ENSG00000116016 | EPAS1 | −1.8287135 | 0.04167834 |
| ENSG00000142089 | IFITM3 | −1.7819417 | 0.04248534 |
| ENSG00000198018 | ENTPD7 | 1.91258254 | 0.04261311 |
| ENSG00000213949 | ITGA1 | 1.77199225 | 0.04266232 |
| ENSG00000166147 | FBN1 | 1.75788331 | 0.04302846 |
| ENSG00000163297 | ANTXR2 | −1.7756523 | 0.043628 |
| ENSG00000104518 | GSDMD | −1.8925912 | 0.04396197 |
| ENSG00000188643 | S100A16 | 1.76850759 | 0.04440116 |
| ENSG00000087303 | NID2 | −1.7533753 | 0.0447325 |
| ENSG00000138061 | CYP1B1 | −1.7576119 | 0.04494945 |
| ENSG00000132432 | SEC61G | 1.77185056 | 0.04531989 |
| ENSG00000169756 | LIMS1 | 1.77771073 | 0.046255 |
| ENSG00000060982 | BCAT1 | 1.75102124 | 0.04686101 |
| ENSG00000197622 | CDC42SE1 | 1.85639408 | 0.0476266 |
| ENSG00000100219 | XBP1 | 1.74004838 | 0.04778771 |
| ENSG00000136010 | ALDH1L2 | 1.72220246 | 0.04905653 |
| ENSG00000198856 | OSTC | 1.730833 | 0.04911071 |
| ENSG00000151729 | SLC25A4 | 1.81741633 | 0.04914682 |
| ENSG00000152818 | UTRN | −1.7488228 | 0.04936291 |
| ENSG00000168268 | NT5DC2 | 1.77572809 | 0.04980796 |

TABLE 2

Gene Signature with Altered Transcription

| ENSEMBL ID | HGNC ID | log2FC RNA (M)/RNA (Ctrl) | RNA p-value |
|---|---|---|---|
| ENSG00000107796 | ACTA2 | 5.69 | 8.88E−07 |
| ENSG00000049540 | ELN | 5.35 | 3.02E−06 |
| ENSG00000106366 | SERPINE1 | 4.45 | 5.47E−05 |
| ENSG00000146674 | IGFBP3 | 4.50 | 5.47E−05 |
| ENSG00000123610 | TNFAIP6 | 4.12 | 0.00017735 |
| ENSG00000076706 | MCAM | 4.12 | 0.00026551 |
| ENSG00000135074 | ADAM19 | 4.00 | 0.00032434 |
| ENSG00000140416 | TPM1 | 3.72 | 0.00051342 |
| ENSG00000130707 | ASS1 | 3.81 | 0.00052605 |
| ENSG00000107957 | SH3PXD2A | 3.70 | 0.00063215 |
| ENSG00000187498 | COL4A1 | 3.57 | 0.00080623 |
| ENSG00000139211 | AMIGO2 | 3.61 | 0.00085494 |
| ENSG00000148848 | ADAM12 | 3.58 | 0.00091659 |
| ENSG00000176170 | SPHK1 | 3.54 | 0.00104044 |
| ENSG00000164761 | TNFRSF11B | −3.41 | 0.00130277 |
| ENSG00000149591 | TAGLN | 3.40 | 0.00131241 |
| ENSG00000006016 | CRLF1 | 3.48 | 0.00153949 |
| ENSG00000177283 | FZD8 | 3.46 | 0.00160105 |
| ENSG00000079308 | TNS1 | 3.33 | 0.0021064 |
| ENSG00000099860 | GADD45B | 3.38 | 0.00218565 |
| ENSG00000158186 | MRAS | 3.37 | 0.00231937 |
| ENSG00000211455 | STK38L | 3.30 | 0.00244555 |
| ENSG00000172986 | GXYLT2 | 3.13 | 0.00364601 |
| ENSG00000189184 | PCDH18 | −3.08 | 0.00368398 |
| ENSG00000131435 | PDLIM4 | 3.05 | 0.00385193 |
| ENSG00000106211 | HSPB1 | 3.01 | 0.00438968 |
| ENSG00000170558 | CDH2 | 2.98 | 0.00526545 |
| ENSG00000171793 | CTPS | 3.00 | 0.00558329 |
| ENSG00000139329 | LUM | −2.90 | 0.00567798 |
| ENSG00000113140 | SPARC | 2.88 | 0.00571697 |
| ENSG00000162591 | MEGF6 | 2.95 | 0.00596424 |
| ENSG00000103489 | XYLT1 | 2.97 | 0.00602805 |
| ENSG00000115884 | SDC1 | 2.88 | 0.0072085 |
| ENSG00000163661 | IGFBP7 | 2.72 | 0.00865684 |
| ENSG00000134853 | PDGFRA | −2.70 | 0.00918479 |
| ENSG00000175899 | A2M | −2.68 | 0.00920233 |
| ENSG00000206190 | ATP10A | 2.74 | 0.00933257 |
| ENSG00000163661 | PTX3 | −2.59 | 0.01218007 |
| ENSG00000137809 | ITGA11 | 2.65 | 0.01264373 |
| ENSG00000137124 | ALDH1B1 | 2.70 | 0.01272813 |
| ENSG00000122786 | CALD1 | 2.55 | 0.01365603 |
| ENSG00000127241 | MASP1 | −2.57 | 0.01389162 |
| ENSG00000110328 | GALNTL4 | 2.66 | 0.01464927 |

TABLE 2-continued

Gene Signature with Altered Transcription

| ENSEMBL ID | HGNC ID | log2FC RNA (M)/RNA (Ctrl) | RNA p-value |
|---|---|---|---|
| ENSG00000196923 | PDLIM7 | 2.53 | 0.01542871 |
| ENSG00000025708 | TYMP | 2.59 | 0.01700225 |
| ENSG00000152952 | PLOD2 | 2.45 | 0.01776819 |
| ENSG00000165072 | MAMDC2 | 2.51 | 0.01829777 |
| ENSG00000197594 | ENPP1 | 2.53 | 0.01861632 |
| ENSG00000135919 | SERPINE2 | 2.40 | 0.01922323 |
| ENSG00000135269 | TES | 2.47 | 0.01973346 |
| ENSG00000104368 | PLAT | −2.42 | 0.02041801 |
| ENSG00000129038 | LOXL1 | 2.40 | 0.02049761 |
| ENSG00000128965 | CHAC1 | 2.54 | 0.02099663 |
| ENSG00000198832 | RP3-412A9.11.1 | 2.37 | 0.02162873 |
| ENSG00000115902 | SLC1A4 | 2.50 | 0.02246419 |
| ENSG00000122694 | GLIPR2 | 2.38 | 0.02572646 |
| ENSG00000011422 | PLAUR | 2.33 | 0.02681845 |
| ENSG00000107249 | GLIS3 | 2.37 | 0.02732877 |
| ENSG00000183010 | PYCR1 | 2.28 | 0.02757996 |
| ENSG00000111186 | WNT5B | 2.29 | 0.02786211 |
| ENSG00000162520 | SYNC | 2.35 | 0.02977719 |
| ENSG00000163697 | APBB2 | 2.32 | 0.03055306 |
| ENSG00000100234 | TIMP3 | 2.22 | 0.03067964 |
| ENSG00000106772 | PRUNE2 | 2.31 | 0.03076204 |
| ENSG00000168994 | PXDC1 | 2.23 | 0.03111411 |
| ENSG00000168268 | NT5DC2 | 2.24 | 0.03137418 |
| ENSG00000065054 | SLC9A3R2 | 2.23 | 0.0315624 |
| ENSG00000147224 | PRPS1 | 2.29 | 0.03202045 |
| ENSG00000164465 | DCBLD1 | 2.22 | 0.03220594 |
| ENSG00000130635 | COL5A1 | 2.18 | 0.03264210 |
| ENSG00000171617 | ENC1 | 2.21 | 0.03379284 |
| ENSG00000103257 | SLC7A5 | 2.26 | 0.03503209 |
| ENSG00000175183 | CSRP2 | 2.26 | 0.0350484 |
| ENSG00000154553 | PDLIM3 | 2.21 | 0.03515586 |
| ENSG00000133816 | MICAL2 | 2.15 | 0.03618208 |
| ENSG00000129116 | PALLD | 2.14 | 0.03660141 |
| ENSG00000131711 | MAP1B | 2.20 | 0.03708651 |
| ENSG00000134871 | COL4A2 | 2.11 | 0.03797089 |
| ENSG00000006327 | TNFRSF12A | 2.12 | 0.03816414 |
| ENSG00000108821 | COL1A1 | 2.10 | 0.03826416 |
| ENSG00000187840 | EIF4EBP1 | 2.22 | 0.03834287 |
| ENSG00000165124 | SVEP1 | −2.14 | 0.03854141 |
| ENSG00000105329 | TGFB1 | 2.17 | 0.03974378 |
| ENSG00000106799 | TGFBR1 | 2.10 | 0.03990703 |
| ENSG00000136010 | ALDH1L2 | 2.18 | 0.04014228 |
| ENSG00000147872 | PLIN2 | −2.10 | 0.04036349 |
| ENSG00000171223 | JUNB | 2.10 | 0.04105211 |
| ENSG00000121068 | TBX2 | −2.12 | 0.04242393 |
| ENSG00000164574 | GALNT10 | 2.11 | 0.04286773 |
| ENSG00000165029 | ABCA1 | −2.06 | 0.044136 |
| ENSG00000116016 | EPAS1 | −2.11 | 0.04452792 |
| ENSG00000060982 | BCAT1 | 2.09 | 0.04457308 |
| ENSG00000131981 | LGALS3 | −2.06 | 0.04466942 |
| ENSG00000100139 | MICALL1 | 2.13 | 0.04562388 |
| ENSG00000118523 | CTGF | 2.02 | 0.04636739 |
| ENSG00000065911 | MTHFD2 | 2.03 | 0.0469468 |
| ENSG00000186340 | THBS2 | 2.02 | 0.04716845 |
| ENSG00000117410 | ATP6V0B | 2.03 | 0.04779432 |
| ENSG00000120708 | TGFBI | 2.00 | 0.04817508 |
| ENSG00000173457 | PPP1R14B | 2.02 | 0.0494489 |
| ENSG00000174099 | MSRB3 | 2.10 | 0.04957009 |
| ENSG00000181104 | F2R | −2.00 | 0.04989444 |
| ENSG00000161638 | ITGA5 | 1.99 | 0.05000656 |
| ENSG00000099250 | NRP1 | −2.01 | 0.05023084 |
| ENSG00000173540 | GMPPB | 2.15 | 0.0505729 |
| ENSG00000144655 | CSRNP1 | 2.06 | 0.05123146 |
| ENSG00000092964 | DPYSL2 | −2.02 | 0.05155695 |
| ENSG00000135048 | TMEM2 | 2.01 | 0.05188932 |
| ENSG00000198853 | RUSC2 | 2.03 | 0.05303444 |
| ENSG00000132329 | RAMP1 | 2.02 | 0.05315947 |
| ENSG00000104635 | SLC39A14 | 1.98 | 0.0536051 |
| ENSG00000164932 | CTHRC1 | 1.97 | 0.05405677 |
| ENSG00000112769 | LAMA4 | −1.95 | 0.05420429 |
| ENSG00000134285 | FKBP11 | 2.07 | 0.05432854 |
| ENSG00000145050 | MANF | 1.98 | 0.05494105 |
| ENSG00000134668 | SPOCD1 | 2.06 | 0.05509074 |
| ENSG00000142552 | RCN3 | 1.97 | 0.05510327 |

TABLE 2-continued

Gene Signature with Altered Transcription

| ENSEMBL ID | HGNC ID | log2FC RNA (M)/RNA (Ctrl) | RNA p-value |
|---|---|---|---|
| ENSG00000087008 | ACOX3 | 2.00 | 0.05524263 |
| ENSG00000018510 | AGPS | 2.06 | 0.05540727 |
| ENSG00000163110 | PDLIM5 | 2.00 | 0.05572685 |
| ENSG00000165801 | ARHGEF40 | 1.95 | 0.05592368 |
| ENSG00000070669 | ASNS | 1.96 | 0.05660313 |
| ENSG00000007933 | FMO3 | −2.01 | 0.05694724 |
| ENSG00000156265 | C21orf7 | 2.01 | 0.05708367 |
| ENSG00000165996 | PTPLA | 2.00 | 0.05830933 |
| ENSG00000090520 | DNAJB11 | 2.00 | 0.05899164 |
| ENSG00000152377 | SPOCK1 | 1.95 | 0.05984535 |
| ENSG00000125753 | VASP | 1.95 | 0.06037993 |
| ENSG00000155304 | HSPA13 | 1.92 | 0.06156215 |
| ENSG00000128590 | DNAJB9 | 1.97 | 0.06179333 |
| ENSG00000151327 | FAM177A1 | 1.98 | 0.06266866 |
| ENSG00000138735 | PDE5A | −1.89 | 0.06344404 |
| ENSG00000109861 | CTSC | −1.90 | 0.06413627 |
| ENSG00000163513 | TGFBR2 | −1.91 | 0.06421189 |
| ENSG00000151729 | SLC25A4 | 2.01 | 0.06432535 |
| ENSG00000100600 | LGMN | 1.92 | 0.06502239 |
| ENSG00000113361 | CDH6 | 1.91 | 0.06517739 |
| ENSG00000100596 | SPTLC2 | 1.94 | 0.06546002 |
| ENSG00000144724 | PTPRG | −1.92 | 0.06605951 |
| ENSG00000183963 | SMTN | 1.88 | 0.06648929 |
| ENSG00000147852 | VLDLR | 1.99 | 0.067094 |
| ENSG00000131018 | SYNE1 | 1.86 | 0.06722868 |
| ENSG00000198833 | UBE2J1 | 1.92 | 0.06787646 |
| ENSG00000169756 | LIMS1 | 1.99 | 0.06804636 |
| ENSG00000185000 | DGAT1 | 1.94 | 0.06842024 |
| ENSG00000112096 | SOD2 | −1.90 | 0.06877769 |
| ENSG00000052802 | MSMO1 | 1.93 | 0.06924478 |
| ENSG00000100889 | PCK2 | 1.88 | 0.06938457 |
| ENSG00000136052 | SLC41A2 | 1.96 | 0.07000892 |
| ENSG00000127334 | DYRK2 | 1.91 | 0.07030299 |
| ENSG00000182054 | IDH2 | 1.87 | 0.07097019 |
| ENSG00000122729 | ACO1 | −1.86 | 0.07120481 |
| ENSG00000087303 | NID2 | −1.87 | 0.07131478 |
| ENSG00000162616 | DNAJB4 | 1.92 | 0.07154624 |
| ENSG00000092841 | MYL6 | 1.81 | 0.07161024 |
| ENSG00000156642 | NPTN | 1.84 | 0.07238219 |
| ENSG00000214517 | PPME1 | 1.93 | 0.07294207 |
| ENSG00000101825 | MXRA5 | 1.92 | 0.07301266 |
| ENSG00000198467 | TPM2 | 1.80 | 0.07356735 |
| ENSG00000144810 | COL8A1 | 1.80 | 0.07628075 |
| ENSG00000181019 | NQO1 | −1.80 | 0.07693505 |
| ENSG00000134030 | CTIF | 1.88 | 0.07713563 |
| ENSG00000115380 | EFEMP1 | −1.78 | 0.07802011 |
| ENSG00000196072 | BLOC1S2 | 1.86 | 0.07837829 |
| ENSG00000118508 | RAB32 | 1.78 | 0.07878147 |
| ENSG00000159363 | ATP13A2 | 1.83 | 0.07900456 |
| ENSG00000144746 | ARL6IP5 | −1.87 | 0.08073223 |
| ENSG00000137331 | IER3 | 1.80 | 0.08080819 |
| ENSG00000142871 | CYR61 | 1.77 | 0.08166504 |
| ENSG00000154122 | ANKH | 1.81 | 0.0822588 |
| ENSG00000073712 | FERMT2 | 1.76 | 0.08290623 |
| ENSG00000136802 | LRRC8A | 1.77 | 0.08363724 |
| ENSG00000108106 | UBE2S | 1.84 | 0.08470435 |
| ENSG00000114850 | SSR3 | 1.75 | 0.08485595 |
| ENSG00000239672 | NME1 | 1.82 | 0.08581195 |
| ENSG00000140682 | TGFB1I1 | 1.79 | 0.08583217 |
| ENSG00000196576 | PLXNB2 | −1.73 | 0.0874579 |
| ENSG00000115129 | TP53I3 | 1.75 | 0.08790906 |
| ENSG00000070371 | CLTCL1 | 1.80 | 0.08850262 |
| ENSG00000126524 | SBDS | 1.77 | 0.08865039 |
| ENSG00000198018 | ENTPD7 | 1.81 | 0.08984177 |
| ENSG00000130513 | GDF15 | −1.72 | 0.09015532 |
| ENSG00000166888 | STAT6 | −1.79 | 0.09068891 |
| ENSG00000127418 | FGFRL1 | 1.79 | 0.09101936 |
| ENSG00000167996 | FTH1 | −1.69 | 0.09230109 |
| ENSG00000101955 | SRPX | −1.79 | 0.09230885 |
| ENSG00000115963 | RND3 | −1.70 | 0.09246072 |
| ENSG00000072110 | ACTN1 | 1.70 | 0.09255263 |
| ENSG00000162704 | ARPC5 | 1.69 | 0.09583256 |
| ENSG00000127863 | TNFRSF19 | −1.73 | 0.0958679 |
| ENSG00000161091 | MFSD12 | 1.74 | 0.09725927 |
| ENSG00000198542 | ITGBL1 | 1.68 | 0.09754718 |
| ENSG00000196352 | CD55 | 1.75 | 0.09941386 |
| ENSG00000116260 | QSOX1 | −1.65 | 0.09954164 |

TABLE 3A

Gene Signature (1 replicate) with Altered Translational Efficiency

| ENSEMBL ID | HGNC ID | TE | BABEL p-value |
|---|---|---|---|
| ENSG00000163661 | PTX3 | −2.7413506 | 4.80E−10 |
| ENSG00000182752 | PAPPA | −2.031799 | 1.15E−07 |
| ENSG00000173230 | GOLGB1 | −1.4747045 | 3.65E−07 |
| ENSG00000008441 | NFIX | −1.6325076 | 3.25E−06 |
| ENSG00000108055 | SMC3 | −1.5202935 | 6.61E−06 |
| ENSG00000112902 | SEMA5A | −1.5159033 | 1.90E−05 |
| ENSG00000168724 | DNAJC21 | −1.6152699 | 2.36E−05 |
| ENSG00000138735 | PDE5A | −2.1383717 | 3.96E−05 |
| ENSG00000102908 | NFAT5 | −1.2539722 | 8.13E−05 |
| ENSG00000100644 | HIF1A | 1.29634616 | 8.38E−05 |
| ENSG00000166833 | NAV2 | −1.4353025 | 0.000100353 |
| ENSG00000136542 | GALNT5 | −1.2478982 | 0.000102241 |
| ENSG00000138385 | SSB | −1.276029 | 0.000112036 |
| ENSG00000047410 | TPR | −1.1002148 | 0.000115647 |
| ENSG00000100815 | TRIP11 | −1.253114 | 0.000115691 |
| ENSG00000135905 | DOCK10 | 1.41487073 | 0.000116804 |
| ENSG00000187446 | AC012652.1.1 | 1.4975647 | 0.000169735 |
| ENSG00000108106 | UBE2S | −1.9808659 | 0.000238753 |
| ENSG00000108107 | RPL28 | 1.23778107 | 0.00027262 |
| ENSG00000197442 | MAP3K5 | −2.166021 | 0.000273661 |
| ENSG00000127863 | TNFRSF19 | −1.6203293 | 0.000384143 |
| ENSG00000198121 | LPAR1 | −1.8734643 | 0.000278857 |
| ENSG00000101871 | MID1 | −1.6869885 | 0.000281936 |
| ENSG00000138081 | FBXO11 | −1.2032936 | 0.000367153 |
| ENSG00000111011 | RSRC2 | −1.2385789 | 0.000370672 |
| ENSG00000118058 | MLL | −1.1124833 | 0.000407516 |
| ENSG00000197321 | SVIL | −1.4581886 | 0.000458188 |
| ENSG00000119414 | PPP6C | 1.16868462 | 0.000575527 |
| ENSG00000102241 | HTATSF1 | −1.1116943 | 0.000665853 |
| ENSG00000119408 | NEK6 | −1.5858303 | 0.000679474 |
| ENSG00000144674 | GOLGA4 | −1.1337996 | 0.000700442 |
| ENSG00000008952 | SEC62 | −1.0264219 | 0.000755397 |
| ENSG00000005339 | CREBBP | −1.1959303 | 0.000899463 |
| ENSG00000101972 | STAG2 | −1.1875122 | 0.000970595 |
| ENSG00000173812 | EIF1 | 0.74705692 | 0.001004834 |
| ENSG00000168172 | HOOK3 | 1.12108562 | 0.001093288 |
| ENSG00000151067 | CACNA1C | −1.4996202 | 0.001110948 |
| ENSG00000136819 | C9orf78 | −1.1803341 | 0.001114894 |
| ENSG00000136244 | IL6 | 1.40808063 | 0.0011622 |
| ENSG00000137831 | UACA | −1.0308231 | 0.001200576 |
| ENSG00000126777 | KTN1 | −1.1586794 | 0.00141984 |
| ENSG00000085224 | ATRX | −0.9250079 | 0.00147298 |
| ENSG00000181722 | ZBTB20 | −1.3561731 | 0.001599887 |
| ENSG00000151914 | DST | −1.2345227 | 0.001733711 |
| ENSG00000171793 | CTPS | 1.09773458 | 0.001903283 |
| ENSG00000164692 | RHOBTB3 | −1.7514562 | 0.002363658 |
| ENSG00000018510 | AGPS | −1.1321327 | 0.002431067 |
| ENSG00000148218 | ALAD | −1.1916613 | 0.002478664 |
| ENSG00000170027 | YWHAG | 0.85191988 | 0.002717768 |
| ENSG00000101040 | ZMYND8 | −1.3571925 | 0.002752192 |
| ENSG00000093167 | LRRFIP2 | −1.2205154 | 0.002887031 |
| ENSG00000176105 | YES1 | −1.2351384 | 0.002892828 |
| ENSG00000026025 | VIM | 1.08993981 | 0.003294757 |
| ENSG00000152818 | UTRN | −1.213851 | 0.003490212 |
| ENSG00000167658 | EEF2 | 1.75181457 | 0.003801433 |
| ENSG00000153922 | CHD1 | −0.9896109 | 0.004445999 |
| ENSG00000147677 | EIF3H | 1.33689856 | 0.004466087 |
| ENSG00000135316 | SYNCRIP | −0.8986489 | 0.00454662 |
| ENSG00000105373 | GLTSCR2 | 1.93251408 | 0.004658713 |
| ENSG00000151461 | UPF2 | −1.0525428 | 0.004708017 |
| ENSG00000143374 | TARS2 | −1.2193317 | 0.00478043 |
| ENSG00000114439 | BBX | −1.0539237 | 0.004795963 |
| ENSG00000133318 | RTN3 | 0.84613845 | 0.005442031 |

TABLE 3A-continued

Gene Signature (1 replicate) with Altered Translational Efficiency

| ENSEMBL ID | HGNC ID | TE | BABEL p-value |
|---|---|---|---|
| ENSG00000049618 | ARID1B | -1.0178473 | 0.005566074 |
| ENSG00000197170 | PSMD12 | -0.852153 | 0.005683822 |
| ENSG00000158615 | PPP1R15B | 1.23383146 | 0.005756279 |
| ENSG00000153774 | CFDP1 | -1.1005412 | 0.005942768 |
| ENSG00000188641 | DPYD | -1.2580397 | 0.006287312 |
| ENSG00000136770 | DNAJC1 | 1.03702109 | 0.00652172 |
| ENSG00000121940 | CLCC1 | -1.0098191 | 0.006536917 |
| ENSG00000100154 | TTC28 | -1.0182753 | 0.006608779 |
| ENSG00000113161 | HMGCR | 0.94424256 | 0.006719302 |
| ENSG00000185068 | GTF2H5 | -1.0829484 | 0.006949215 |
| ENSG00000005955 | GGNBP2 | -0.8936361 | 0.00729981 |
| ENSG00000080603 | SRCAP | -0.9154367 | 0.00733119 |
| ENSG00000001497 | LAS1L | -1.0314198 | 0.007743017 |
| ENSG00000138061 | CYP1B1 | -0.8401242 | 0.007885734 |
| ENSG00000164715 | LMTK2 | 1.29018489 | 0.007969877 |
| ENSG00000143545 | RAB13 | -1.0411451 | 0.007980361 |
| ENSG00000026508 | CD44 | 0.68665057 | 0.008092007 |
| ENSG00000117054 | ACADM | -1.0717708 | 0.008211763 |
| ENSG00000092201 | SUPT16H | -0.8692281 | 0.008387717 |
| ENSG00000110367 | DDX6 | -0.879027 | 0.009106782 |
| ENSG00000143904 | EML4 | -0.9889802 | 0.0092973 |
| ENSG00000164294 | GPX8 | 0.89184246 | 0.009363418 |
| ENSG00000241685 | ARPC1A | 1.50567956 | 0.009392258 |
| ENSG00000164548 | TRA2A | 0.93385802 | 0.00952787 |
| ENSG00000138688 | KIAA1109 | -1.0676173 | 0.009640977 |
| ENSG00000100528 | CNIH | 0.8304318 | 0.009829269 |
| ENSG00000127603 | MACF1 | -0.943354 | 0.009856068 |
| ENSG00000115652 | UXS1 | -1.0666256 | 0.0099403 |
| ENSG00000118523 | CTGF | 0.60443779 | 0.010065062 |
| ENSG00000182240 | BACE2 | -1.222017 | 0.01056114 |
| ENSG00000119004 | CYP20A1 | -0.9860759 | 0.011089198 |
| ENSG00000136146 | MED4 | -0.992898 | 0.011091961 |
| ENSG00000124299 | SLC35B3 | -1.1042075 | 0.01133021 |
| ENSG00000077097 | TOP2B | -0.8579402 | 0.011387162 |
| ENSG00000185418 | TARSL2 | -1.1697798 | 0.011458991 |
| ENSG00000125257 | ABCC4 | -1.2299933 | 0.011565549 |
| ENSG00000104419 | NDRG1 | 0.84121291 | 0.012271036 |
| ENSG00000143905 | MEIS1 | -0.9850066 | 0.012417371 |
| ENSG00000112972 | HMGCS1 | 1.04256421 | 0.012443231 |
| ENSG00000164830 | OXR1 | -0.9587293 | 0.013955428 |
| ENSG00000067900 | ROCK1 | -0.8067914 | 0.014145159 |
| ENSG00000122406 | RPL5 | 1.49266971 | 0.01448355 |
| ENSG00000137331 | IER3 | 1.04042945 | 0.014705463 |
| ENSG00000136521 | NDUFB5 | 1.18012704 | 0.014891357 |
| ENSG00000020577 | SAMD4A | -1.0959325 | 0.015243102 |
| ENSG00000180318 | MCFD2 | -0.7756318 | 0.015377781 |
| ENSG00000169100 | SLC25A6 | 1.34004011 | 0.01579095 |
| ENSG00000135047 | CTSL1 | -0.8906545 | 0.016073112 |
| ENSG00000140497 | SCAMP2 | 0.80895096 | 0.016513709 |
| ENSG00000144694 | MRPS5 | -0.9350724 | 0.016712818 |
| ENSG00000132561 | MATN2 | 0.8592783 | 0.016779427 |
| ENSG00000117523 | PRRC2C | -0.5599625 | 0.016819351 |
| ENSG00000118689 | FOXO3 | -1.0512663 | 0.017059692 |
| ENSG00000080345 | RIF1 | -0.7907628 | 0.017236668 |
| ENSG00000105894 | PTN | -0.8244564 | 0.017342288 |
| ENSG00000213949 | ITGA1 | 0.7423431 | 0.017353023 |
| ENSG00000147548 | WHSC1L1 | -0.9352328 | 0.018230486 |
| ENSG00000163946 | FAM208A | -1.0185676 | 0.018771848 |
| ENSG00000106261 | ZKSCAN1 | -1.1775938 | 0.018843712 |
| ENSG00000105193 | RPS16 | 1.10211287 | 0.019637409 |
| ENSG00000139726 | DENR | -0.8974717 | 0.019791894 |
| ENSG00000136205 | TNS3 | -0.8280863 | 0.020242812 |
| ENSG00000145555 | MYO10 | -0.8048733 | 0.021421007 |
| ENSG00000152022 | LIX1L | -0.8124639 | 0.0218285 |
| ENSG00000142669 | SH3BGRL3 | 0.55526839 | 0.021867346 |
| ENSG00000141367 | CLTC | 0.77612663 | 0.022218177 |
| ENSG00000162804 | SNED1 | -0.8185651 | 0.022559585 |
| ENSG00000104408 | EIF3E | 1.32647476 | 0.022886033 |
| ENSG00000110344 | UBE4A | 0.87653113 | 0.023224777 |
| ENSG00000213064 | SFT2D2 | -0.755902 | 0.02323942 |
| ENSG00000225921 | NOL7 | -0.8815621 | 0.023433626 |
| ENSG00000138593 | SECISBP2L | -0.7761533 | 0.023443449 |
| ENSG00000065150 | IPO5 | 0.99464329 | 0.02369603 |
| ENSG00000115806 | GORASP2 | 0.67835655 | 0.023794157 |
| ENSG00000100129 | EIF3L | 1.62687625 | 0.024524439 |
| ENSG00000196914 | ARHGEF12 | -1.1675105 | 0.024891831 |
| ENSG00000204217 | BMPR2 | 0.69246757 | 0.025438073 |
| ENSG00000109390 | NDUFC1 | -0.8952606 | 0.025491324 |
| ENSG00000196367 | TRRAP | -0.7594148 | 0.025604694 |
| ENSG00000144036 | EXOC6B | -1.0757792 | 0.026021627 |
| ENSG00000169946 | ZFPM2 | -1.0479271 | 0.02631718 |
| ENSG00000137509 | PRCP | 0.87652803 | 0.026354393 |
| ENSG00000116747 | TROVE2 | -0.726508 | 0.026552043 |
| ENSG00000060339 | CCAR1 | -0.6997234 | 0.026685169 |
| ENSG00000146247 | PHIP | -0.8332369 | 0.026820782 |
| ENSG00000084652 | TXLNA | 0.73915572 | 0.027068209 |
| ENSG00000130741 | EIF2S3 | 1.05466806 | 0.027133332 |
| ENSG00000150961 | SEC24D | 0.62765591 | 0.027298647 |
| ENSG00000187240 | DYNC2H1 | -1.06679 | 0.027761828 |
| ENSG00000146433 | TMEM181 | -1.0414552 | 0.027796354 |
| ENSG00000179295 | PTPN11 | -0.9140165 | 0.0288127 |
| ENSG00000113282 | CLINT1 | -0.711755 | 0.028973307 |
| ENSG00000171198 | JMJD1C | -0.7790863 | 0.028992676 |
| ENSG00000090054 | SPTLC1 | 0.83148984 | 0.029632806 |
| ENSG00000197579 | TOPORS | -0.8458666 | 0.029699333 |
| ENSG00000142864 | SERBP1 | -0.7646724 | 0.029899373 |
| ENSG00000034713 | GABARAPL2 | 0.68823059 | 0.029970584 |
| ENSG00000090520 | DNAJB11 | -0.7810914 | 0.0300775 |
| ENSG00000166855 | CLPX | -0.8488647 | 0.030097263 |
| ENSG00000135046 | ANXA1 | 0.86394566 | 0.030138772 |
| ENSG00000196935 | SRGAP1 | -0.8040381 | 0.030202802 |
| ENSG00000106538 | RARRES2 | -0.9688629 | 0.030236136 |
| ENSG00000099783 | HNRNPM | -0.5956752 | 0.030351889 |
| ENSG00000141458 | NPC1 | 0.74822754 | 0.030844322 |
| ENSG00000177106 | JUN | 0.71000106 | 0.030935017 |
| ENSG00000097021 | ACOT7 | 0.80866661 | 0.031064001 |
| ENSG00000197111 | PCBP2 | 0.68049208 | 0.031080336 |
| ENSG00000100316 | RPL3 | 1.67662485 | 0.03114172 |
| ENSG00000197056 | ZMYM1 | -0.9388698 | 0.031399769 |
| ENSG00000198042 | MAK16 | -0.8940405 | 0.031501821 |
| ENSG00000148396 | SEC16A | 0.58297597 | 0.031545262 |
| ENSG00000260916 | CCPG1 | -0.7102265 | 0.031823744 |
| ENSG00000188191 | PRKAR1B | -1.027972 | 0.032129214 |
| ENSG00000198146 | ZNF770 | -0.8146313 | 0.032249599 |
| ENSG00000107949 | BCCIP | -0.8019017 | 0.032357337 |
| ENSG00000140443 | IGF1R | -0.8736668 | 0.03237335 |
| ENSG00000169738 | DCXR | -1.0509859 | 0.032502003 |
| ENSG00000107017 | PTGDS | -0.5958188 | 0.032502353 |
| ENSG00000101079 | NDRG3 | -0.9225847 | 0.032934071 |
| ENSG00000138095 | LRPPRC | 0.84253686 | 0.03303189 |
| ENSG00000136153 | LMO7 | -0.9201728 | 0.033102447 |
| ENSG00000146109 | ABT1 | -1.1549145 | 0.033713746 |
| ENSG00000136156 | ITM2B | 0.61379782 | 0.033862692 |
| ENSG00000142599 | RERE | -0.8238852 | 0.033895821 |
| ENSG00000154767 | XPC | -0.7641246 | 0.034070785 |
| ENSG00000107819 | SFXN3 | -0.8139634 | 0.034640721 |
| ENSG00000107951 | MTPAP | -0.8791984 | 0.034849044 |
| ENSG00000107862 | GBF1 | 0.63999556 | 0.03505938 |
| ENSG00000113194 | FAF2 | 0.71045312 | 0.035949786 |
| ENSG00000136485 | DCAF7 | -0.6757873 | 0.036070299 |
| ENSG00000189241 | TSPYL1 | 0.7062045 | 0.036103289 |
| ENSG00000138293 | NCOA4 | 0.88765663 | 0.036332045 |
| ENSG00000070371 | CLTCL1 | 1.10443252 | 0.036773077 |
| ENSG00000172954 | LCLAT1 | -0.8524558 | 0.036863783 |
| ENSG00000196683 | TOMM7 | 1.3075298 | 0.037353358 |
| ENSG00000113048 | MRPS27 | 1.0170333 | 0.037417425 |
| ENSG00000113163 | COL4A3BP | -0.7578152 | 0.037499686 |
| ENSG00000170242 | USP47 | -0.8028916 | 0.037635249 |
| ENSG00000127914 | AKAP7 | -0.6744918 | 0.038026974 |
| ENSG00000141279 | NPEPPS | -0.8812721 | 0.038230406 |
| ENSG00000134313 | KIDINS220 | -0.7488098 | 0.038375301 |
| ENSG00000023287 | RB1CC1 | -0.8487863 | 0.03971745 |
| ENSG00000118181 | RPS25 | 1.58310188 | 0.040307595 |
| ENSG00000029363 | BCLAF1 | -0.6873768 | 0.041239905 |
| ENSG00000152332 | UHMK1 | -0.9690309 | 0.041660214 |
| ENSG00000170871 | KIAA0232 | -0.9350598 | 0.041663582 |
| ENSG00000132792 | CTNNBL1 | -0.7352665 | 0.041674551 |
| ENSG00000013441 | CLK1 | -0.9194947 | 0.042371585 |
| ENSG00000169972 | PUSL1 | -1.0350875 | 0.043097174 |
| ENSG00000128591 | FLNC | 0.6848822 | 0.043354638 |
| ENSG00000135931 | ARMC9 | -0.944761 | 0.043425047 |
| ENSG00000128965 | CHAC1 | 0.79389693 | 0.043641321 |

TABLE 3A-continued

Gene Signature (1 replicate) with Altered Translational Efficiency

| ENSEMBL ID | HGNC ID | TE | BABEL p-value |
|---|---|---|---|
| ENSG00000131171 | SH3BGRL | 0.59583837 | 0.043953482 |
| ENSG00000138246 | DNAJC13 | −0.7333811 | 0.044369031 |
| ENSG00000150593 | PDCD4 | −0.6243741 | 0.044464047 |
| ENSG00000129292 | PHF20L1 | −0.7749239 | 0.044871229 |
| ENSG00000104067 | TJP1 | −0.642144 | 0.044883401 |
| ENSG00000171858 | RPS21 | 1.35698428 | 0.044918379 |
| ENSG00000132688 | NES | 0.54614566 | 0.045111901 |
| ENSG00000144713 | RPL32 | 1.55450933 | 0.045432473 |
| ENSG00000103222 | ABCC1 | −0.7216554 | 0.045567887 |
| ENSG00000078699 | CBFA2T2 | −0.9232918 | 0.045900617 |
| ENSG00000179387 | ELMOD2 | 0.77525851 | 0.046344506 |
| ENSG00000131389 | SLC6A6 | −0.6368225 | 0.04645475 |
| ENSG00000122126 | OCRL | 0.69883954 | 0.046768488 |
| ENSG00000115364 | MRPL19 | −0.711517 | 0.047054746 |
| ENSG00000115355 | CCDC88A | −0.6782108 | 0.047073125 |
| ENSG00000048649 | RSF1 | −0.6764684 | 0.047138641 |
| ENSG00000156256 | USP16 | −0.8521086 | 0.047196289 |
| ENSG00000188739 | RBM34 | −0.8515963 | 0.047979658 |
| ENSG00000173726 | TOMM20 | 0.94716704 | 0.048911642 |
| ENSG00000135720 | DYNC1LI2 | −0.713868 | 0.049159881 |
| ENSG00000126945 | HNRNPH2 | 0.68135224 | 0.049532841 |
| ENSG00000105887 | MTPN | 0.61407664 | 0.049580426 |
| ENSG00000141753 | IGFBP4 | −0.6583794 | 0.049591031 |

TABLE 3B

Gene Signature (5 Biological Replicates) with Altered Translational Efficiency

| ENSEMBL ID | HGNC | Log2 TE | BABEL p-value |
|---|---|---|---|
| ENSG00000250479 | CHCHD10 | 2.51943 | 7.09E-12 |
| ENSG00000118473 | SGIP1 | −2.76752 | 1.51E-11 |
| ENSG00000150636 | CCDC102B | −2.97708 | 1.62E-11 |
| ENSG00000122966 | CIT | −3.08447 | 2.07E-11 |
| ENSG00000108107 | RPL28 | 1.869423 | 1.81E-10 |
| ENSG00000143632 | ACTA1 | −2.01787 | 8.62E-10 |
| ENSG00000170681 | MURC | 3.678236 | 6.92E-09 |
| ENSG00000105964 | COMP | 1.317102 | 7.17E-09 |
| ENSG00000173641 | HSPB7 | 1.292289 | 1.04E-08 |
| ENSG00000054654 | SYNE2 | −1.79281 | 3.79E-08 |
| ENSG00000132510 | KDM6B | 1.602992 | 5.15E-08 |
| ENSG00000132170 | PPARG | −3.52005 | 6.11E-08 |
| ENSG00000119508 | NR4A3 | −1.93064 | 7.13E-08 |
| ENSG00000143850 | PLEKHA6 | −2.06925 | 9.33E-08 |
| ENSG00000175505 | CLCF1 | 1.594058 | 1.45E-07 |
| ENSG00000132031 | MATN3 | 1.340341 | 1.85E-07 |
| ENSG00000169100 | SLC25A6 | 1.909395 | 2.02E-07 |
| ENSG00000196616 | ADH1B | −2.79469 | 2.8E-07 |
| ENSG00000197111 | PCBP2 | 1.29269 | 4.67E-07 |
| ENSG00000171408 | PDE7B | −2.78241 | 5.78E-07 |
| ENSG00000137331 | IER3 | 1.702028 | 6.76E-07 |
| ENSG00000049130 | KITLG | −2.02679 | 9.38E-07 |
| ENSG00000139734 | DIAPH3 | 1.658951 | 1.01E-06 |
| ENSG00000167658 | EEF2 | 2.322838 | 1.61E-06 |
| ENSG00000073712 | SNRPA | 1.461712 | 1.69E-06 |
| ENSG00000132122 | SPATA6 | −1.92545 | 3.83E-06 |
| ENSG00000124496 | TRERF1 | −1.89102 | 4.18E-06 |
| ENSG00000162599 | NFIA | −1.2934 | 5.92E-06 |
| ENSG00000222069 | BTBD19 | 1.524069 | 7.57E-06 |
| ENSG00000135480 | KRT7 | 2.000334 | 8.38E-06 |
| ENSG00000105193 | RPS16 | 1.989185 | 8.68E-06 |
| ENSG00000138675 | FGF5 | −1.16325 | 1.03E-05 |
| ENSG00000108551 | RASD1 | 1.836079 | 1.15E-05 |
| ENSG00000066279 | ASPM | −2.175 | 1.26E-05 |
| ENSG00000174279 | EVX2 | 2.887275 | 1.64E-05 |
| ENSG00000145029 | NICN1 | 1.402987 | 1.84E-05 |
| ENSG00000139343 | GAS2L3 | −2.34161 | 1.96E-05 |
| ENSG00000106415 | GLCCI1 | −1.84191 | 0.000026 |
| ENSG00000197442 | MAP3K5 | −2.0153 | 2.66E-05 |
| ENSG00000094963 | FMO2 | −2.14622 | 0.000031 |
| ENSG00000146411 | SLC2A12 | −1.9708 | 4.09E-05 |
| ENSG00000115267 | IFIH1 | −1.41561 | 4.77E-05 |

TABLE 3B-continued

Gene Signature (5 Biological Replicates) with Altered Translational Efficiency

| ENSEMBL ID | HGNC | Log2 TE | BABEL p-value |
|---|---|---|---|
| ENSG00000124749 | COL21A1 | −1.44522 | 5.07E-05 |
| ENSG00000144218 | AFF3 | 1.146175 | 5.18E-05 |
| ENSG00000154262 | ABCA6 | −2.16651 | 5.24E-05 |
| ENSG00000233927 | RPS28 | 1.937376 | 0.000055 |
| ENSG00000136244 | IL6 | 1.369 | 7.79E-05 |
| ENSG00000138735 | PDE5A | −1.59351 | 8.35E-05 |
| ENSG00000187605 | TET3 | 1.540855 | 8.43E-05 |
| ENSG00000125869 | LAMP5 | 1.298433 | 8.54E-05 |
| ENSG00000146066 | HIGD2A | 1.195557 | 9.35E-05 |
| ENSG00000189367 | KIAA0408 | −1.28312 | 0.000103 |
| ENSG00000157168 | NRG1 | 1.162042 | 0.000106 |
| ENSG00000155962 | CLIC2 | −2.39184 | 0.000106 |
| ENSG00000188846 | RPL14 | 1.745447 | 0.000125 |
| ENSG00000137033 | IL33 | −2.48811 | 0.000128 |
| ENSG00000129226 | CD68 | 1.047995 | 0.00014 |
| ENSG00000171793 | CTPS | 1.080465 | 0.000147 |
| ENSG00000152154 | TMEM178 | 2.01577 | 0.000152 |
| ENSG00000117724 | CENPF | −1.23716 | 0.000153 |
| ENSG00000112276 | BVES | 1.172691 | 0.00016 |
| ENSG00000131747 | TOP2A | −1.31413 | 0.000181 |
| ENSG00000134419 | RPS15A | 2.194763 | 0.000184 |
| ENSG00000128016 | ZFP36 | 1.187628 | 0.000188 |
| ENSG00000135390 | ATP5G2 | 1.380759 | 0.000188 |
| ENSG00000049192 | ADAMTS6 | 2.862797 | 0.000209 |
| ENSG00000105373 | GLTSCR2 | 2.066729 | 0.000211 |
| ENSG00000115268 | RPS15 | 1.300314 | 0.000224 |
| ENSG00000124406 | ATP8A1 | −2.12205 | 0.000228 |
| ENSG00000168769 | TET2 | 1.37689 | 0.000237 |
| ENSG00000166441 | RPL27A | 2.090323 | 0.000237 |
| ENSG00000168916 | ZNF608 | −1.58959 | 0.00024 |
| ENSG00000147677 | EIF3H | 1.328509 | 0.000247 |
| ENSG00000198121 | LPAR1 | −1.44836 | 0.000253 |
| ENSG00000198932 | GPRASP1 | −1.23921 | 0.000259 |
| ENSG00000104408 | EIF3E | 1.469386 | 0.000287 |
| ENSG00000198848 | CES1 | 1.084318 | 0.000306 |
| ENSG00000133321 | RARRES3 | −1.99537 | 0.000312 |
| ENSG00000122406 | RPL5 | 1.592522 | 0.000392 |
| ENSG00000070756 | PABPC1 | 1.207052 | 0.000397 |
| ENSG00000135486 | HNRNPA1 | 1.08564 | 0.000404 |
| ENSG00000137628 | DDX60 | −1.21094 | 0.000417 |
| ENSG00000164292 | RHOBTB3 | −1.52866 | 0.000434 |
| ENSG00000133687 | TMTC1 | −1.90695 | 0.000441 |
| ENSG00000204628 | GNB2L1 | 1.732459 | 0.000477 |
| ENSG00000171858 | RPS21 | 1.846388 | 0.00048 |
| ENSG00000182899 | RPL35A | 1.626674 | 0.000484 |
| ENSG00000144713 | RPL32 | 1.915935 | 0.000484 |
| ENSG00000198963 | RORB | −1.76565 | 0.000505 |
| ENSG00000109846 | CRYAB | 1.107197 | 0.000535 |
| ENSG00000177600 | RPLP2 | 1.69427 | 0.000538 |
| ENSG00000156508 | EEF1A1 | 1.850575 | 0.000545 |
| ENSG00000152818 | UTRN | −1.08497 | 0.00056 |
| ENSG00000244242 | IFITM10 | −1.29903 | 0.000572 |
| ENSG00000154654 | NCAM2 | −1.13535 | 0.000618 |
| ENSG00000129422 | MTUS1 | −1.14926 | 0.000642 |
| ENSG00000155621 | C9orf85 | 1.111901 | 0.000643 |
| ENSG00000097021 | ACOT7 | 1.010887 | 0.000688 |
| ENSG00000050426 | LETMD1 | 1.270162 | 0.000706 |
| ENSG00000229117 | RPL41 | 1.473651 | 0.000712 |
| ENSG00000100316 | RPL3 | 1.780059 | 0.000743 |
| ENSG00000164342 | TLR3 | −1.37101 | 0.000771 |
| ENSG00000169239 | CA5B | −1.79072 | 0.000794 |
| ENSG00000170504 | TMC7 | 1.744989 | 0.000811 |
| ENSG00000185033 | SEMA4B | −1.41345 | 0.000833 |
| ENSG00000147403 | RPL10 | 1.690799 | 0.000923 |
| ENSG00000187240 | DYNC2H1 | −1.22778 | 0.000952 |
| ENSG00000125375 | ATP5S | 1.075005 | 0.000968 |
| ENSG00000184661 | CDCA2 | −1.57267 | 0.001062 |
| ENSG00000171517 | LPAR3 | −2.38727 | 0.001079 |
| ENSG00000026025 | VIM | 1.001738 | 0.001082 |
| ENSG00000109452 | INPP4B | −1.56908 | 0.001104 |
| ENSG00000197756 | RPL37A | 2.028577 | 0.001124 |
| ENSG00000110700 | RPS13 | 1.538546 | 0.00115 |
| ENSG00000088367 | EPB41L1 | 1.018214 | 0.001179 |
| ENSG00000152527 | PLEKHH2 | −1.38949 | 0.00121 |
| ENSG00000064042 | LIMCH1 | −1.22217 | 0.001224 |

TABLE 3B-continued

Gene Signature (5 Biological Replicates) with Altered Translational Efficiency

| ENSEMBL ID | HGNC | Log2 TE | BABEL p-value |
|---|---|---|---|
| ENSG00000100575 | TIMM9 | 1.113218 | 0.001229 |
| ENSG00000121957 | GPSM2 | −1.40775 | 0.001239 |
| ENSG00000118898 | PPL | −1.53977 | 0.00126 |
| ENSG00000197958 | RPL12 | 1.878187 | 0.001271 |
| ENSG00000087586 | AURKA | −1.73649 | 0.001312 |
| ENSG00000118181 | RPS25 | 1.697268 | 0.001415 |
| ENSG00000089351 | GRAMD1A | 1.068576 | 0.001647 |
| ENSG00000129675 | ARHGEF6 | −1.10045 | 0.001654 |
| ENSG00000171425 | ZNF581 | 1.450193 | 0.001733 |
| ENSG00000175315 | CST6 | 1.241221 | 0.001753 |
| ENSG00000138182 | KIF20B | −1.28121 | 0.001776 |
| ENSG00000139209 | SLC38A4 | −1.14245 | 0.00181 |
| ENSG00000163219 | ARHGAP25 | 1.165653 | 0.00184 |
| ENSG00000125967 | NECAB3 | 1.402793 | 0.001844 |
| ENSG00000148303 | RPL7A | 1.650224 | 0.001928 |
| ENSG00000125744 | RTN2 | −1.14254 | 0.001929 |
| ENSG00000189180 | ZNF33A | −1.05822 | 0.002062 |
| ENSG00000170889 | RPS9 | 1.6139 | 0.002078 |
| ENSG00000063177 | RPL18 | 1.611619 | 0.002079 |
| ENSG00000128854 | APOBEC3F | −1.12736 | 0.002113 |
| ENSG00000100784 | RPS6KA5 | −1.43095 | 0.002244 |
| ENSG00000174748 | RPL15 | 1.253839 | 0.002262 |
| ENSG00000197959 | DNM3 | −1.16065 | 0.002439 |
| ENSG00000182405 | PGBD4 | 1.055482 | 0.002447 |
| ENSG00000109475 | RPL34 | 1.607573 | 0.002479 |
| ENSG00000176020 | AMIGO3 | −1.31388 | 0.002484 |
| ENSG00000138336 | TET1 | 1.853326 | 0.00249 |
| ENSG00000185854 | SH3BGR | 1.121445 | 0.002612 |
| ENSG00000163931 | TKT | 1.142358 | 0.002636 |
| ENSG00000146757 | ZNF92 | −1.23798 | 0.002664 |
| ENSG00000198182 | ZNF607 | −1.10762 | 0.002724 |
| ENSG00000171987 | RPS7 | 1.549128 | 0.002765 |
| ENSG00000241685 | ARPC1A | 1.287518 | 0.00277 |
| ENSG00000088756 | ARHGAP28 | −1.02406 | 0.002782 |
| ENSG00000156482 | RPL30 | 1.622306 | 0.002854 |
| ENSG00000153707 | PTPRD | −1.18636 | 0.002863 |
| ENSG00000128849 | CGNL1 | −1.02286 | 0.002892 |
| ENSG00000231500 | RPS18 | 2.003068 | 0.002929 |
| ENSG00000145592 | RPL37 | 1.808138 | 0.003002 |
| ENSG00000105640 | RPL18A | 1.669484 | 0.003009 |
| ENSG00000127863 | TNFRSF19 | −1.09317 | 0.003027 |
| ENSG00000139372 | TDG | 1.024894 | 0.003073 |
| ENSG00000104205 | SGK3 | −1.01117 | 0.003075 |
| ENSG00000170962 | PDGFD | −1.02886 | 0.003142 |
| ENSG00000162244 | RPL29 | 1.588943 | 0.003207 |
| ENSG00000172053 | QARS | 1.361835 | 0.003231 |
| ENSG00000151773 | CCDC122 | −1.00405 | 0.003236 |
| ENSG00000131469 | RPL27 | 1.518506 | 0.003252 |
| ENSG00000174444 | RPL4 | 1.688063 | 0.003284 |
| ENSG00000120156 | TEK | −1.65221 | 0.003299 |
| ENSG00000100129 | EIF3L | 1.429034 | 0.003336 |
| ENSG00000138326 | RPS24 | 1.443788 | 0.003411 |
| ENSG00000113272 | THG1L | 1.155349 | 0.003452 |
| ENSG00000169330 | KIAA1024 | 2.216185 | 0.003475 |
| ENSG00000175390 | EIF3F | 1.290244 | 0.003503 |
| ENSG00000169231 | THBS3 | 1.187649 | 0.00351 |
| ENSG00000183765 | CHEK2 | −1.45694 | 0.003579 |
| ENSG00000134532 | SOX5 | −1.66694 | 0.003634 |
| ENSG00000130255 | RPL36 | 1.410987 | 0.003671 |
| ENSG00000184702 | 5-Sep | 1.209162 | 0.003794 |
| ENSG00000104529 | EEF1D | 1.61919 | 0.003976 |
| ENSG00000164653 | RPS14 | 1.683901 | 0.003995 |
| ENSG00000161016 | RPL8 | 1.352789 | 0.00415 |
| ENSG00000109674 | NEIL3 | −2.63009 | 0.004174 |
| ENSG00000138449 | SLC40A1 | 1.114207 | 0.004183 |
| ENSG00000142541 | RPL13A | 1.796824 | 0.004254 |
| ENSG00000184588 | PDE4B | −2.02072 | 0.004281 |
| ENSG00000155816 | FMN2 | −1.24637 | 0.004306 |
| ENSG00000163584 | RPL22L1 | 1.012263 | 0.004479 |
| ENSG00000089289 | IGBP1 | 1.26553 | 0.004627 |
| ENSG00000138356 | AOX1 | −1.14295 | 0.004762 |
| ENSG00000108932 | SLC16A6 | −1.3497 | 0.004807 |
| ENSG00000204520 | MICA | 1.143447 | 0.004864 |
| ENSG00000142937 | RPS8 | 1.610846 | 0.004896 |
| ENSG00000113070 | HBEGF | 1.088046 | 0.004959 |
| ENSG00000145741 | BTF3 | 1.130214 | 0.005066 |
| ENSG00000248905 | FMN1 | −1.90638 | 0.00514 |
| ENSG00000083845 | RPS5 | 1.532714 | 0.005184 |
| ENSG00000198918 | RPL39 | 1.535891 | 0.005218 |
| ENSG00000105372 | RPS19 | 1.549677 | 0.005369 |
| ENSG00000163682 | RPL9 | 1.613142 | 0.005382 |
| ENSG00000142676 | RPL11 | 1.396155 | 0.005383 |
| ENSG00000165171 | WBSCR27 | 1.116069 | 0.005577 |
| ENSG00000111640 | GAPDH | 1.262613 | 0.005634 |
| ENSG00000117543 | DPH5 | 1.114344 | 0.005946 |
| ENSG00000137154 | RPS6 | 1.598032 | 0.005993 |
| ENSG00000143947 | RPS27A | 1.275373 | 0.006092 |
| ENSG00000170275 | CRTAP | 1.021832 | 0.006428 |
| ENSG00000075651 | PLD1 | −1.03241 | 0.006527 |
| ENSG00000111678 | C12orf57 | 1.172975 | 0.006548 |
| ENSG00000172809 | RPL38 | 1.353068 | 0.006956 |
| ENSG00000130741 | EIF2S3 | 1.067385 | 0.00704 |
| ENSG00000125691 | RPL23 | 1.603975 | 0.007277 |
| ENSG00000196683 | TOMM7 | 1.126267 | 0.007329 |
| ENSG00000178401 | DNAJC22 | −1.18938 | 0.00741 |
| ENSG00000136040 | PLXNC1 | −1.0996 | 0.007562 |
| ENSG00000090376 | IRAK3 | −1.01671 | 0.007597 |
| ENSG00000198755 | RPL10A | 1.509807 | 0.007598 |
| ENSG00000114391 | RPL24 | 1.304469 | 0.007667 |
| ENSG00000071082 | RPL31 | 1.599814 | 0.007781 |
| ENSG00000213741 | RPS29 | 1.570822 | 0.007815 |
| ENSG00000186184 | POLR1D | 1.229911 | 0.007848 |
| ENSG00000161970 | RPL26 | 1.654815 | 0.007913 |
| ENSG00000198467 | TPM2 | 1.077188 | 0.008168 |
| ENSG00000115392 | FANCL | −1.23269 | 0.008213 |
| ENSG00000137818 | RPLP1 | 1.460829 | 0.008299 |
| ENSG00000187987 | ZSCAN23 | −1.04823 | 0.008574 |
| ENSG00000197728 | RPS26 | 1.090113 | 0.008582 |
| ENSG00000198034 | RPS4X | 1.533681 | 0.008759 |
| ENSG00000198242 | RPL23A | 1.394537 | 0.009726 |
| ENSG00000204397 | CARD16 | −1.07621 | 0.009841 |
| ENSG00000149273 | RPS3 | 1.517901 | 0.010391 |
| ENSG00000117461 | PIK3R3 | −1.0571 | 0.010612 |
| ENSG00000184254 | ALDH1A3 | −1.32678 | 0.010897 |
| ENSG00000176438 | C14orf49 | −1.04426 | 0.010906 |
| ENSG00000115594 | IL1R1 | −1.00334 | 0.011677 |
| ENSG00000137819 | PAQR5 | −1.44514 | 0.013098 |
| ENSG00000053747 | LAMA3 | −1.23334 | 0.014709 |
| ENSG00000257949 | TEN1 | 1.361387 | 0.014841 |
| ENSG00000175084 | DES | 1.20409 | 0.015111 |
| ENSG00000101639 | CEP192 | −1.19163 | 0.015211 |
| ENSG00000196531 | NACA | 1.082663 | 0.01541 |
| ENSG00000140988 | RPS2 | 1.606507 | 0.015474 |
| ENSG00000156467 | UQCRB | 1.047919 | 0.015711 |
| ENSG00000047648 | ARHGAP6 | −1.08196 | 0.015848 |
| ENSG00000164116 | GUCY1A3 | −1.93203 | 0.015978 |
| ENSG00000180667 | YOD1 | 1.146396 | 0.01633 |
| ENSG00000186468 | RPS23 | 1.302477 | 0.016725 |
| ENSG00000136942 | RPL35 | 1.279749 | 0.017369 |
| ENSG00000250722 | SEPP1 | −1.03545 | 0.01764 |
| ENSG00000139132 | FGD4 | −1.14179 | 0.017942 |
| ENSG00000114942 | EEF1B2 | 1.434033 | 0.018005 |
| ENSG00000215472 | RPL17 | 1.22905 | 0.018135 |
| ENSG00000138134 | STAMBPL1 | −1.13882 | 0.018424 |
| ENSG00000167526 | RPL13 | 1.465152 | 0.018815 |
| ENSG00000196323 | ZBTB44 | −1.22176 | 0.019332 |
| ENSG00000221983 | UBA52 | 1.125432 | 0.020091 |
| ENSG00000177954 | RPS27 | 1.428562 | 0.020692 |
| ENSG00000148082 | SHC3 | −1.54133 | 0.021037 |
| ENSG00000145425 | RPS3A | 1.660815 | 0.021105 |
| ENSG00000163661 | PTX3 | −1.57581 | 0.021121 |
| ENSG00000089009 | RPL6 | 1.106565 | 0.021763 |
| ENSG00000142534 | RPS11 | 1.314223 | 0.02235 |
| ENSG00000254772 | EEF1G | 1.550899 | 0.023278 |
| ENSG00000172809 | RPS12 | 1.642226 | 0.023317 |
| ENSG00000232859 | C17orf108 | −1.32937 | 0.026416 |
| ENSG00000108298 | RPL19 | 1.075199 | 0.027309 |
| ENSG00000111057 | KRT18 | 1.811152 | 0.027619 |
| ENSG00000106789 | CORO2A | 1.211664 | 0.027779 |
| ENSG00000008988 | RPS20 | 1.435033 | 0.030941 |

TABLE 3B-continued

Gene Signature (5 Biological Replicates) with Altered Translational Efficiency

| ENSEMBL ID | HGNC | Log2 TE | BABEL p-value |
|---|---|---|---|
| ENSG00000104321 | TRPA1 | −1.25586 | 0.031417 |
| ENSG00000168028 | RPSA | 1.358592 | 0.031477 |
| ENSG00000081377 | CDC14B | −1.33116 | 0.03257 |
| ENSG00000146966 | DENND2A | −1.15633 | 0.033148 |
| ENSG00000124614 | RPS10 | 1.210967 | 0.035745 |
| ENSG00000138386 | NAB1 | −1.01045 | 0.036666 |
| ENSG00000128602 | SMO | −1.25412 | 0.037773 |
| ENSG00000141837 | CACNA1A | −1.05541 | 0.044943 |
| ENSG00000152413 | HOMER1 | 1.003421 | 0.04711 |
| ENSG00000135749 | PCNXL2 | −1.26064 | 0.048103 |

Some characteristics of these gene signatures, including the identity of the pathway with the highest statistical association for each signature, are listed in Table 4 (while these are the most significant, it is notable that significant association of these gene lists with other pathways were observed).

TABLE 4

Properties of Fibrotic Disorder Gene Signatures from IPA Analysis (Results from Single Representative Experimental Replicate)

| | RNA (Transcriptome) | RPF (Translational Rate) | Translational Efficiency |
|---|---|---|---|
| p-value threshold for differential | 0.1 | 0.05 | 0.05 |
| No. of genes meeting threshold | 194 | 211 | 238 |
| % of total gene set | 4.20% | 4.50% | 5.10% |
| Most significant pathway/category from IPA analysis | Hepatic Fibrosis/ Hepatic Stellate Cell Activation | Hepatic Fibrosis/ Hepatic Stellate Cell Activation | Canonical eIF2 Signaling Pathway |

Figure 4A:
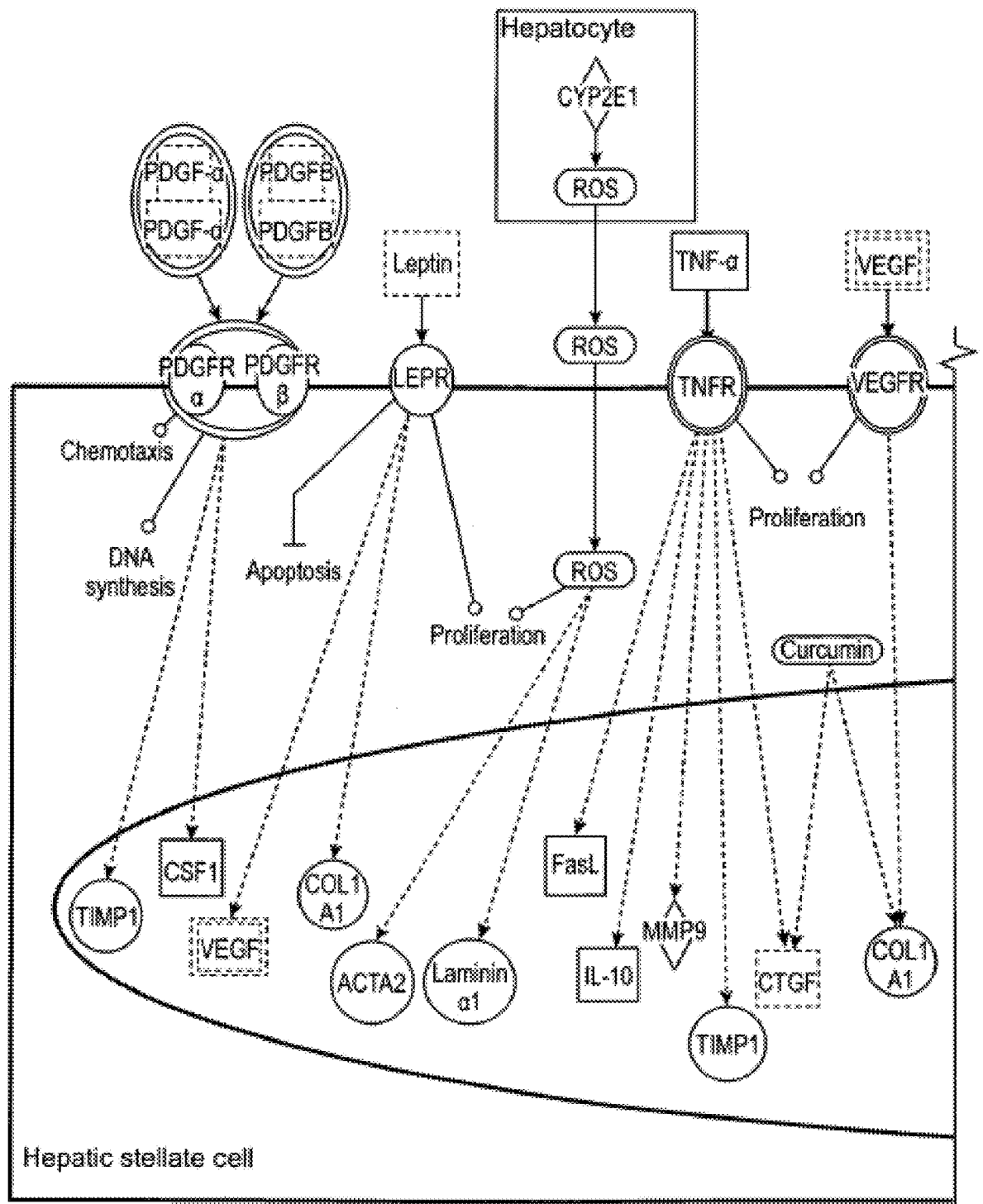
Figure 4B:
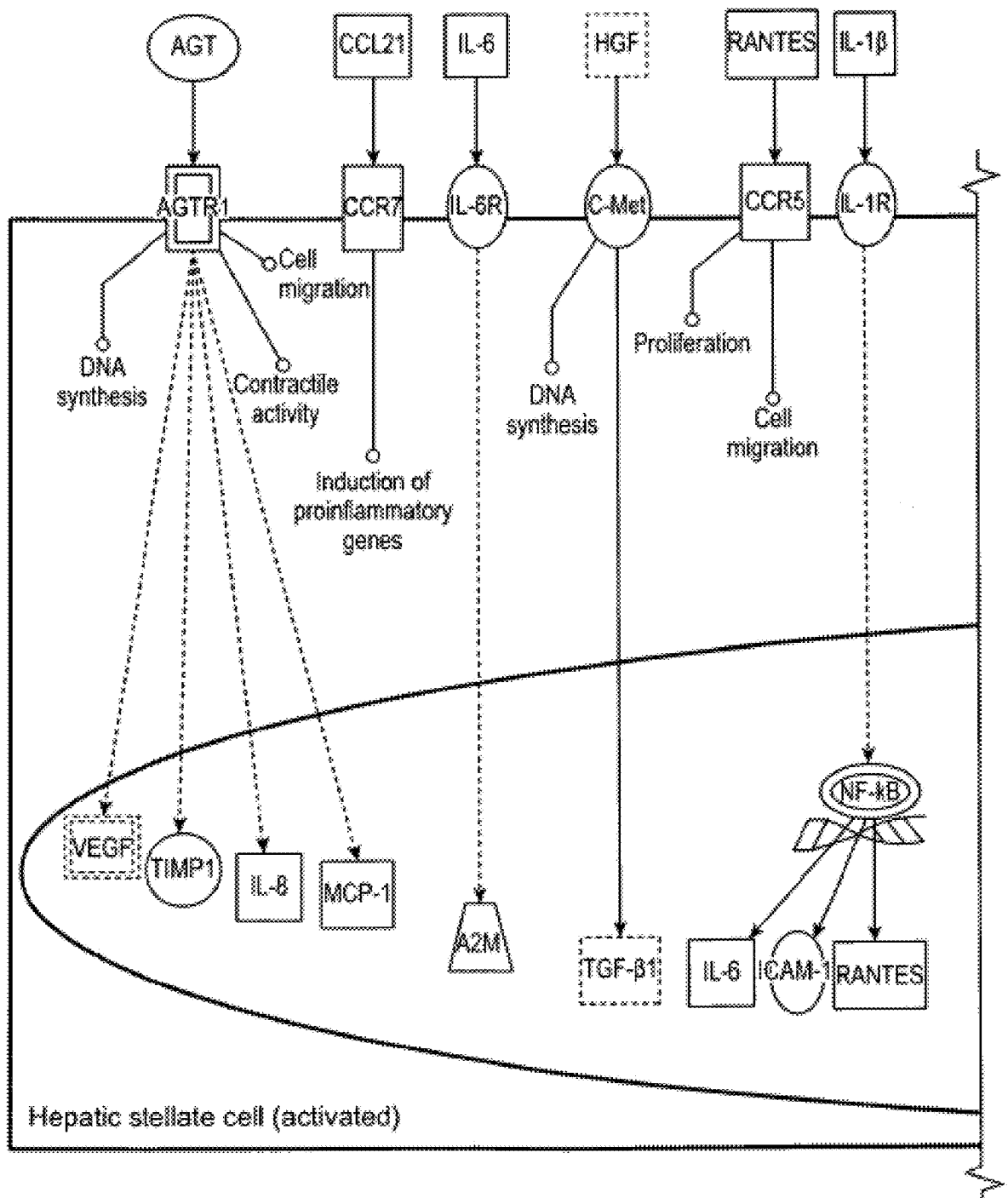
Figure 5A:
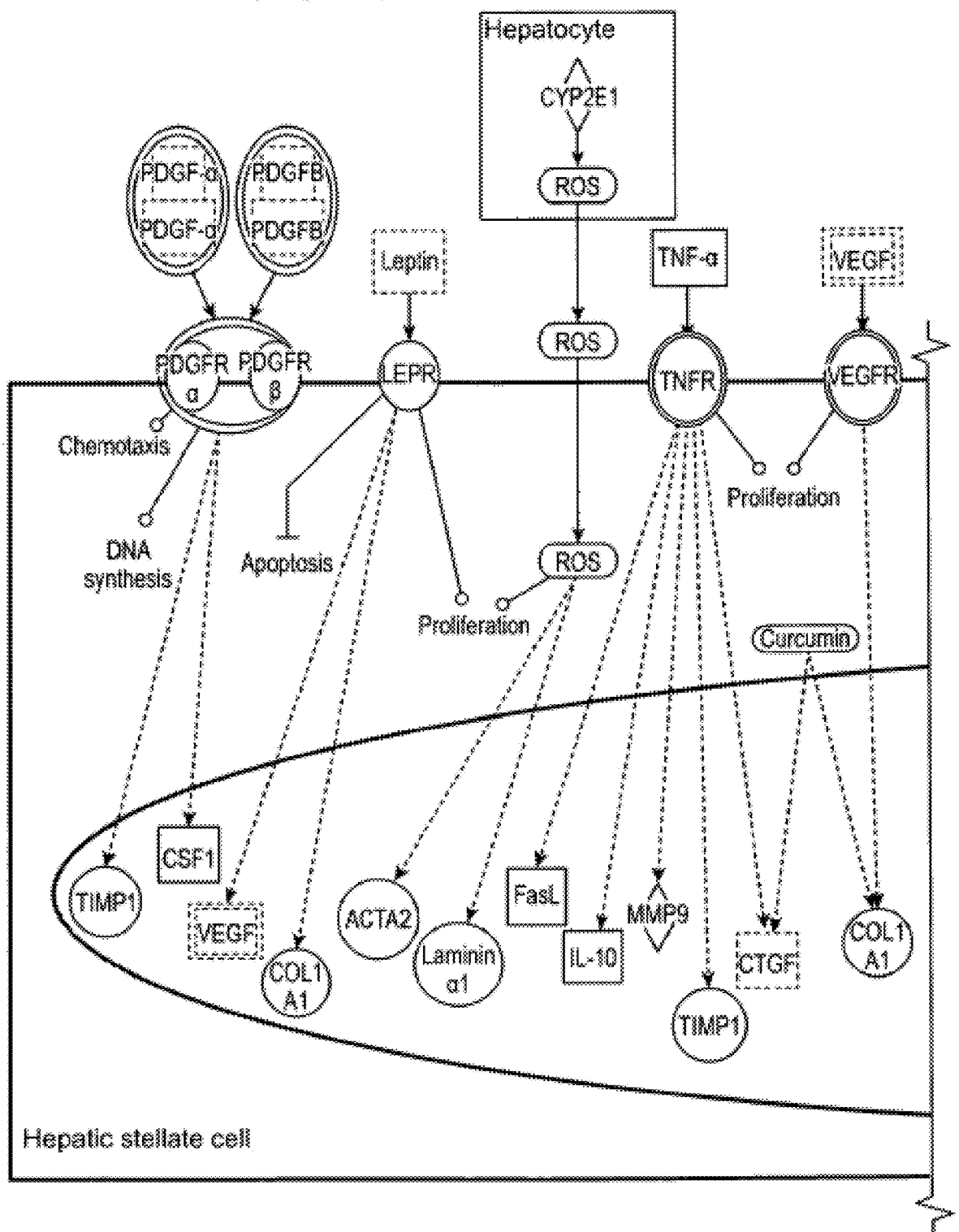
Figure 5B:
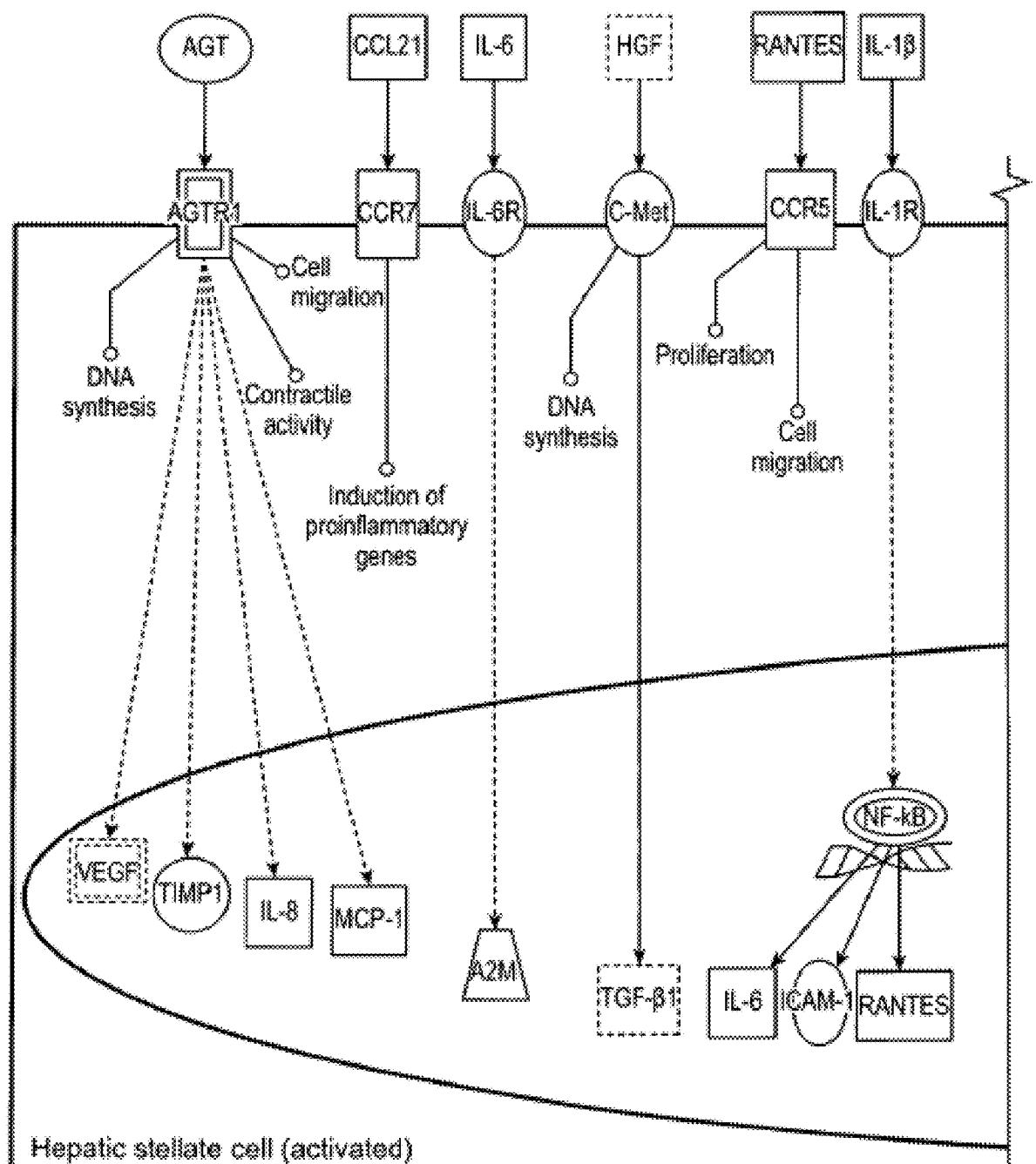
Figure 8:
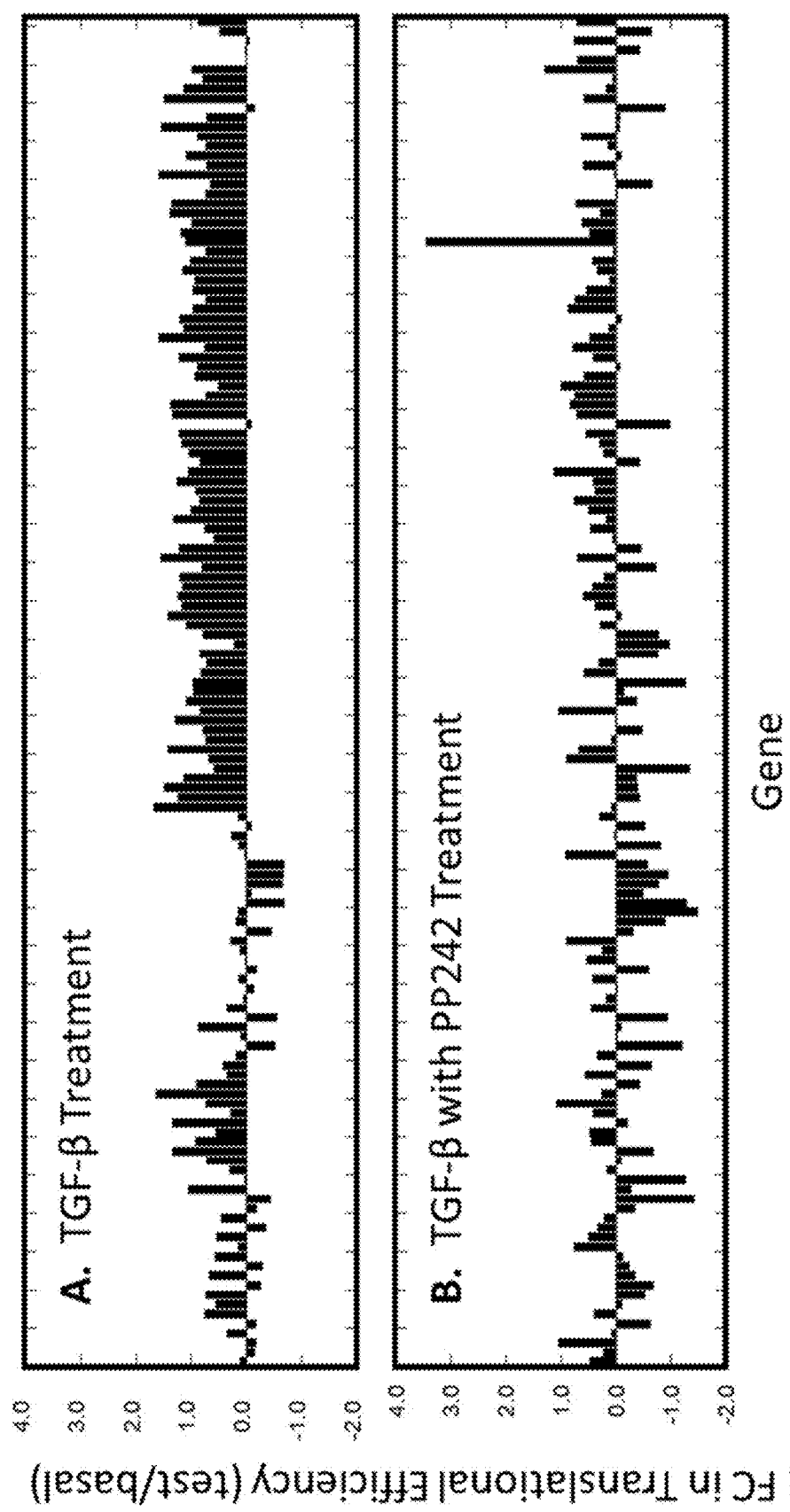
FIG. 8 shows a bar graph of the translational efficiencies of all 141 fibrotic disorder-associated genes (order as presented in Table 5) showing a differential translational profile in (A) TGFβ-treated fibroblasts as compared to untreated (normal) fibroblasts (value set at zero), and (B) how fibroblasts treated with TGFβ and mTOR inhibitor PP242 normalizes (i.e., differential closer to zero) many of the 141 fibrotic disorder-associated genes. The p-value for change in translational efficiency upon TGFβ treatment was ≤0.05 for this gene signature, which is a representative result from a single experimental replicate.

In particular, genes showing changes in RNA levels and translational rates were most strongly associated with Hepatic Fibrosis/Hepatic Stellate Cell Activation (see FIGS. 4 and 5). This action of TGFβ in fibroblasts recapitulates much of the behavior observed in liver fibrosis. In contrast, a 12 gene signature showing a change in translational efficiency was most strongly associated with regulation of eIF2 signaling (FIG. 7). All 12 genes showed a significant increase in translational efficiency (TE) (Table 5; FIGS. 7 and 8), which extends far beyond these genes. For example, 118 of the 141 genes in the pathway evaluable in this study moved in concert, showing an increase in translational efficiency (see Table 5; FIG. 8A). The translational efficiencies of the 141 pathway-associated genes in fibroblasts before treatment with TGFβ were low (mean value −1.70 $\log_2$ relative to population mean); the impact of TGFβ induced transformation was to increase the translational efficiency of many genes in this signature (mean value of signature upon TGFβ treatment was −1.05). Nonetheless, this was still two-fold lower than the overall population and indicates this pathway is a bottleneck in cellular transformation.

TABLE 5

Effect of TGFβ and PP242 Treatment on Translational Efficiency of Genes in Canonical eIF2 Signaling Pathway

| | | | Log$_2$FC TE | |
|---|---|---|---|---|
| Symbol | Entrez Gene Name | p-value[§] | TGF-β | TGF-β + PP242 |
| EIF2C2 | eukaryotic translation initiation factor 2C | 0.849 | 0.12 | 0.49 |
| AKT1 | v-akt murine thymoma viral oncogene homolog 1 | 0.604 | −0.15 | 0.23 |
| AKT2 | v-akt murine thymoma viral oncogene homolog 2 | 0.634 | −0.16 | 1.05 |
| AKT3 | v-akt murine thymoma viral oncogene homolog 3 | 0.734 | 0.35 | 0.09 |
| ATM | ataxia telangiectasia mutated | 0.657 | −0.16 | −0.62 |
| EIF1 | eukaryotic translation initiation factor 1 | 0.001 | 0.75 | 0.40 |
| EIF5 | eukaryotic translation initiation factor 5 | 0.205 | 0.56 | −0.10 |
| EIF2A | eukaryotic translation initiation factor 2A, 65 kDa | 0.137* | 0.74 | −0.51 |
| EIF2AK1 | eukaryotic translation initiation factor 2-alpha kinase 1 | 0.505 | −0.25 | −0.66 |
| EIF2AK3 | eukaryotic translation initiation factor 2-alpha kinase 3 | 0.210 | 0.67 | −0.33 |
| EIF2AK4 | eukaryotic translation initiation factor 2 alpha kinase 4 | 0.484 | −0.28 | −0.22 |
| EIF2B1 | eukaryotic translation initiation factor 2B, subunit 1 alpha, 26 kDa | 0.185 | 0.57 | −0.11 |
| EIF2B2 | eukaryotic translation initiation factor 2B, subunit 2 beta, 39 kDa | 0.825* | 0.16 | 0.77 |
| EIF2B3 | eukaryotic translation initiation factor 2B, subunit 3 gamma, 58 kDa | 0.281 | 0.54 | 0.51 |
| EIF2B4 | eukaryotic translation initiation factor 2B, subunit 4 delta, 67 kDa | 0.366 | −0.35 | 0.34 |
| EIF2B5 | eukaryotic translation initiation factor 2B, subunit 5 epsilon, 82 kDa | 0.432 | 0.46 | 0.22 |
| EIF2S1 | eukaryotic translation initiation factor 2, subunit 1 alpha, 35 kDa | 0.622 | −0.18 | −0.33 |
| EIF2S2 | eukaryotic translation initiation factor 2, subunit 2 beta, 38 kDa | 0.290 | −0.43 | −1.41 |
| EIF2S3 | eukaryotic translation initiation factor 2, subunit 3 gamma, 52 kDa | 0.027* | 1.05 | −0.26 |
| EIF3A | eukaryotic translation initiation factor 3, subunit A | 0.758 | 0.04 | −1.26 |

TABLE 5-continued

Effect of TGFβ and PP242 Treatment on Translational
Efficiency of Genes in Canonical eIF2 Signaling Pathway

| | | | Log$_2$FC TE | |
|---|---|---|---|---|
| Symbol | Entrez Gene Name | p-value§ | TGF-β | TGF-β + PP242 |
| EIF3B | eukaryotic translation initiation factor 3, subunit B | 0.671 | 0.30 | 0.18 |
| EIF3D | eukaryotic translation initiation factor 3, subunit D | 0.239* | 0.71 | −0.08 |
| EIF3E | eukaryotic translation initiation factor 3, subunit E | 0.023* | 1.33 | −0.67 |
| EIF3F | eukaryotic translation initiation factor 3, subunit F | 0.202* | 0.92 | 0.46 |
| EIF3G | eukaryotic translation initiation factor 3, subunit G | 0.513* | 0.55 | 0.48 |
| EIF3H | eukaryotic translation initiation factor 3, subunit H | 0.004* | 1.34 | −0.20 |
| EIF3I | eukaryotic translation initiation factor 3, subunit I | 0.654 | 0.29 | 0.42 |
| EIF3K | eukaryotic translation initiation factor 3, subunit K | 0.267* | 0.73 | 1.09 |
| EIF3L | eukaryotic translation initiation factor 3, subunit L | 0.025* | 1.63 | 0.27 |
| EIF3M | eukaryotic translation initiation factor 3, subunit M | 0.121* | 0.90 | −0.42 |
| EIF4A1 | eukaryotic translation initiation factor 4A1 | 0.659 | 0.35 | 0.58 |
| EIF4A2 | eukaryotic translation initiation factor 4A2 | 0.507 | 0.41 | −0.63 |
| EIF4A3 | eukaryotic translation initiation factor 4A3 | 0.765 | 0.19 | 0.35 |
| EIF4E | eukaryotic translation initiation factor 4E | 0.219 | −0.51 | −1.20 |
| EIF4G1 | eukaryotic translation initiation factor 4 gamma, 1 | 0.725 | 0.10 | −0.01 |
| EIF4G2 | eukaryotic translation initiation factor 4 gamma, 2 | 0.080 | 0.87 | −0.09 |
| EIF4G3 | eukaryotic translation initiation factor 4 gamma, 3 | 0.126 | −0.54 | −0.93 |
| FAU | Finkel-Biskis-Reilly murine sarcoma virus (FBR-MuSV) ubiquitously expressed | 0.718* | 0.35 | 0.47 |
| GRB2 | growth factor receptor-bound protein 2 | 0.874 | 0.05 | 0.19 |
| GSK3B | glycogen synthase kinase 3 beta | 0.741 | −0.13 | −0.01 |
| HRAS | Harvey rat sarcoma viral oncogene homolog | 0.992 | 0.13 | 0.43 |
| MAP2K1 | mitogen-activated protein kinase kinase 1 | 0.630 | −0.18 | −0.59 |
| MAP2K2 | mitogen-activated protein kinase kinase 2 | 0.835 | 0.02 | 0.54 |
| MAPK1 | mitogen-activated protein kinase 1 | 0.799 | 0.12 | 0.25 |
| MAPK3 | mitogen-activated protein kinase 3 | 0.483 | 0.29 | 0.90 |
| MRAS | muscle RAS oncogene homolog | 0.271 | −0.45 | −0.30 |
| NRAS | neuroblastoma RAS viral (v-ras) oncogene homolog | 0.708 | 0.19 | −0.89 |
| PABPC1 | poly(A) binding protein, cytoplasmic 1 | 0.824* | 0.16 | −1.48 |
| PAIP1 | poly(A) binding protein interacting protein 1 | 0.115 | −0.69 | −1.28 |
| PIK3C3 | phosphatidylinositol 3-kinase, catalytic subunit type 3 | 0.770 | −0.09 | −0.50 |
| PIK3C2A | phosphatidylinositol-4-phosphate 3-kinase, catalytic subunit type 2 alpha | 0.116 | −0.64 | −0.77 |
| PIK3CA | phosphatidylinositol-4,5-bisphosphate 3-kinase, catalytic subunit alpha | 0.135 | −0.66 | −0.94 |
| PIK3R4 | phosphoinositide-3-kinase, regulatory subunit 4 | 0.070 | −0.69 | −0.57 |
| PPP1CA | protein phosphatase 1, catalytic subunit, alpha isozyme | 0.907 | 0.04 | 0.92 |
| PPP1CB | protein phosphatase 1, catalytic subunit, beta isozyme | 0.685 | 0.13 | −0.80 |
| PPP1CC | protein phosphatase 1, catalytic subunit, gamma isozyme | 0.583 | 0.27 | 0.04 |
| PPP1R15A | protein phosphatase 1, regulatory subunit 15A | 0.748 | −0.09 | −0.51 |
| RAF1 | v-raf-1 murine leukemia viral oncogene homolog 1 | 0.926 | 0.16 | 0.30 |
| RPL3 | ribosomal protein L3 | 0.031* | 1.68 | 0.09 |
| RPL4 | ribosomal protein L4 | 0.150* | 1.23 | −0.42 |
| RPL5 | ribosomal protein L5 | 0.014* | 1.49 | −0.37 |
| RPL6 | ribosomal protein L6 | 0.093 | 1.13 | −0.36 |
| RPL7 | ribosomal protein L7 | 0.583 | 0.59 | −1.33 |
| RPL8 | ribosomal protein L8 | 0.333* | 0.69 | 0.90 |
| RPL9 | ribosomal protein L9 | 0.117* | 1.41 | 0.69 |
| RPL10 | ribosomal protein L10 | 0.335* | 0.74 | 0.09 |
| RPL11 | ribosomal protein L11 | 0.323* | 0.78 | −0.47 |
| RPL12 | ribosomal protein L12 | 0.123* | 1.28 | 0.02 |
| RPL13 | ribosomal protein L13 | 0.482* | 0.83 | 1.06 |
| RPL14 | ribosomal protein L14 | 0.114* | 1.08 | −0.35 |
| RPL15 | ribosomal protein L15 | 0.092* | 0.95 | −0.14 |
| RPL17 | ribosomal protein L17 | 0.267* | 0.97 | −1.28 |
| RPL18 | ribosomal protein L18 | 0.376* | 0.81 | 0.58 |
| RPL19 | ribosomal protein L19 | 0.283* | 0.71 | 0.31 |
| RPL21 | ribosomal protein L21 | 0.503* | 0.83 | −0.74 |
| RPL22 | ribosomal protein L22 | 0.849 | 0.22 | −0.96 |
| RPL23 | ribosomal protein L23 | 0.363* | 0.79 | −0.78 |
| RPL24 | ribosomal protein L24 | 0.138* | 1.09 | 0.28 |
| RPL26 | ribosomal protein L26 | 0.152* | 1.42 | −0.08 |
| RPL27 | ribosomal protein L27 | 0.099* | 1.17 | 0.38 |
| RPL28 | ribosomal protein L28 | 0.000* | 1.24 | 0.60 |
| RPL29 | ribosomal protein L29 | 0.139* | 1.16 | 0.45 |
| RPL30 | ribosomal protein L30 | 0.125* | 1.20 | 0.22 |
| RPL31 | ribosomal protein L31 | 0.322* | 0.80 | −0.71 |
| RPL32 | ribosomal protein L32 | 0.045 | 1.55 | 0.71 |
| RPL34 | ribosomal protein L34 | 0.098* | 1.21 | −0.44 |
| RPL35 | ribosomal protein L35 | 0.560* | 0.59 | 0.07 |

TABLE 5-continued

Effect of TGFβ and PP242 Treatment on Translational
Efficiency of Genes in Canonical eIF2 Signaling Pathway

| Symbol | Entrez Gene Name | p-value§ | Log₂FC TE | |
|---|---|---|---|---|
| | | | TGF-β | TGF-β + PP242 |
| RPL36 | ribosomal protein L36 | 0.341* | 0.76 | 0.46 |
| RPL37 | ribosomal protein L37 | 0.144* | 1.31 | 0.20 |
| RPL38 | ribosomal protein L38 | 0.143* | 1.00 | 0.50 |
| RPL41 | ribosomal protein L41 | 0.203* | 0.85 | 0.77 |
| RPL10A | ribosomal protein L10a | 0.393* | 0.92 | 0.39 |
| RPL13A | ribosomal protein L13a | 0.233* | 1.26 | 0.42 |
| RPL18A | ribosomal protein L18a | 0.254* | 1.06 | 1.14 |
| RPL22L1 | ribosomal protein L22-like 1 | 0.076* | 0.84 | −0.42 |
| RPL23A | ribosomal protein L23a | 0.226* | 1.03 | 0.23 |
| RPL27A | ribosomal protein L27a | 0.158* | 1.17 | 0.31 |
| RPL35A | ribosomal protein L35a | 0.079* | 1.22 | 0.56 |
| RPL36AL | ribosomal protein L36a-like | 0.792 | −0.08 | −0.99 |
| RPL37A | ribosomal protein L37a | 0.175* | 1.33 | 0.71 |
| RPL7A | ribosomal protein L7a | 0.080* | 1.37 | 0.84 |
| RPLP0 | ribosomal protein, large, P0 | 0.641 | 0.73 | 0.76 |
| RPLP1 | ribosomal protein, large, P1 | 0.546* | 0.50 | 1.00 |
| RPLP2 | ribosomal protein, large, P2 | 0.243* | 0.93 | 0.58 |
| RPS2 | ribosomal protein S2 | 0.441* | 0.88 | −0.07 |
| RPS3 | ribosomal protein S3 | 0.198* | 1.22 | 0.42 |
| RPS5 | ribosomal protein S5 | 0.510* | 0.75 | 0.78 |
| RPS6 | ribosomal protein S6 | 0.079* | 1.59 | 0.48 |
| RPS7 | ribosomal protein S7 | 0.152* | 1.13 | 0.13 |
| RPS8 | ribosomal protein S8 | 0.180* | 1.20 | −0.08 |
| RPS9 | ribosomal protein S9 | 0.288* | 0.97 | 0.87 |
| RPS10 | ribosomal protein S10 | 0.519* | 0.74 | 0.75 |
| RPS11 | ribosomal protein S11 | 0.339* | 0.97 | 0.53 |
| RPS12 | ribosomal protein S12 | 0.500* | 0.94 | 0.12 |
| RPS13 | ribosomal protein S13 | 0.098* | 1.15 | 0.36 |
| RPS14 | ribosomal protein S14 | 0.309* | 1.01 | 0.44 |
| RPS15 | ribosomal protein S15 | 0.096* | 0.74 | 0.06 |
| RPS16 | ribosomal protein S16 | 0.020* | 1.10 | 3.46 |
| RPS18 | ribosomal protein S18 | 0.349* | 1.18 | 0.48 |
| RPS19 | ribosomal protein S19 | 0.321* | 0.99 | 0.61 |
| RPS20 | ribosomal protein S20 | 0.194* | 1.39 | 0.29 |
| RPS21 | ribosomal protein S21 | 0.045* | 1.36 | 0.73 |
| RPS23 | ribosomal protein S23 | 0.415* | 0.74 | −0.02 |
| RPS24 | ribosomal protein S24 | 0.343* | 0.66 | −0.64 |
| RPS25 | ribosomal protein S25 | 0.040* | 1.58 | 0.05 |
| RPS26 | ribosomal protein S26 | 0.242* | 0.71 | 0.60 |
| RPS27 | ribosomal protein S27 | 0.205* | 1.08 | −0.09 |
| RPS28 | ribosomal protein S28 | 0.336* | 0.74 | 0.15 |
| RPS29 | ribosomal protein S29 | 0.329* | 0.89 | 0.64 |
| RPS15A | ribosomal protein S15a | 0.074* | 1.53 | −0.04 |
| RPS27A | ribosomal protein S27a | 0.346* | 0.71 | −0.06 |
| RPS27L | ribosomal protein S27-like | 0.687 | −0.15 | −0.89 |
| RPS3A | ribosomal protein S3A | 0.197* | 1.48 | 0.59 |
| RPS4X | ribosomal protein S4, X-linked | 0.252* | 1.14 | 0.18 |
| RPS4Y1 | ribosomal protein S4, Y-linked 1 | 0.280 | 0.78 | 0.07 |
| RPSA | ribosomal protein SA | 0.407* | 0.99 | 1.30 |
| RRAS | related RAS viral (r-ras) oncogene homolog | 0.965 | 0.00 | 0.70 |
| RRAS2 | related RAS viral (r-ras) oncogene homolog 2 | 0.914 | 0.02 | −0.41 |
| SHC1 | SHC (Src homology 2 domain containing) transforming protein 1 | 0.777 | −0.04 | 0.78 |
| SOS2 | son of sevenless homolog 2 (Drosophila) | 0.419 | 0.49 | −0.63 |
| UBA52 | ubiquitin A-52 residue ribosomal protein fusion product 1 | 0.249* | 0.87 | 0.71 |

§p-value is for the difference between TGFβ-treated and control cells. Gene names in BOLD have p values ≤ 0.05.
*p-values marked with an asterisk have values ≤ 0.05 based upon data from five biological control and five TGFβ-treated replicates.

The linkage of fibroblast transformation by TGFβ to the eIF2 pathway can be identified by changes in translational rate. For example, the mean log₂FC (log₂ fold change) in TE for this set of 141 genes was 0.65 as compared to 0.02 for the overall gene population. The mean change in translational rate was of the same order (0.76 for the 141 genes as compared to 0.24 for the overall gene population). But in this system, the relatively large number of changes in translational rate driven primarily by changes in mRNA levels obscured this relationship. In contrast, there is little evidence of linkage to the eIF2 pathway in the transcriptome data (e.g., mean change was 0.11 for the 141 genes as compared to 0.22 for the overall gene population).

When fibroblasts were treated with TGFβ and the mTOR inhibitor PP242, 11 out of 12 of the subset of genes found to be associated with the eIF2 signaling pathway moved toward the untransformed, normal state (FIG. 7). The mean increase in translational efficiency in these 12 genes caused by TGFβ treatment of fibroblasts was 1.3 log₂, but the presence of PP242 decreased this value to 0.4 log₂. Similar results were seen for all genes in the pathway, wherein 104 of 141 genes moved toward normal (FIG. 8). The mean increase in translational efficiency of these 12 genes in fibroblasts treated with TGFβ was 0.65 log$_2$, while the presence of PP242 decreased this value to 0.09 log$_2$. Clearly, the presence of PP242 maintains the translational efficiencies of the genes in the eIF2 pathway at their normal levels in fibroblasts. Moreover, PP242 inhibition of mTOR directly regulates the translational efficiencies of a number of genes in the eIF2 pathway in other disease cell systems (e.g., prostate (PC3) and colon (SW620) cancer cells). Normalization of this pathway by mTOR inhibitor PP242 is due to substantially inhibiting TGFβ induced transformation of fibroblasts to fibrotic myofibroblasts.

Conclusion

Figure 3:
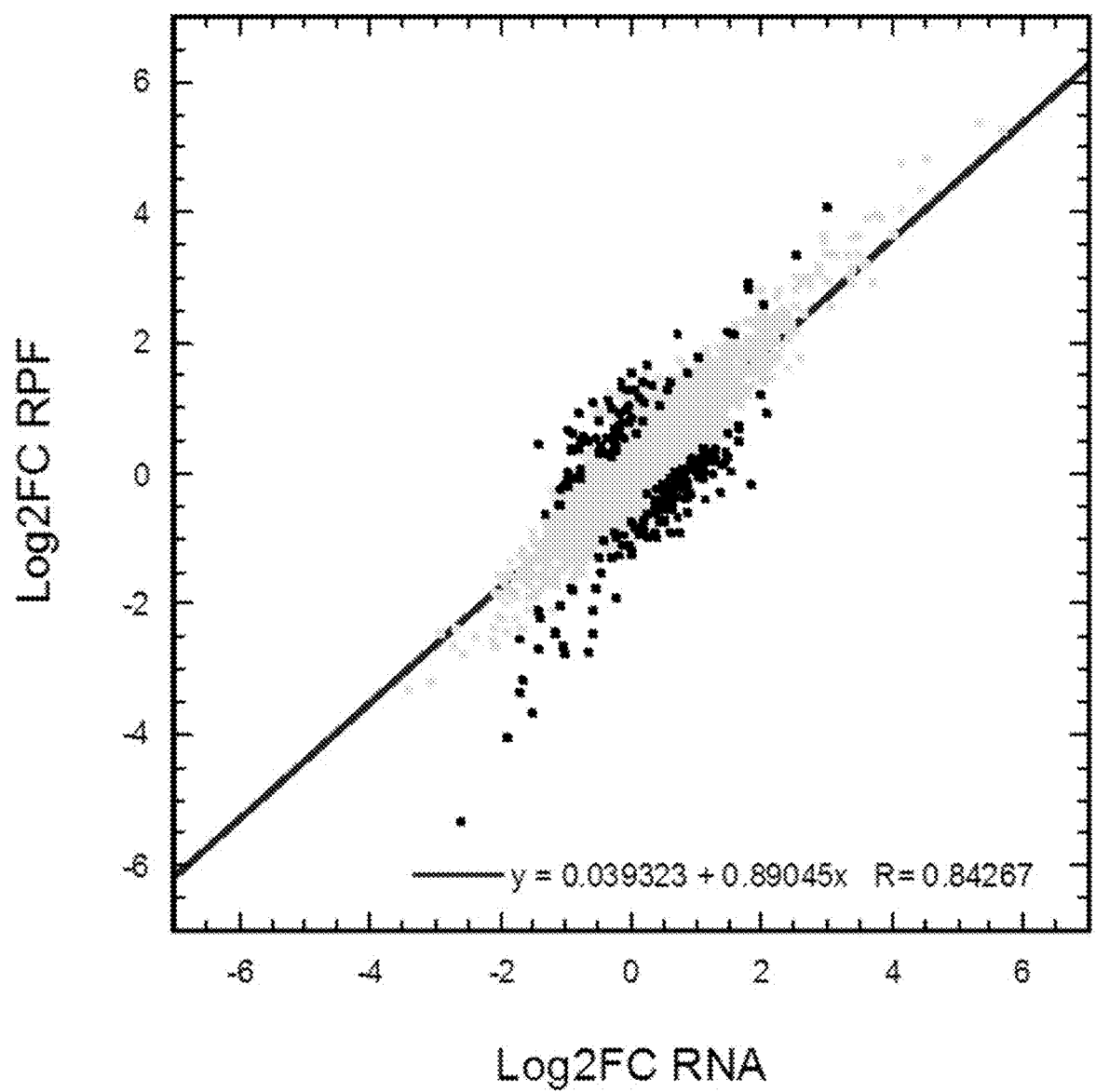
FIG. 3 shows the translational and transcriptional profile of fibroblasts treated with TGFβ. Comparison of changes in mRNA levels (RNA) and translational rate (RPF) in fibroblasts treated with TGFβ. Data points in black have p≤0.05 for changes in translational efficiency.

TGFβ-dependent transformation of fibroblasts to myofibroblasts is known to be driven in large part by transcriptional activation. Here, changes in translational rate and RNA levels on a genome-wide level were shown to be highly correlated (see FIG. 3). In contrast, changes in translational efficiency were relatively independent of transcriptional and translational rate changes. Thus, in this case, measurements of translational efficiency provide a unique window into the cellular biology of fibrotic disorders. Correspondingly, the outcome of pathway analysis based on gene identification via changes in translational efficiency upon TGFβ treatment is quite distinct from analyses based upon transcription or translational rate.

Ribosomal profiling showed that the effect of PP242 on both procollagen and α-SMA were a consequence of preventing fibroblast transformation and transcriptional regulation (instead of a decrease in translation efficiency of mRNA to protein). Specifically, the translational efficiencies of the procollagen and α-SMA were essentially independent of TGFβ and PP242 treatment. Co-administration of TGFβ with mTOR inhibitor PP242 reverses or prevents the changes observed in the eIF2 pathway (i.e., normalizes the translational efficiencies of the genes) and inhibits increased production of fibrotic disorder biomarker proteins, type 1 procollagen and smooth muscle α-actin (which are both hallmarks of TGF-β-mediated fibroblast transformation into myofibroblasts). Although these two biomarkers are only affected at the transcriptional level and not the translational level, they nonetheless provide a means to monitor the pathogenic state of the cell that is mediated by other fibrosis-related genes that are affected at the translational level.

Comparison of translational efficiencies between the normal, healthy state (fibroblasts) and the pathogenic state (fibrotic myofibroblasts induced by TGFβ treatment) identified a novel pathway previously not associated with fibrosis, which is a new insight into a key role of translational efficiency in the pathogenesis of fibrotic disease. Further, an mTOR inhibitor (such as PP242) that modulates this fibrotic disorder-associated pathway and prevents TGFβ-mediated fibroblast to myofibroblast transformation confirms the association of this pathway with fibrotic disease and, thus, shows that components and regulators of this pathway are new targets. The methods of the instant disclosure show that new gene signatures having altered translational profiles (e.g., altered translational efficiency) may be identified using such methods. Furthermore, these data show that an agent or therapeutic that normalizes a translational profile may also be identified. Finally, these data show that targets not previously validated for a particular disorder (in this case, fibrosis), can be identified and validated using the methods of this disclosure.

Example 4

Effect of eIF4A Inhibition on Fibrotic Disease Development

Silvestrol, a cyclopenta[b]benzofuran compound, is a natural product known to inhibit eIF4A, which is the DEAD-box RNA helicase of the eIF4F complex. The TGFβ-mediated transdifferentiation of fibroblasts as described in Example 1 was used as a model to examine whether modulation of eIF4A might have a role in fibrotic disorders.

Briefly, normal human lung fibroblasts (Lonza; cell passage numbers 2 through 5 were used for all experiments) were seeded (Day 0) and cultured in Dulbecco's modified Eagle medium (DMEM) supplemented with 10% fetal bovine serum (FBS), penicillin, streptomycin and glutamax (Invitrogen) at 37° C. in a humidified incubator with 5% CO$_2$ conditions overnight. On Day 1, cells were harvested, washed with phosphate buffered saline (PBS), and then incubated for 48 hours in fresh serum-free DMEM supplemented with penicillin, streptomycin, and glutamax. On Day 3, cells were harvested, resuspended in fresh serum-free DMEM containing silvestrol (1, 5, 10, 75, 100, 500, or 1000 nM) and 10 ng/ml TGFβ, and cultured for 24 hours. Controls included untreated cells and cells treated with only TGFβ.

After this 24 hour incubation, procollagen type 1 levels were measured by collecting culture media, centrifuging to pellet cellular debris, and stored at −80° C. Procollagen Type 1 C-Peptide (PIPC) was quantified using the (PIP) EIA kit (Clontech) according to manufacturer's instructions. The TGFβ-treated fibroblasts of this example are examined by ribosomal profiling (about 6×10$^6$ cells/10 cm plate) and western blot analysis (about 1×10$^6$ cells/well of a 6-well plate).

Results

Figure 9:
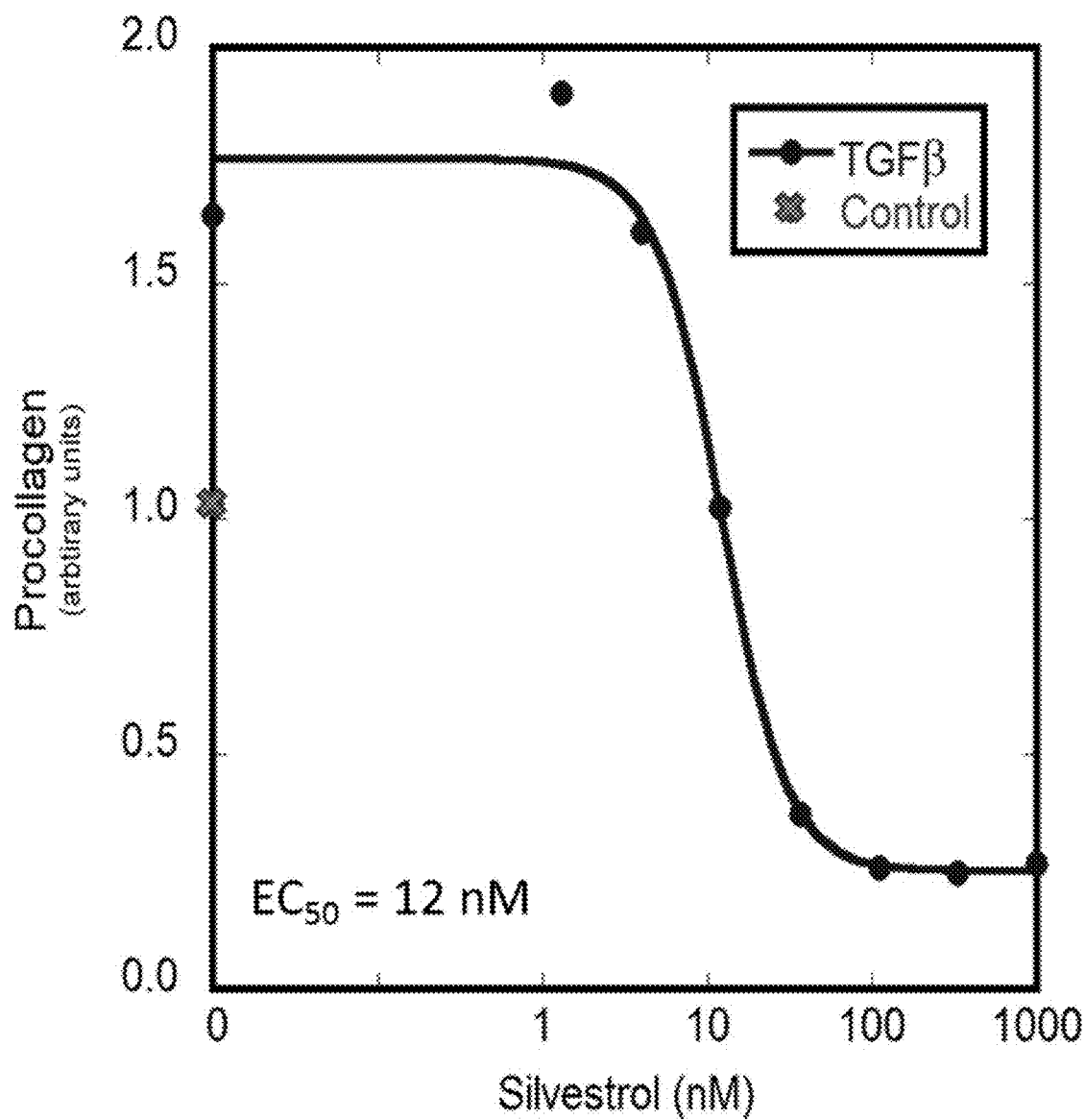
FIG. 9 shows the effect of silvestrol on the induction of procollagen secretion from fibroblasts treated with TGFβ. Procollagen type 1 levels (Procollagen Type 1C-Peptide, "PIPC") were measured after 24 hrs. of treating fibroblasts with various concentrations of eIF4A inhibitor silvestrol and 10 ng/mL TGFβ.
Figure 10:
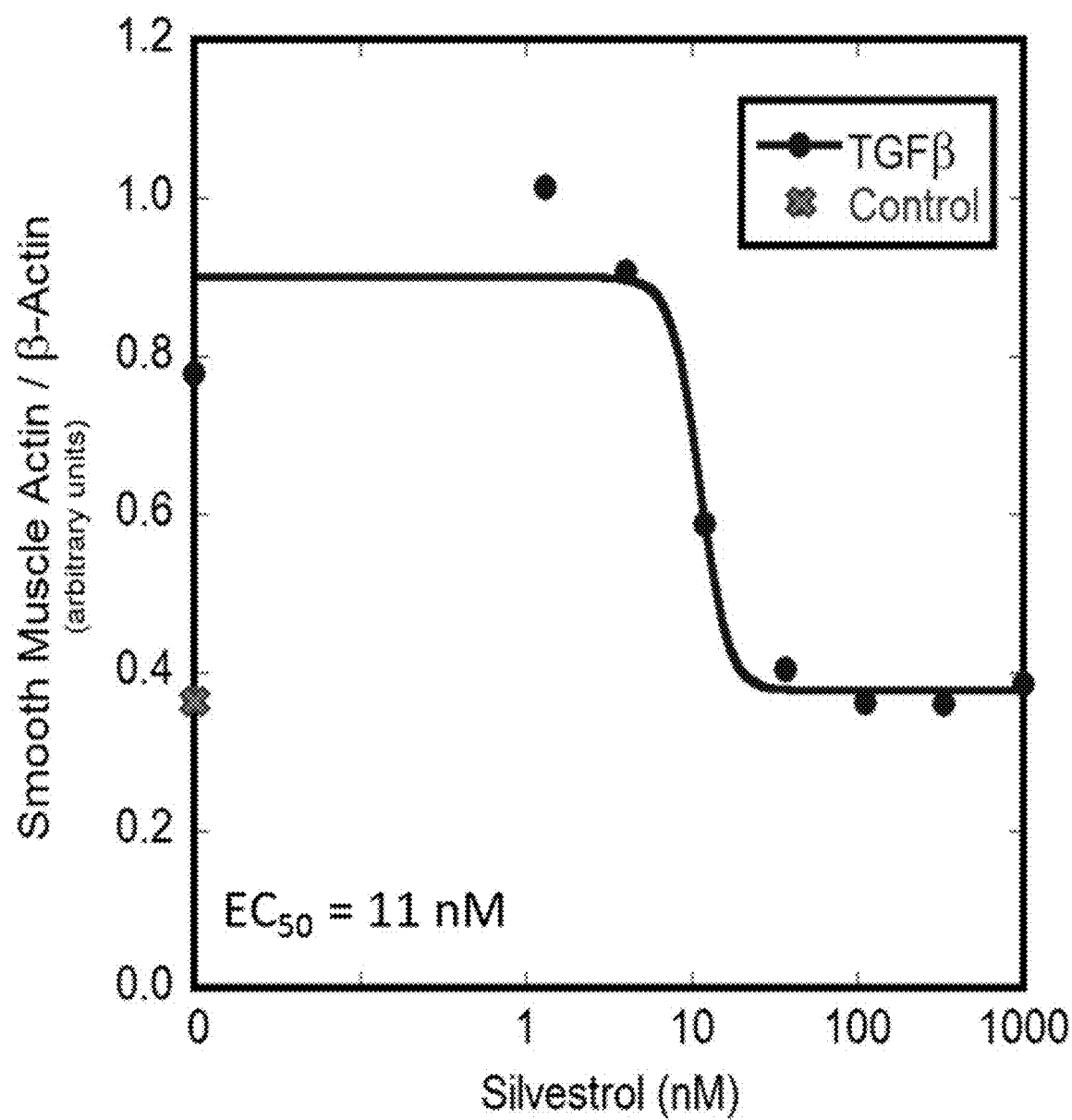
FIG. 10 shows the effect of silvestrol on smooth muscle actin (α-SMA) levels in fibroblasts treated with TGFβ. The ratio of α-SMA to β-actin (control) was measured after 24 hrs. of treating fibroblasts with various concentrations of eIF4A inhibitor silvestrol and 10 ng/mL TGFβ.

Transdifferentiation of fibroblasts into fibrotic myofibroblasts by treatment with TGFβ for 24 hours was accompanied by an approximately 75% increase in procollagen production, while treatment with silvestrol was able to block this increase (EC$_{50}$ of about 12 nM) (FIG. 9). Inhibition of procollagen by silvestrol appears saturable, with the extent of inhibition at higher concentrations reaching about 90% of untreated TGFβ-transformed myofibroblasts (equivalent to about 80% inhibition of untreated, untransformed control fibroblasts). Expression of TGFβ-induced myofibroblast differentiation marker, smooth muscle actin (α-SMA), was also analyzed by western blot analysis. After 24 hours of TGF-β stimulation, increased α-SMA protein levels were detectable, while the level of β-actin did not change. As with procollagen, co-incubation of cells with TGFβ and silvestrol caused a reduction of the α-SMA protein level in a dose dependent manner (EC$_{50}$ of about 11 nM) such that the ratio of α-SMA to β-actin at higher silvestrol concentrations was the same as in untransformed, untreated fibroblasts (FIG. 10).

Conclusion

Co-administration of TGFβ with eIF4A inhibitor silvestrol reverses or prevents the changes observed in a fibrotic disorder-related pathway as evidenced by an inhibition of increased production of fibrotic disorder biomarker proteins, type 1 procollagen and α-smooth muscle actin (which are both hallmarks of TGFβ-mediated fibroblast transdifferentiation into myofibroblasts). While silvestrol is known to have anti-tumor activity (see, e.g., Cencic et al., *PLoS One* 4:e5223, 2009), the usefulness of an eIF4A inhibitor like silvestrol in the treatment of fibrosis was an unexpected result.

Example 5

Effect of siRNA Knockdown of eIF4A on Transdifferentiation of Fibroblasts into Myofibroblasts Normal human lung fibroblasts were seeded (Day 0) and cultured in Dulbecco's modified Eagle medium (DMEM) supplemented with 10% fetal bovine serum (FBS), penicillin, streptomycin and glutamax (Invitrogen) at 37° C. in a humidified incubator with 5% $CO_2$ overnight. On Day 1, cells were washed with phosphate buffered saline (PBS) and then incubated for 24 hours in fresh serum-free DMEM supplemented with penicillin, streptomycin, and glutamax. On Day 2, cells were transfected with siRNA against eIF4A1 (sieIF4A1; sense sequence: GCGAGCCAUUCUACCUU-GUtt (SEQ ID NO.: 5); antisense sequence: ACAAGGUA-GAAUGGCUCGCtg (SEQ ID NO.: 6)) or unrelated control siRNA (siCont) in serum-free DMEM and cultured for 24 hours. On Day 3, serum-free DMEM in the presence or absence of 10 ng/ml TGFβ was added and cultured for an additional 24 hours.

The levels of α-SMA and procollagen type 1, markers of fibroblast transdifferentiation into myofibroblasts and a surrogate for fibrotic disease progression, were measured after a 24 hour incubation of fibroblasts in the presence or absence of TGFβ sieIF4A1 or siCont. The knockdown efficiency was determined by quantitating the eIF4A mRNA level by qPCR (data not shown) and assessing the protein level by western analysis (see FIG. 11).

Figure 12:
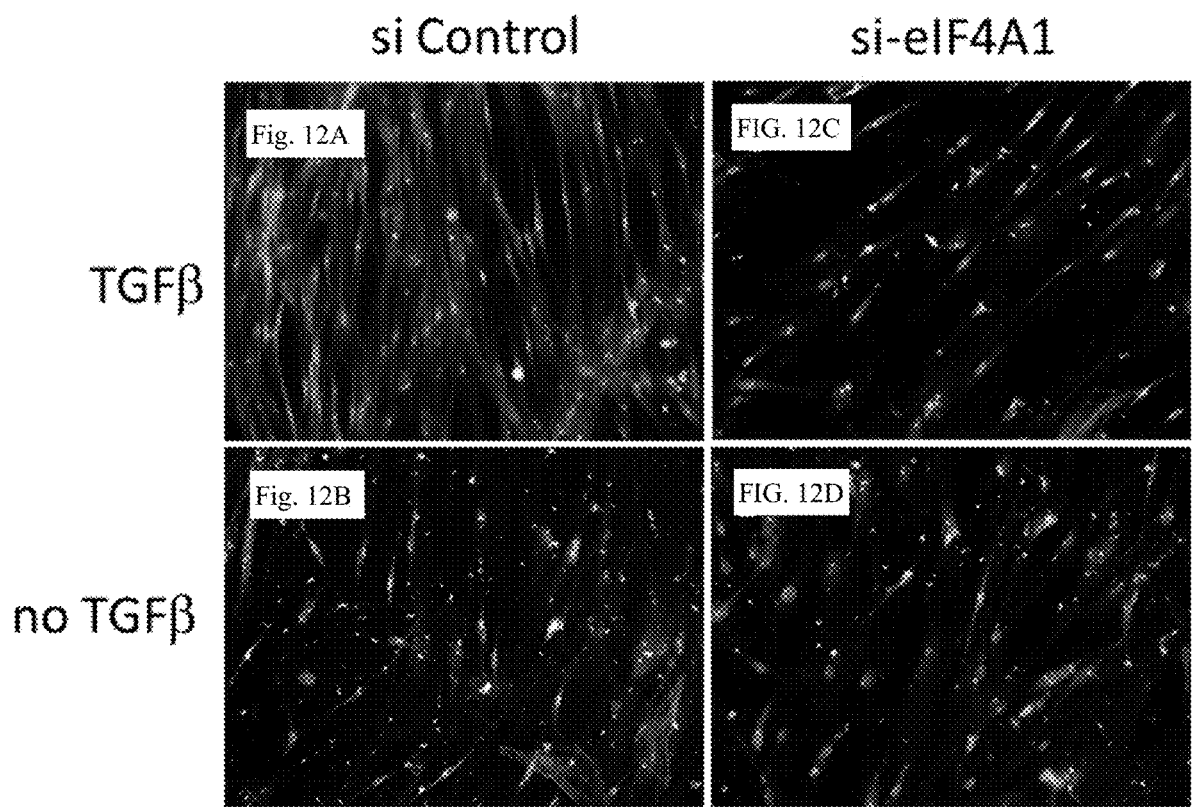
FIGS. 12A to 12D show immunofluorescent staining of α-SMA in fibroblasts and TGFβ transformed myofibroblasts. TGFβ-induced transdifferentiation of fibroblasts into myofibroblasts stimulates an increase in production of α-SMA fibrils (compare A and B). The knockdown of eIF4A prevents TGFβ induced transformation of fibroblasts to myofibroblasts and inhibits of α-SMA production, which essentially eliminates fibril formation (compare A and C). The presence of either siRNA in the absence of TGFβ has no effect on α-SMA production (see B and D).

For the imaging of α-smooth muscle actin and F-actin, normal human lung fibroblasts transfected with siControl or sieIF4A±TGFβ as described above were seeded on coverslips for immunofluorescence microscopy (IF). The following day, cells were washed with PBS, fixed in 4% paraformaldehyde, permeabilized in PBS containing 0.3% Triton X-100®, and blocked in 10% goat serum. To stain for α-smooth muscle actin (α-SMA) and F-actin, coverslips were then incubated with the anti-α-SMA antibody followed by fluorescent conjugated secondary antibody and fluorescent conjugated phalloidin. Finally, coverslips were washed and mounted with mounting media containing DAPI to visualize the nuclei. Immunofluorescence images were captured using the EVOS FL Cell imaging System (Life Technologies) (FIG. 12).

Results

Figure 11:
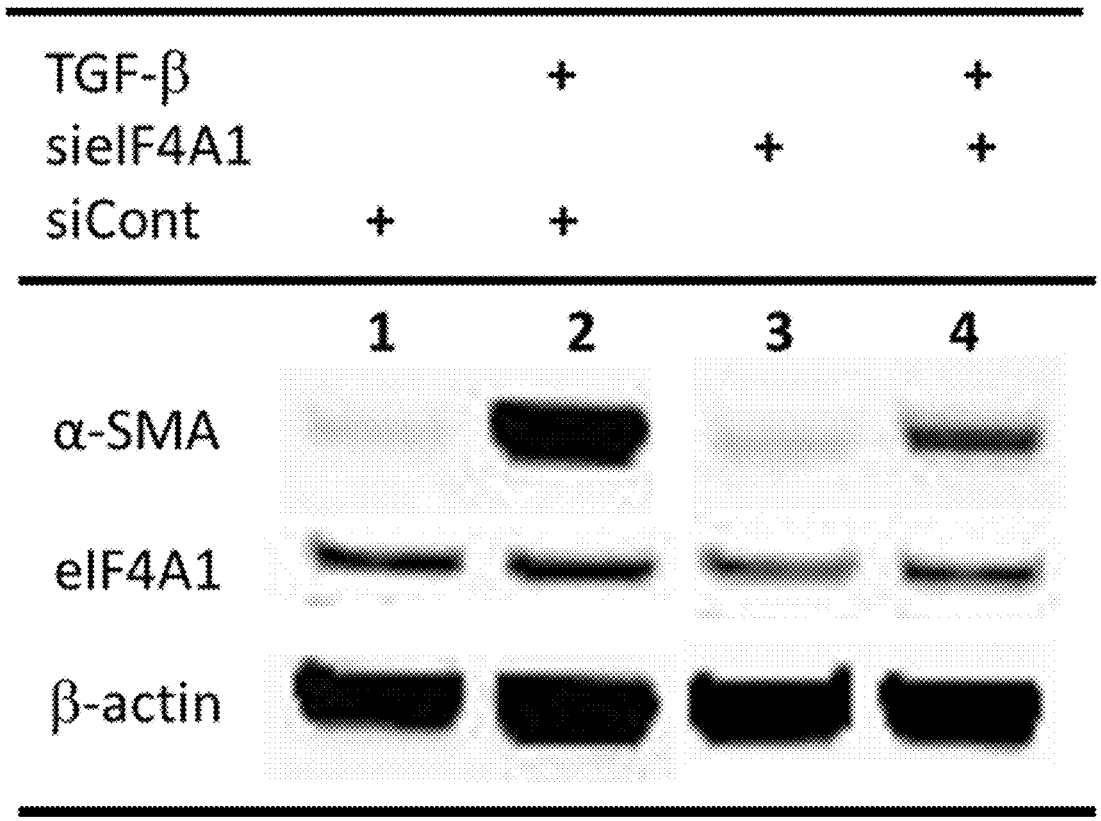
FIG. 11 shows the western blot analysis of α-SMA levels upon fibroblast transformation in the presence of an unrelated siRNA control (siCont) or an siRNA specific for eIF4A1 (sieIF4A1). TGFβ-induces transdifferentiation of fibroblasts into myofibroblasts as shown by the large increase in α-SMA levels (see column 2). The levels of negative control, β-actin, are unaffected by the presence of TGFβ and/or siRNAs. Knockdown of eIF4A expression with siRNA results in a reduced level of α-SMA production by fibroblasts in the presence of TGFβ (compare columns 2 and 4), which essentially prevents fibroblast transdifferentiation into myofibroblasts. The level of eI4A1 mRNA knockdown was about 80%, as measured by qPCR (data not shown). As shown in the western blot, a corresponding decrease in eIF4A1 protein levels was also observed (see columns 3 and 4).

Transdifferentiation of fibroblasts into myofibroblasts by treatment with TGFβ was verified by an increase in production of both α-smooth muscle actin (α-SMA) and procollagen, which was not affected in samples transfected with control siRNA (siCont) alone. In contrast, cells transfected with eIF4A siRNA resulted in approximately 80% knockdown of eIF4A (as determined by either qPCR or western analysis). The specific knockdown of eIF4A with siRNA substantially inhibited TGFβ-induced increases in α-SMA and procollagen levels (FIG. 11).

Examination of cell morphology by immunofluorescent staining of α-SMA shows an increase in α-SMA fibril formation associated with TGFβ-induced transdifferentiation of fibroblasts into myofibroblasts, which appear as long white fibrils with nuclei appearing as white spots in the middle of the fibril (see FIG. 12A). The specific knockdown of eIF4A with siRNA inhibits the TGFβ-induced transdifferentiation of fibroblasts into myofibroblasts, which results in decreased production and staining of α-SMA with primarily only the nuclei visible (see FIG. 12C). The presence of either siRNA in the absence of TGFβ treatment has no effect on the fibroblast phenotype and no effect on α-SMA production (see FIGS. 12B and 12D).

Conclusion

Specific knockdown of the translation initiation target, eIF4A, reverses or prevents the changes observed in a fibrotic disorder-related pathway as evidenced by an inhibition of increased production of fibrotic disorder biomarker proteins, α-smooth muscle actin and type 1 procollagen (which are both hallmarks of TGFβ-mediated fibroblast transdifferentiation into myofibroblasts).

Example 6

Effect of Various Compounds on Fibrotic Disease Development

The TGFβ-mediated transformation of fibroblasts as described in Examples 1 and 4 was used as a model to examine whether compounds known to treat fibrosis as well as compounds with no previously known association with the disease might have a role in treating fibrotic disorders. Compounds shown to be effective at treating fibrosis in vitro and in vivo and tested here include: pirfenidone (5-methyl-1-phenylpyridin-2-one, approved for the treatment of idiopathic pulmonary fibrosis), trichostatin A (TSA, 7-[4-(dimethylamino)phenyl]-N-hydroxy-4,6-dimethyl-7-oxohepta-2,4-dienamide) and rapamycin (an mTOR inhibitor). While pirfenidone has been shown to have antifibrotic and anti-inflammatory properties in various in vitro and in vivo models (Schaefer et al., *Eur. Respir. Rev.* 20:85, 2011), it is unknown what biological molecule is targeted by this drug. TSA inhibits the class I and II histone deacetylase enzymes and has been shown to prevent the accumulation of extracellular matrix in mouse fibrosis models (Huber et al., *Arthritis Rheum.* 56:2755, 2007; Van Beneden et al., *Tox. Appl. Pharma.* 271:276, 2013).

Inhibitors and activators of specific targets with no previously known association with fibrosis were also examined in the TGFβ-mediated fibroblast transformation assay. For example, agents that modulate translation factors were tested, including silvestrol (an eIF4A inhibitor), 1-(benzo[c][1,2,5]oxadiazol-5-yl)-3-(4-chlorophenyl)urea (BOCPU, an activator of eIF2αK), siRNA specific for knocking down eIF4A and eIF4E. In addition, N1-guanyl-1,7-diaminoheptane (GC7), ciclopirox oloamine (CPX), and siRNA specific for knocking down DOHH were tested, which are inhibitors of enzymes that post-translationally modify eIF5A. Also tested was 3-deaza-adenosine (DZA), which indirectly inhibits the enzyme responsible for 5'-cap methylation of mRNA as well as a number of other methylating enzymes. Finally, also evaluated was 2-[(3,5-Difluoro-4-hydroxyphenyl)amino]-7,8-dihydro-5,7-dimethyl-8-(3-methylbutyl)-6(5H)-pteridone (BI-D1870), an inhibitor of the p90 ribosomal s6K enzyme within the RAS/MEK pathway.

TABLE 6

Effect of Various Compounds on Fibrosis Markers

| Target | Translation Factor | Agent | % Renormalization* α-SMA | Collagen |
|---|---|---|---|---|
| — | — | pirfenidone | +++ | +++ |
| Tyrosine kinase inhibitor | — | Nintedanib | +++ | +++ |
| eIF2αK | eIF2α | BOCPU | +++ | ND† |
| eIF4A | eIF4A | Silvestrol | +++ | +++ |

TABLE 6-continued

Effect of Various Compounds on Fibrosis Markers

| Target | Translation Factor | Agent | % Renormalization* | |
|---|---|---|---|---|
| | | | α-SMA | Collagen |
| eIF4A | eIF4A | siRNA†† | +++ | ++ |
| mTOR | eIF4E | PP242 | +++ | +++ |
| eIF4E | eIF4E | siRNA§ | + | ++ |
| mTOR | rpS6 | Rapamycin | + | ++ |
| Deoxyhypusine hydroxylase (DOHH) | eIF5A | CPX | +++ | +++ |
| | | siRNA# | ++ | ++ |
| Histone deacetylase (HDAC) | eIF5A | TSA | ++ | +++ |
| Deoxyhypusine synthase (DHPS) | eIF5A | GC7 | + | + |
| mTOR | rpS6 | Rapamycin | + | ++ |
| p90 Ribosomal S6 kinase (RSK) | rpS6 | BI-D1870 | ++ | +++ |
| Adenosylhomo-cysteinase (AHCY) | Cap methylation | DZA | + | + |

*+ = 0-30%; ++ = 30-60%; +++ = >60%
†Not determined
††80% knockdown of eIF4A target
§70% knockdown of eIF4E target
50% knockdown of DOHH target As shown in the previous examples, transformation of fibroblasts into fibrotic myofibroblasts by treatment with TGFβ for 24 hours was accompanied by an increase in procollagen and smooth muscle actin (α-SMA) production, as measured by ELISA and western blot analysis, respectively. Both PP242 (Example 1) and silvestrol (Example 4) were able to block this increase in procollagen and α-SMA—that is, renormalize production levels of these fibrosis biomarkers (see, also, Table 6). Interestingly, mTOR inhibitors PP242 and rapamycin do not promote renormalization to the same level, which may be due to the different mechanisms of action (rapamycin is an allosteric inhibitor of mTOR, while PP242 is an ATP-competitive inhibitor that directly targets the mTOR catalytic site). The compounds most effective at promoting renormalization of the fibrosis markers in fibroblasts treated with TGFβ (PP242, silvestrol, pirfenidone, CPX, and TSA) were further analyzed by ribosomal profiling as described in Example 3.

Example 7

Translational Profiling: Reversal (Renormalization) of Fibrotic Disease Development Ribosomal profiles of TGFβ-treated fibroblasts in the presence or absence of PP242, silvestrol, pirfenidone, CPX, or TSA individually were prepared in duplicate and analyzed for changes in translational efficiencies as described in Example 3.

Genes showing TGFβ-induced modulation of their translational profiles, including both up and down modulated profiles, as compared to untreated cells are provided in Table 7 (see column labeled "Control vs. TGFβ"). The gene set listed in Table 7 represents those genes having a $\log_2$ fold change in translational efficiency of ≥1 and ≤−1 (translational efficiency p-value ≤0.01).

TABLE 7

Differential Effect of Various Compounds on Translational Renormalization of TGFβ Modulation

| ENSEMBL ID | HGNC ID | Control vs. TGFβ† | Compound‡ | | | | | Exp. (NS)ǁ | | |
|---|---|---|---|---|---|---|---|---|---|---|
| | | | PP242 | Pirfenidone | Silvestrol | CPX | TSA | 1 | 2 | 3 |
| ENSG00000154262 | ABCA6 | A | − | − | ++ | − | − | * | | * |
| ENSG00000097021 | ACOT7 | D | − | − | − | − | − | | | * |
| ENSG00000143632 | ACTA1 | A | − | + | − | + | − | | | * |
| ENSG00000158859 | ADAMTS4 | D | − | − | − | − | − | * | * | |
| ENSG00000154736 | ADAMTS5 | C | − | − | + | + | − | | | |
| ENSG00000049192 | ADAMTS6 | F | − | − | − | − | − | | | |
| ENSG00000176020 | AMIGO3 | C | − | + | − | − | + | | * | * |
| ENSG00000101935 | AMMECR1 | D | − | − | − | − | − | * | * | |
| ENSG00000166839 | ANKDD1A | C | + | + | − | − | − | | | |
| ENSG00000154122 | ANKH | D | − | − | + | − | − | * | | * |
| ENSG00000138356 | AOX1 | B | − | − | − | − | ++ | | | |
| ENSG00000129675 | ARHGEF6 | C | − | − | − | − | − | | | * |
| ENSG00000241685 | ARPC1A | D | − | − | − | − | + | * | | |
| ENSG00000066279 | ASPM | A | + | + | + | − | + | | | * |
| ENSG00000130707 | ASS1 | D | − | − | − | − | − | * | | |
| ENSG00000099624 | ATP5D | D | − | − | − | − | − | | | |
| ENSG00000135390 | ATP5G2 | E | + | + | − | − | − | | | |
| ENSG00000087586 | AURKA | B | − | − | − | − | ++ | | | |
| ENSG00000134897 | BIVM | B | + | − | − | + | − | * | * | |
| ENSG00000145741 | BTF3 | D | − | − | − | − | − | | | |
| ENSG00000111678 | C12orf57 | D | − | − | − | − | + | | | * |
| ENSG00000176438 | C14orf49 | C | − | − | − | − | − | | | |
| ENSG00000104979 | C19orf53 | D | − | − | − | − | − | | | * |
| ENSG00000183172 | C22orf32 | D | − | − | − | − | − | | * | |
| ENSG00000155621 | C9orf85 | D | + | − | − | − | − | | * | |
| ENSG00000169239 | CA5B | B | + | ++ | + | − | + | | | * |
| ENSG00000162545 | CAMK2N1 | C | − | − | − | − | − | * | | |
| ENSG00000204397 | CARD16 | B | − | − | + | − | − | * | * | * |
| ENSG00000150636 | CCDC102B | A | − | ++ | − | − | + | | | |
| ENSG00000101639 | CEP192 | C | − | − | + | − | − | * | | * |
| ENSG00000198848 | CES1 | E | − | − | − | + | − | | | |
| ENSG00000250479 | CHCHD10 | F | +++ | +++ | − | − | − | | | * |

TABLE 7-continued

Differential Effect of Various Compounds on Translational Renormalization of TGFβ Modulation

| ENSEMBL ID | HGNC ID | Control vs. TGFβ† | Compound‡ | | | | | Exp. (NS)‖ | | |
| --- | --- | --- | --- | --- | --- | --- | --- | --- | --- | --- |
| | | | PP242 | Pirfenidone | Silvestrol | CPX | TSA | 1 | 2 | 3 |
| ENSG00000122966 | CIT | A | − | + | +++ | − | +++ | | | |
| ENSG00000175505 | CLCF1 | E | − | − | + | − | + | | | |
| ENSG00000105664 | COMP | E | − | − | − | − | − | | | * |
| ENSG00000106789 | CORO2A | E | − | − | − | − | − | * | | * |
| ENSG00000127184 | COX7C | D | − | − | − | − | − | | * | |
| ENSG00000146592 | CREB5 | D | − | + | − | − | − | | * | |
| ENSG00000109846 | CRYAB | D | − | − | − | − | − | | | |
| ENSG00000171793 | CTPS | D | − | − | − | − | − | | | * |
| ENSG00000137628 | DDX60 | C | − | − | + | − | − | * | | * |
| ENSG00000146966 | DENND2A | C | − | − | − | − | − | * | | * |
| ENSG00000175084 | DES | E | − | − | − | − | − | * | | |
| ENSG00000139734 | DIAPH3 | E | − | ++ | − | − | − | | | |
| ENSG00000178401 | DNAJC22 | B | + | + | − | − | − | | * | * |
| ENSG00000013563 | DNASE1L1 | D | − | − | + | − | − | | * | * |
| ENSG00000117543 | DPH5 | D | − | − | − | − | − | * | * | |
| ENSG00000187240 | DYNC2H1 | B | − | − | ++ | − | − | * | | * |
| ENSG00000078401 | EDN1 | E | − | − | ++ | − | − | * | | |
| ENSG00000156508 | EEF1A1 | E | + | + | − | − | + | | | |
| ENSG00000114942 | EEF1B2 | E | − | − | − | − | − | | | |
| ENSG00000104529 | EEF1D | E | − | − | − | − | − | | | |
| ENSG00000254772 | EEF1G | E | − | − | − | − | − | * | | * |
| ENSG00000167658 | EEF2 | F | + | + | − | − | + | | | |
| ENSG00000130741 | EIF2S3 | D | − | − | − | − | − | * | | |
| ENSG00000104408 | EIF3E | E | + | − | − | − | − | | | |
| ENSG00000175390 | EIF3F | D | − | − | − | − | − | | | |
| ENSG00000147677 | EIF3H | E | − | − | − | − | − | | | |
| ENSG00000100129 | EIF3L | D | − | − | − | − | − | * | | |
| ENSG00000149100 | EIF3M | D | − | − | − | − | − | * | | |
| ENSG00000063046 | EIF4B | E | + | + | − | − | + | * | | |
| ENSG00000088367 | EPB41L1 | D | − | − | + | − | + | | | |
| ENSG00000149806 | FAU | D | − | − | − | − | − | * | | * |
| ENSG00000138675 | FGF5 | B | ++ | + | − | − | − | | | |
| ENSG00000094963 | FMO2 | A | +++ | +++ | − | − | + | | | * |
| ENSG00000151474 | FRMD4A | C | − | − | − | + | + | * | | |
| ENSG00000111640 | GAPDH | E | + | − | − | − | − | | | |
| ENSG00000139354 | GAS2L3 | A | − | − | + | − | + | * | | * |
| ENSG00000107623 | GDF10 | C | − | − | − | + | + | * | | |
| ENSG00000130513 | GDF15 | D | − | − | − | − | − | | | * |
| ENSG00000106415 | GLCCI1 | B | + | + | + | − | + | | | |
| ENSG00000105373 | GLTSCR2 | E | + | + | − | + | + | | | |
| ENSG00000204628 | GNB2L1 | E | + | + | − | − | − | | | |
| ENSG00000121957 | GPSM2 | B | − | − | − | − | ++ | | | |
| ENSG00000113070 | HBEGF | D | − | − | + | − | − | * | | * |
| ENSG00000164588 | HCN1 | D | − | − | − | − | − | | | * |
| ENSG00000146066 | HIGD2A | D | + | + | − | − | − | | | * |
| ENSG00000064393 | HIPK2 | C | − | − | − | − | − | * | | |
| ENSG00000135486 | HNRNPA1 | D | + | − | − | − | − | | | |
| ENSG00000152413 | HOMER1 | D | − | − | + | − | − | * | | * |
| ENSG00000170801 | HTRA3 | C | − | − | − | − | − | * | | |
| ENSG00000137331 | IER3 | E | − | − | − | − | − | | | |
| ENSG00000115267 | IFIH1 | B | + | + | − | − | − | | | * |
| ENSG00000089289 | IGBP1 | E | − | − | − | − | − | * | | |
| ENSG00000163453 | IGFBP7 | E | − | − | − | − | − | | | |
| ENSG00000136244 | IL6 | E | − | − | − | − | − | | | |
| ENSG00000178035 | IMPDH2 | D | − | − | − | − | − | * | | * |
| ENSG00000122641 | INHBA | D | − | − | + | − | − | | | * |
| ENSG00000090376 | IRAK3 | C | − | − | + | − | + | * | | * |
| ENSG00000149596 | JPH2 | F | − | | | | | * | | * |
| ENSG00000089094 | KDM2B | C | − | − | − | − | − | | * | * |
| ENSG00000132510 | KDM6B | E | − | − | + | − | − | | | |
| ENSG00000169330 | KIAA1024 | F | − | − | − | − | − | * | * | |
| ENSG00000049130 | KITLG | A | − | − | − | − | + | | | * |
| ENSG00000135480 | KRT7 | E | − | ++ | − | ++ | − | | | |
| ENSG00000196878 | LAMB3 | D | − | − | + | + | − | * | | |
| ENSG00000125869 | LAMP5 | E | − | − | − | + | − | | | |
| ENSG00000182909 | LENG9 | D | − | − | + | − | − | | | * |
| ENSG00000050426 | LETMD1 | D | − | − | − | − | − | | | |
| ENSG00000100097 | LGALS1 | D | − | + | − | − | − | | | |
| ENSG00000121897 | LIAS | D | − | − | − | − | − | | * | |
| ENSG00000128342 | LIF | D | − | − | − | − | − | * | | * |
| ENSG00000198121 | LPAR1 | C | − | − | − | − | − | | | |
| ENSG00000171517 | LPAR3 | A | − | − | + | − | ++ | * | | * |
| ENSG00000188906 | LRRK2 | C | − | − | − | − | − | * | | * |

TABLE 7-continued

Differential Effect of Various Compounds on Translational Renormalization of TGFβ Modulation

| ENSEMBL ID | HGNC ID | Control vs. TGFβ† | PP242 | Pirfenidone | Silvestrol | CPX | TSA | Exp. (NS)‖ 1 | 2 | 3 |
|---|---|---|---|---|---|---|---|---|---|---|
| ENSG00000197442 | MAP3K5 | B | − | − | − | − | + | | | * |
| ENSG00000132031 | MATN3 | D | − | − | + | − | − | | | |
| ENSG00000112559 | MDFI | A | − | − | − | − | − | | | |
| ENSG00000204520 | MICA | E | − | − | − | − | − | | | |
| ENSG00000174100 | MRPL45 | D | + | − | − | − | − | | * | * |
| ENSG00000129422 | MTUS1 | B | + | ++ | − | − | − | | | |
| ENSG00000170681 | MURC | F | − | − | − | − | + | | | * |
| ENSG00000141140 | MYO19 | D | − | − | + | − | − | * | | * |
| ENSG00000196531 | NACA | E | − | + | − | − | − | | | |
| ENSG00000109065 | NAT9 | D | − | − | − | − | − | | * | |
| ENSG00000125967 | NECAB3 | E | − | − | − | − | − | | * | * |
| ENSG00000136999 | NOV | C | − | − | − | − | + | * | | |
| ENSG00000183971 | NPW | D | − | − | − | − | − | | | * |
| ENSG00000157168 | NRG1 | D | − | − | + | − | − | | | |
| ENSG00000154358 | OBSCN | B | − | − | − | + | +++ | * | | |
| ENSG00000155463 | OXA1L | D | − | − | − | − | − | | * | * |
| ENSG00000089041 | P2RX7 | B | + | ++ | − | ++ | ++ | * | * | |
| ENSG00000070756 | PABPC1 | D | − | − | − | − | − | | | * |
| ENSG00000090621 | PABPC4 | D | − | − | + | − | − | * | | * |
| ENSG00000137819 | PAQR5 | B | − | − | − | + | − | * | | |
| ENSG00000197111 | PCBP2 | E | − | − | + | − | + | | | |
| ENSG00000184588 | PDE4B | B | − | + | +++ | − | + | * | | * |
| ENSG00000138735 | PDE5A | B | − | − | − | − | − | * | | * |
| ENSG00000171408 | PDE7B | A | − | − | + | − | ++ | | | |
| ENSG00000075651 | PLD 1 | B | − | − | ++ | − | − | * | | * |
| ENSG00000052126 | PLEKHA5 | C | − | − | ++ | − | − | * | | * |
| ENSG00000143850 | PLEKHA6 | B | − | − | − | + | + | | | |
| ENSG00000120278 | PLEKHG1 | B | − | − | − | + | − | * | | |
| ENSG00000152527 | PLEKHH2 | B | − | − | − | − | − | * | | * |
| ENSG00000198523 | PLN | F | − | − | − | − | − | | | * |
| ENSG00000102007 | PLP2 | D | − | − | − | − | − | | | |
| ENSG00000186184 | POLR1D | E | − | − | − | − | − | * | * | |
| ENSG00000132170 | PPARG | A | − | +++ | +++ | − | + | | | |
| ENSG00000118898 | PPL | B | − | − | − | − | − | * | | |
| ENSG00000185920 | PTCH1 | D | − | − | − | − | − | * | | * |
| ENSG00000172053 | QARS | D | − | − | − | − | − | | | |
| ENSG00000105514 | RAB3D | B | + | + | − | − | ++ | * | * | |
| ENSG00000133321 | RARRES3 | B | − | − | − | − | − | | | |
| ENSG00000108551 | RASD1 | E | − | − | +++ | − | − | | | * |
| ENSG00000068028 | RASSF1 | D | − | − | − | − | − | | | |
| ENSG00000164292 | RHOBTB3 | B | − | − | − | − | − | * | | * |
| ENSG00000185008 | ROBO2 | C | − | − | − | + | − | * | | |
| ENSG00000166503 | RP11-382A20.3.1 | C | − | − | − | − | − | * | | * |
| ENSG00000147403 | RPL10 | E | − | + | − | − | + | | | |
| ENSG00000198755 | RPL10A | E | − | − | − | − | − | | | |
| ENSG00000142676 | RPL11 | E | − | − | − | − | − | | | |
| ENSG00000197958 | RPL12 | E | − | + | − | − | − | | | |
| ENSG00000167526 | RPL13 | E | − | − | − | − | − | * | | * |
| ENSG00000142541 | RPL13A | E | − | + | − | − | − | | | |
| ENSG00000188846 | RPL14 | E | − | − | − | − | + | | | |
| ENSG00000174748 | RPL15 | D | − | − | − | − | − | | | |
| ENSG00000215472 | RPL17 | E | − | + | − | − | − | | | |
| ENSG00000063177 | RPL18 | E | + | + | − | − | − | | | |
| ENSG00000105640 | RPL18A | E | + | + | − | − | − | | | |
| ENSG00000108298 | RPL19 | D | − | − | − | − | − | * | | * |
| ENSG00000122026 | RPL21 | E | − | + | − | − | − | * | | * |
| ENSG00000163584 | RPL22L1 | D | − | + | − | − | − | | | |
| ENSG00000125691 | RPL23 | E | − | + | − | − | − | | | |
| ENSG00000198242 | RPL23A | E | − | − | − | − | − | * | | * |
| ENSG00000114391 | RPL24 | E | − | − | − | − | − | | | |
| ENSG00000161970 | RPL26 | E | − | + | − | − | − | | | |
| ENSG00000131469 | RPL27 | E | − | − | − | − | − | * | | |
| ENSG00000166441 | RPL27A | F | − | + | − | − | − | | | |
| ENSG00000108107 | RPL28 | E | − | + | − | − | − | | | |
| ENSG00000162244 | RPL29 | E | − | − | − | − | − | | | |
| ENSG00000100316 | RPL3 | E | − | + | − | − | − | | | |
| ENSG00000156482 | RPL30 | E | − | + | − | − | − | | | |
| ENSG00000071082 | RPL31 | E | + | + | − | − | − | | | |
| ENSG00000144713 | RPL32 | E | − | − | − | − | − | | | |
| ENSG00000109475 | RPL34 | E | − | + | − | − | − | | | |
| ENSG00000136942 | RPL35 | E | − | − | − | − | − | | | * |
| ENSG00000182899 | RPL35A | E | + | + | − | − | − | | | |

TABLE 7-continued

Differential Effect of Various Compounds on Translational Renormalization of TGFβ Modulation

| ENSEMBL ID | HGNC ID | Control vs. TGFβ† | Compound‡ | | | | | Exp. (NS)ǁ | | |
|---|---|---|---|---|---|---|---|---|---|---|
| | | | PP242 | Pirfenidone | Silvestrol | CPX | TSA | 1 | 2 | 3 |
| ENSG00000130255 | RPL36 | E | − | + | − | − | − | | | |
| ENSG00000165502 | RPL36AL | D | − | − | − | − | − | | | |
| ENSG00000145592 | RPL37 | E | − | + | − | − | − | | | |
| ENSG00000197756 | RPL37A | E | − | + | − | − | − | | | |
| ENSG00000172809 | RPL38 | E | − | − | − | − | − | * | | |
| ENSG00000198918 | RPL39 | E | − | − | − | − | − | | | |
| ENSG00000174444 | RPL4 | E | − | + | − | − | − | | | |
| ENSG00000229117 | RPL41 | E | − | − | − | − | − | | | * |
| ENSG00000122406 | RPL5 | E | + | + | − | − | − | | | |
| ENSG00000089009 | RPL6 | D | − | − | − | − | − | * | | * |
| ENSG00000148303 | RPL7A | E | − | + | − | − | − | | | |
| ENSG00000161016 | RPL8 | E | − | − | − | − | − | | | |
| ENSG00000163682 | RPL9 | E | − | + | − | − | − | | | |
| ENSG00000089157 | RPLP0 | D | − | − | − | − | − | * | | * |
| ENSG00000137818 | RPLP1 | E | − | + | − | − | − | * | | * |
| ENSG00000177600 | RPLP2 | E | − | + | − | − | − | | | |
| ENSG00000124614 | RPS10 | D | − | + | − | − | − | * | | * |
| ENSG00000142534 | RPS11 | D | − | − | − | − | − | * | | * |
| ENSG00000112306 | RPS12 | E | − | − | − | − | − | * | | * |
| ENSG00000110700 | RPS13 | E | − | − | − | − | − | | | |
| ENSG00000164587 | RPS14 | E | − | − | − | − | − | | | |
| ENSG00000115268 | RPS15 | D | + | + | − | − | − | | | * |
| ENSG00000134419 | RPS15A | F | + | + | − | − | − | | | |
| ENSG00000105193 | RPS16 | F | − | + | − | − | − | | | |
| ENSG00000231500 | RPS18 | E | + | + | − | − | − | | | |
| ENSG00000105372 | RPS19 | E | − | + | − | − | − | | | |
| ENSG00000140988 | RPS2 | E | − | − | − | − | − | * | | * |
| ENSG00000008988 | RPS20 | E | − | − | − | − | − | * | | |
| ENSG00000171858 | RPS21 | E | − | − | − | − | − | | | |
| ENSG00000186468 | RPS23 | E | − | − | − | − | − | | | |
| ENSG00000138326 | RPS24 | E | − | − | − | − | − | | | |
| ENSG00000118181 | RPS25 | E | − | − | − | − | − | | | |
| ENSG00000197728 | RPS26 | D | − | − | − | − | − | | | * |
| ENSG00000177954 | RPS27 | E | − | + | − | − | − | * | | |
| ENSG00000143947 | RPS27A | E | − | − | − | − | − | | | |
| ENSG00000233927 | RPS28 | E | + | + | − | + | − | | | |
| ENSG00000213741 | RPS29 | E | + | + | − | − | − | | | |
| ENSG00000149273 | RPS3 | E | − | − | − | − | − | * | | |
| ENSG00000145425 | RPS3A | E | − | − | − | − | − | * | | * |
| ENSG00000198034 | RPS4X | E | − | − | − | − | − | | | |
| ENSG00000129824 | RPS4Y1 | D | − | − | − | − | − | | | |
| ENSG00000083845 | RPS5 | E | − | + | − | − | − | | | |
| ENSG00000137154 | RPS6 | E | − | − | − | − | − | | | |
| ENSG00000100784 | RPS6KA5 | B | + | − | + | − | − | | | * |
| ENSG00000171863 | RPS7 | E | − | − | − | − | − | | | |
| ENSG00000142937 | RPS8 | E | − | + | − | − | − | | | * |
| ENSG00000170889 | RPS9 | E | − | + | − | − | − | | | |
| ENSG00000168028 | RPSA | D | − | − | − | − | − | * | | * |
| ENSG00000125744 | RTN2 | C | − | − | − | − | − | | | * |
| ENSG00000075213 | SEMA3A | C | − | − | − | − | − | * | | * |
| ENSG00000118473 | SGIP1 | B | − | − | + | − | − | | | * |
| ENSG00000185437 | SH3BGR | D | − | − | − | − | − | | | * |
| ENSG00000148082 | SHC3 | B | − | − | − | +++ | + | * | | |
| ENSG00000110446 | SLC15A3 | B | − | − | − | − | ++ | * | | |
| ENSG00000169100 | SLC25A6 | E | − | + | − | − | − | | | |
| ENSG00000146411 | SLC2A12 | B | − | − | ++ | − | − | * | | * |
| ENSG00000138449 | SLC40A1 | E | − | ++ | − | ++ | + | | | |
| ENSG00000155465 | SLC7A7 | C | − | − | − | − | − | * | | |
| ENSG00000128602 | SMO | C | − | − | − | − | − | * | | * |
| ENSG00000077312 | SNRPA | E | − | − | + | − | − | | | |
| ENSG00000134532 | SOX5 | B | − | − | − | − | + | * | | |
| ENSG00000110693 | SOX6 | E | − | + | − | − | − | | * | |
| ENSG00000132122 | SPATA6 | B | + | + | − | − | − | | | * |
| ENSG00000138134 | STAMBPL1 | C | − | + | + | + | + | * | | * |
| ENSG00000101846 | STS | C | − | + | − | − | − | | * | |
| ENSG00000054654 | SYNE2 | B | − | − | − | − | − | | | |
| ENSG00000166012 | TAF1D | E | − | + | − | − | + | * | | |
| ENSG00000139372 | TDG | D | − | − | − | − | − | | | |
| ENSG00000257949 | TEN1 | E | − | − | + | − | − | | | |
| ENSG00000168769 | TET2 | E | − | − | − | − | − | * | | * |
| ENSG00000187605 | TET3 | E | − | − | − | − | − | * | | |
| ENSG00000120708 | TGFBI | D | − | − | − | − | − | * | | |
| ENSG00000169231 | THBS3 | D | + | + | + | − | − | * | | * |

TABLE 7-continued

Differential Effect of Various Compounds on Translational Renormalization of TGFβ Modulation

| ENSEMBL ID | HGNC ID | Control vs. TGFβ† | Compound‡ | | | | | Exp. (NS)ǁ | | |
| --- | --- | --- | --- | --- | --- | --- | --- | --- | --- | --- |
| | | | PP242 | Pirfenidone | Silvestrol | CPX | TSA | 1 | 2 | 3 |
| ENSG00000113272 | THG1L | D | − | − | − | − | − | * | * | |
| ENSG00000100575 | TIMM9 | D | − | − | − | − | − | | * | |
| ENSG00000163931 | TKT | D | − | + | − | − | − | | | |
| ENSG00000133687 | TMTC1 | B | − | − | +++ | − | + | | | * |
| ENSG00000196683 | TOMM7 | D | − | − | − | + | − | | | * |
| ENSG00000131747 | TOP2A | B | − | − | +++ | − | − | * | | * |
| ENSG00000141933 | TPGS1 | D | − | − | − | − | − | * | | |
| ENSG00000198467 | TPM2 | D | − | − | − | − | − | * | | |
| ENSG00000133112 | TPT1 | D | − | − | − | − | − | * | | * |
| ENSG00000124496 | TRERF1 | B | − | − | + | − | − | | | * |
| ENSG00000221983 | UBA52 | D | − | − | − | − | − | * | | * |
| ENSG00000156467 | UQCRB | E | − | − | − | − | − | | | |
| ENSG00000152818 | UTRN | C | − | − | − | − | − | * | | * |
| ENSG00000026025 | VIM | D | − | − | − | − | − | | | |
| ENSG00000171425 | ZNF581 | E | − | − | − | − | − | | | * |
| ENSG00000168916 | ZNF608 | C | − | − | − | − | + | | | |

Figure 13:
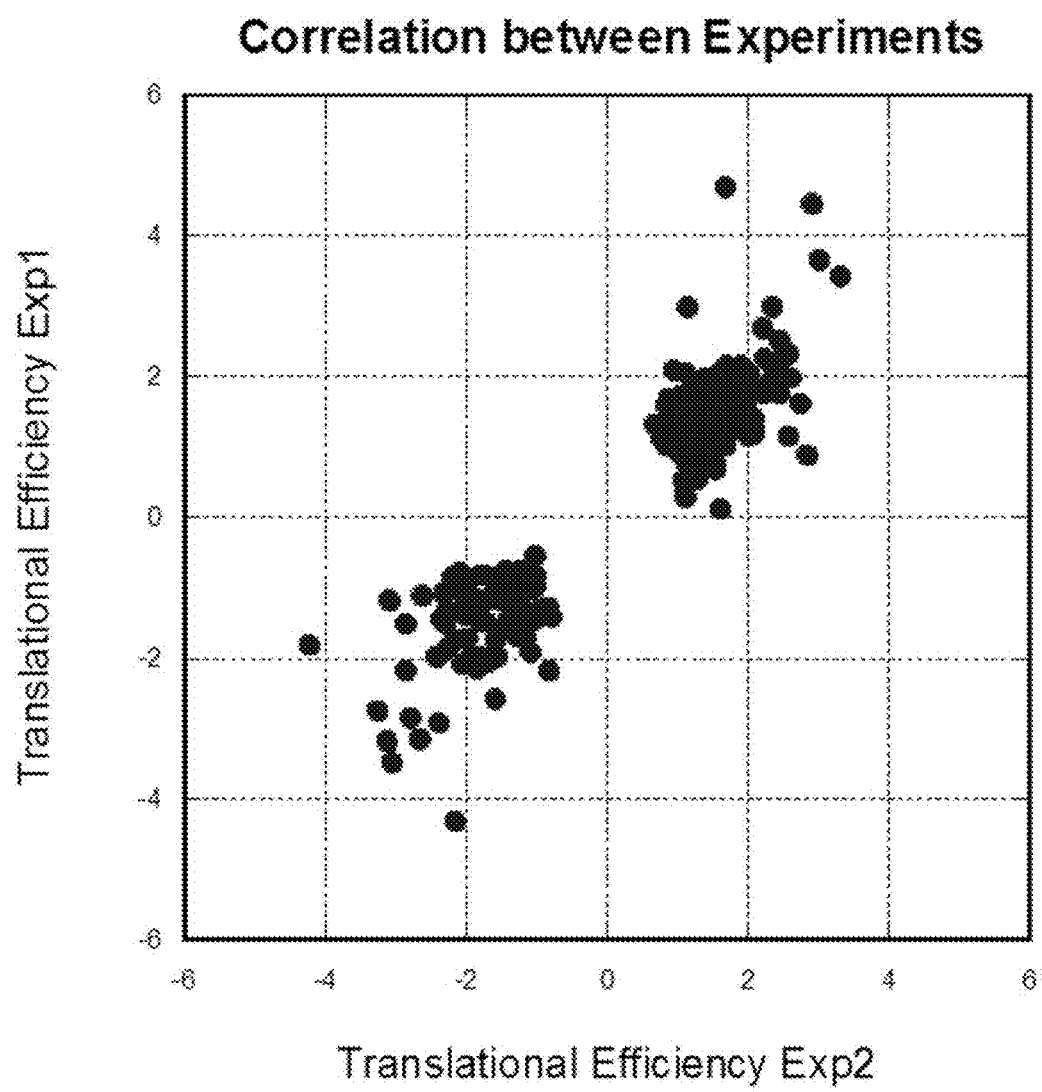
FIG. 13 shows the correlation of translational efficiency measurements between representative experiments in the form of a scatter plot. The alignment of the dots in a straight line indicate that the genes identified as translationally regulated are highly correlated between experiments, even when the change in translational efficiency for certain genes is not statistically significant in every experiment.

†The letters A-F each represent a log$_2$ fold change in translational profile caused by TGFβ, with the following values: A = <−2.5; B = <−1.5 to 2.5; C = <−1.0 to −1.5; D = <1.0 to 1.5; E = <1.5 to 2.5; F = >2.5. Letters A-C each represent a decrease in translation, while D-F each represent an increase in translation.
‡The effect of each compound in renormalizing the translational profile of each gene is shown as log$_2$ fold change as follows: − = <0.9; + = 0.9 to 1.5; ++ = 1.5 to 2.0; +++ = >2.0. Cells that are blank indicate no data was obtained.
ǁThe change in translational profile for each gene was not statistically significant (NS) in each of the three TGFβ modulation experiments (Exp), but each trended in the same direction and a scatter plot (see FIG. 13) shows that the translational regulation was highly correlated between experiments. Cells that are blank indicate the value obtained for that gene was statistically significant for that experiment.

Each of the compounds tested (PP242, silvestrol, pirfenidone, CPX, and TSA) showed a pronounced effect on renormalizing the levels of the fibrosis biomarkers procollagen and α-SMA, which had both increased in the presence of TGFβ (see Table 6). While these two biomarkers were not observed to be directly regulated at the translational level, ribosome profiling showed that expression of other genes was modulated at the translational level (see Table 7). Indeed, an analysis of the differential translational profile of healthy cells as compared to cells having a fibrotic disease state (i.e., TGFβ-modulated) as compared to the diseased cells treated with PP242, silvestrol, pirfenidone, CPX or TSA showed that each of these compounds is an agent that modulates translation in a fibrotic disease.

Figure 14:
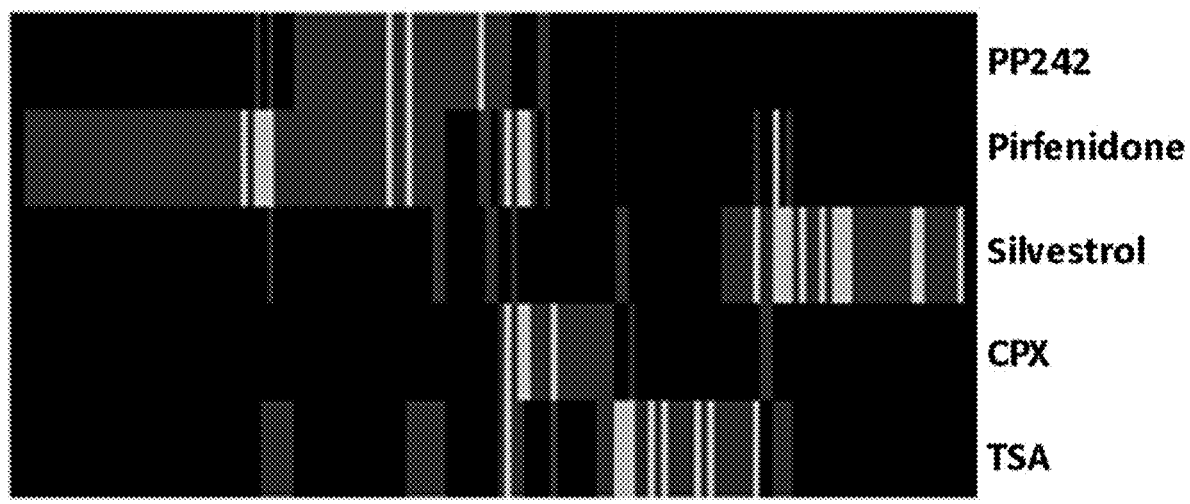
FIG. 14 shows a heat map of the differential translational profile for genes modulated (renormalized) by PP242, silvestrol, pirfenidone, CPX, or TSA (Δ $\log_2$ fold change (fibrotic cells vs. treated fibrotic cells) cut off of ≥1). Genes that show the most renormalization appear "white" in the heat map, while genes that are not renormalized appear "black" in the heat map and the genes that are "gray" had an intermediate level of renormalization.

Moreover, a heat map of the differential translational profile for these compounds (Δ log$_2$ fold change (fibrotic cells vs. treated fibrotic cells) cut off of ≥1) reveals that each agent (PP242, silvestrol, pirfenidone, CPX, and TSA) has a unique renormalization profile (see FIG. 14). Genes that show the most renormalization appear "white" in the heat map, while genes that are not renormalized appear "black" in the heat map and the genes that are "gray" had an intermediate level of renormalization. For example, pirfenidone renormalizes a number of genes that are also renormalized to the same degree by PP242, but many of the modulated genes are unique to pirfenidone. In contrast, each of silvestrol, CPX and TSA have very few genes that overlap with PP242 or pirfenidone, but each has its own strongly unique fingerprints.

Overall, each compound produces a unique gene signature associated with translational efficiency. Pirfenidone uniquely modulated the translational efficiency of 35 genes (CREB5, DIAPH3, LGALS1, NACA, RPL12, RPL13A, RPL17, RPL21, RPL22L1, RPL23, RPL26, RPL27A, RPL28, RPL3, RPL30, RPL34, RPL36, RPL37, RPL37A, RPL4, RPL7A, RPS9, RPLP1, RPLP2, RPS10, RPS16, RPS19, RPS27, RPS5, RPS8, RPS9, SLC25A6, SOX6, STS, TKT) (i.e., not modulated, minimally modulated or not statistically significantly modulated by any of the other compounds tested), silvestrol uniquely modulated 26 genes (ABCA6, ANKH, CARD16, CEP192, DDX60, DNASE1L1, DYNC2H1, EDN1, HBEGF, HOMER1, INHBA, KDM6B, LENG9, MATN3, MYO19, NRG1, PABPC4, PLD1, PLEKHA5, RASD1, SGIP1, SLC2A12, SNRPA, TEN1, TOP2A, TRERF1), PP242 uniquely modulated five genes (C9orf85, EIF3E, GAPDH, HNRNPA1, MRPL45), CPX uniquely modulated six genes (CES1, LAMP5, PAQR5 PLEKHG1, ROBO2, TOMM7) and TSA uniquely modulated 13 genes (AOX1, ARPC1A, AURKA, C12orf57, GPSM2, KITLG, MAP3K5, MURC, NOV, RPL14, SLC15A3, SOX5, ZNF608).

In addition, there are unique gene signatures that overlap between two compounds. For example, there are a total of 19 genes (ANKDD1A, ATP5G2, CHCHD10, DNAJC22, FGF5, FMO2, GNB2L1, GLTSCR2, HIGD2A, IFIH, MTUS1, RPS18, RPL18A, RPL31, RPL35A, RPL5, RPS18, RPS29, SPATA6) modulated by both pirfenidone and PP242; one gene (RPS6KA5) modulated by both silvestrol and PP242; one gene (BIVM) modulated by both PP242 and CPX; two genes (ACTA1, KRT7) modulated by both pirfenidone and CPX; four genes (AMIGO3, CCDC102B, RPL10, TAF1D) modulated by both pirfenidone and TSA; two genes (ADAMTS5, LAMB3) modulated by both silvestrol and CPX; eight genes (CLCF1, EPB41L1, GAS2L3, IRAK3, LPAR3, PCBP2, PDE7B, TMTC1) modulated by silvestrol and TSA; five genes (FRMD4A, GDF10, OBSCN, PLEKHA6, SHC3) modulated by CPX and TSA.

Finally, there are unique gene signatures that overlap between groups of three or four compounds. For example, one gene (THBS3) was modulated by pirfenidone, silvestrol and PP242; one gene (RPS28) was modulated by pirfenidone, CPX and PP242; five genes (EEF1A1, EEF2, EIF4B, FMO2, RAB3D) were modulated by pirfenidone, TSA and PP242; three genes (CIT, PDE4B, PPARG) were modulated by pirfenidone, TSA and silvestrol; one gene (SLC40A1) was modulated by pirfenidone, TSA and CPX; three genes (ASPM, CA5B, GLCCI1) were modulated by pirfenidone, PP242, silvestrol and TSA; two genes (GLTSCR2, P2RX7) were modulated by pirfenidone, PP242, CPX and TSA; and one gene (STAMBPL1) was modulated by pirfenidone, silvestrol, CPX and TSA.

As is evident, the modulated genes (i.e., targets for drug development) include those that encode proteins of the translation machinery, regulators of the translation machinery, proteins that modify disease, and downstream proteins.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Patent Application No. 61/937,272, are incorporated herein by reference in their entirety. Aspects of the embodiments can be modified, if necessary, to employ concepts of the various patents, applications and publications to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for treating or ameliorating a fibrotic disease, comprising administering to a subject having the fibrotic disease a therapeutically effective amount of a modulator specific for eIF4A, eIF4E, or both, thereby treating or ameliorating the fibrotic disease, wherein the fibrotic disease is idiopathic pulmonary fibrosis.

2. The method according to claim 1, wherein the modulator is administered after a fibrotic lesion has developed in the subject.

3. The method according to claim 1, wherein the modulator is formulated with a pharmaceutically acceptable excipient.

4. The method according to claim 1, wherein the modulator is administered in combination with one or more adjunctive therapeutic agents.

5. The method according to claim 4, wherein the one or more adjunctive therapeutic agents is selected from angiotensin converting enzyme inhibitor, nintedanib, STX-100, QAX576, CNTO-888, SD-208, SB-525334, GC1008, BMS-986202, AM152, lebrikizumab, tralokinumab, SAR156597, PRM-151, simtuzumab (AB0024, GS-6624), GSK2126458, FG-3019, captopril, genistein, silvestrol or derivatives thereof, pirfenidone, pateamine A or derivatives thereof, hippuristanol, or EUK-207.

6. The method according to claim 1, wherein the subject is a human.

7. The method of claim 1, wherein the modulator specific for eIF4A or eIF4E is selected from the group consisting of silvestrol, an siRNA or a derivative thereof, and any combinations thereof.

8. The method of claim 4, wherein (a) the modulator comprises a modulator of eIF4A and the adjunctive therapeutic agent comprises a modulator of EIF2AK1, (b) the modulator comprises a modulator of eIF4A and the adjunctive therapeutic agent comprises a modulator of deoxyhypusine synthase (DHPS), or (c) the modulator comprises a modulator of eIF4A and the adjunctive therapeutic agent comprises a modulator of deoxyhypusine hydroxylase (DOHH).

9. The method of claim 4, wherein (a) the modulator comprises a modulator of eIF4E and the adjunctive therapeutic agent comprises a modulator of EIF2AK1, (b) the modulator comprises a modulator of eIF4E and the adjunctive therapeutic agent comprises a modulator of deoxyhypusine synthase (DHPS), or (c) the modulator comprises a modulator of eIF4E and the adjunctive therapeutic agent comprises a modulator of deoxyhypusine hydroxylase (DOHH).

* * * * *